(12) United States Patent
O'Connor-McCourt et al.

(10) Patent No.: US 8,734,760 B2
(45) Date of Patent: *May 27, 2014

(54) ANTAGONISTS OF LIGANDS AND USES THEREOF

(71) Applicant: National Research Council of Canada, Ottawa (CA)

(72) Inventors: Maureen D. O'Connor-McCourt, Beaconsfield (CA); Traian Sulea, Kirkland (CA); John C. Zwaagstra, Chomedey-Laval (CA); Jason Baardsnes, Montreal (CA)

(73) Assignee: National Research Coucil of Canada, Ottawa, Ontario (CA)

( * ) Notice: Subject to any disclaimer, the term of this patent is extended or adjusted under 35 U.S.C. 154(b) by 53 days.

This patent is subject to a terminal disclaimer.

(21) Appl. No.: 13/654,703

(22) Filed: Oct. 18, 2012

(65) Prior Publication Data

US 2013/0089499 A1 Apr. 11, 2013

Related U.S. Application Data

(62) Division of application No. 12/450,226, filed as application No. PCT/CA2008/000547 on Mar. 19, 2008, now Pat. No. 8,318,135.

(60) Provisional application No. 60/907,059, filed on Mar. 19, 2007.

(51) Int. Cl.
*A61K 38/16* (2006.01)
*C07K 14/47* (2006.01)

(52) U.S. Cl.
USPC .......................... 424/9.1; 514/21.2; 530/350

(58) Field of Classification Search
None
See application file for complete search history.

(56) References Cited

U.S. PATENT DOCUMENTS 5,844,099 A 12/1998 Stahl et al.
6,472,179 B2 10/2002 Stahl et al.
(Continued)

FOREIGN PATENT DOCUMENTS

| CA | 2345109 | 4/2000 |
| WO | 03020906 | 3/2003 |
| WO | 2008157367 | 12/2008 |

OTHER PUBLICATIONS

Allendorph et al., "Structure of the Ternary Signaling Complex of a TGF-B Superfamily Member", PNAS vol. 103 (20), p. 7643-7648, 2006.

(Continued)

*Primary Examiner* — Jeffrey E Russel
(74) *Attorney, Agent, or Firm* — Sonia Patnaude

(57) ABSTRACT

The invention provides multivalent ligand binding agents (traps) for members of the TGF-β superfamily and polypeptide linkers and methods for making and using such constructs. The traps may be used as therapeutic or diagnostic (imaging or non-imaging) agents for diseases/disorders caused by over-production/activity of the target ligand. In an embodiment of the invention there is provided a multivalent binding agent with affinity for a member of the TGF-β superfamily, the agent having the general structure I:

(<bd1>-linker1)$_k$-[{<bd1>-linker2-<bd2>-linker3$_f$}$_n$-(<bd3>)$_m$-(linker4-<bd4>)$_d$]$_h$, where:
n and h are independently greater than or equal to 1;
d, f, m and k are independently equal to or greater than zero;
bd's are polypeptide binding domains having an affinity for the same member of the TGF-β superfamily; and,
linkers are unstructured polypeptide sequences.

21 Claims, 29 Drawing Sheets

Examples of in-line fused receptor ectodomains as homo-bivalent single-chain bivalent traps of several TGF-β-family growth factors. The "/" sign indicates the point of fusion.

(56) References Cited

U.S. PATENT DOCUMENTS

| | | | |
|---|---|---|---|
| 6,897,294 | B2 | 5/2005 | Davis-Smyth et al. |
| 6,916,913 | B2 | 7/2005 | Jessell et al. |
| 8,318,135 | B2 * | 11/2012 | O'Connor-McCourt et al. ............................ 424/9.1 |
| 2002/0004037 | A1 | 1/2002 | Koteliansky et al. |
| 2002/0173621 | A1 | 11/2002 | Sledziewsky et al. |
| 2003/0125251 | A1 | 7/2003 | Wakefield et al. |
| 2004/0176282 | A1 | 9/2004 | Dalby et al. |
| 2007/0086942 | A1 | 4/2007 | Chang et al. |
| 2007/0154994 | A1 | 7/2007 | De Crescenzo et al. |
| 2007/0244042 | A1 | 10/2007 | Sun et al. |

OTHER PUBLICATIONS

Andreeva et al., "Data Growth and its Impact on the SCOP Database: New Developments", Nucleic Acids Research, vol. 36, p. D419-D425, 2008.

Berman et al., The Protein Data Bank, Nucleic Acids Research, vol. 28(1), p. 235-242, 2000.

Boesen et al., "The 1.1 A Crystal Structure of Human TGF-B Type II Receptor Ligand Binding Domain", Structure, vol. 10, p. 913-919, 2002.

Case et al., "The Amber Biomolecular Simulation Programs", J. Comput. Chem., vol. 26, p. 1668-1688, 2005.

Cass et al., "Purification of Recombinant Proteins from Mammalian Cell Culture Using a Generic Double-Affinity Chromatography Scheme", Protein Expression and Purification, vol. 40, p. 77-85, 2005.

Cornell et al., "A Second Generation Force Field for the Simulation of Proteins, Nucleic Acids, and Organic Molecules", J. Am. Chem. Soc., vol. 117, p. 5179-5197, 1995.

Darden et al., "Particle Mesh Ewald: An Nlog (N) Method for Ewald Sums in Large Systems", J. Chem. Phys., vol. 98 (12), p. 10089-10092, 1993.

Decrescenzo et al., "Real-Time Monitoring of the Interactions of Transforming Growth Factor-B (TGF-B) Isoforms with Latency-Associated Protein and the Ectodomains of the TGF-B Type II and III Receptors Reveals Different Kinetic Models and Stoichiometries of Binding", J. of Biological Chemistry, vol. 276(32), p. 29632-29643, 2001.

Decrescenzo et al., "Enhancement of the Antagonistic Potency of Transforming Growth Factor-B Receptor Extracellular Domains by Coiled Coil-Induced Homo- and Heterodimerization", J. of Biological Chemistry, vol. 279(25), p. 26013-26018, 2004.

Deep et al., "Solution Structure and Backbone Dynamics of the TGFB Type II Receptor Extracellular Domain", Biochemistry, vol. 42, p. 10126-10139, 2003.

Dennler et al., "Direct Binding of Smad3 and Smad4 to Critical TGFB-Inducible Elements in the Promoter of Human Plasminogen Activator Inhibitor-Type 1 Gene", The EMBO Journal, vol. 17(11), p. 3091-3100, 1998.

Duan et al., "A Point-Charge Force Field for Molecular Mechanics Simulations of Proteins Based on Condensed-Phase Quantum Mechanical Calculations", J. Comput. Chem., vol. 24, p. 1999-2012, 2003.

Economides et al., "Cytokine Traps: Multi-Component, High-Affinity Blockers of Cytokine Action", Nature Medicine, vol. 9(1), p. 47-52, 2002.

Extended European Search Report on EP 08733651.7, 2010.

Esparza-Lopez et al., "Ligand Binding and Functional Properties of Betaglycan, a Co-Receptor of the Transforming Growth Factor-B Superfamily", The Journal of Biological Chemistry, vol. 276(18), p. 14588-14596, 2001.

Finn et al., "Pfam: Clans, Web Tools and Services", Nucleic Acids Research, vol. 34, p. D247-D251, 2006.

Greenwald et al., "The BMP7/ActRII Extracellular Domain Complex Provides New Insights into the Cooperative Nature of Receptor Assembly", Molecular Cell, vol. 11, p. 605-617, 2003.

Greenwald et al., "A Flexible Activin Explains the Membrane-Dependent Cooperative Assembly of TGF-B Family Receptors", Molecular Cell, vol. 15, p. 485-489, 2004.

Groppe et al., "Cooperative Assembly of TGF-B Superfamily Signaling Complexes is Mediated by Two Disparate Mechanisms and Distinct Modes of Receptor Binding", Molecular Cell, vol. 29, p. 157-168, 2008.

Hart et al., "Crystal Structure of the Human TBR2 Ectodomain-TGF-B3 Complex", Nature Structural Biology, vol. 9 (3), p. 203-208, 2002.

Hinck et al., "Transforming Growth Factor B1: Three-Dimensional Structure in Solution and Comparison with the X-Ray Structure of Transforming Growth Factor B2", Biochemistry, vol. 35, p. 8517-8534, 1996.

Holash et al., "VEGF-Trap: A VEGF Blocker with Potent Antitumor Effects", PNAS, vol. 99(17), p. 11393-11398, 2002.

International Preliminary Report on Patentability dated Jun. 5, 2009 on PCT-CA2008-000547.

Kinglsey, D.M., "The TGF-Beta Superfamily: New Members, New Receptors, and New Genetic Tests of Function in Different Organisms", Genes and Development, vol. 8, p. 135, 1994.

Kirsch et al., "Crystal Structure of the BMP-2-BRIA Ectodomain Complex", Nature Structural Biology, vol. 7(6), p. 492-496, 2000.

Larrain et al., "BMP-Binding Modules in Chordin: A Model for Signalling Regulation in the Extracellular Space", Development 127, p. 821-830, 2000.

Lee et al., "Distinguish Protein Decoys by Using a Scoring Function Based on a New Amber Force Field, Short Molecular Dynamics Simulations, and the Generalized Born Solvent Model", Proteins: Structure, Function, and Bioinformatics, vol. 55, p. 620-634, 2004.

Mittl et al., "The Crystal Structure of TGF-B3 and Comparison to TGF-B2: Implications for Receptor Binding", Protein Science, vol. 5, p. 1261-1271, 1996.

Naim et al., "Solvated Interaction Energy (SIE) for Scoring Protein—Ligand Binding Affinities. 1. Exploring the Parameter Space", J. Chem. Inf. Model, vol. 47, p. 122-133, 2007.

Pham et al., "Transient Gene Expression in HEK293 Cells: Peptone Addition Posttransfection Improves Recombinant Protein Synthesis", Biotechnology and Bioengineering, vol. 90(3), p. 332-344, 2005.

Ryckaert et al., "Numerical Integration of the Cartesian Equations of Motion of a System with Constraints: Molecular Dynamics of n-Alkanes", Journal of Computational Physics, vol. 23, p. 327-341, 1977.

Thompson et al., "Structures of an ActRIIB: activin A Complex Reveal a Novel Binding Mode for TGF-B Ligand: Receptor Interactions", The EMBO Journal, vol. 22(7), p. 1555-1566, 2003.

Ward et al., "Prediction and Functional Analysis of Native Disorder in Proteins from the Three Kingdoms of Life", J. Mol. Biol., vol. 337, p. 635-645, 2004.

Written Opinion and International Search Report dated Jul. 18, 2008 on PCT-CA2008/000547.

Wyeth, TGF-B Superfamily Presentation.

Zilberberg et al., "A Rapid and Sensitive Bioassay to Measure Bone Morphogenetic Protein Activity", BMC Cell Biology, vol. 8:41, 2007.

US Office Action dated Jan. 10, 2012 for U.S. Appl. No. 12/450,226.
US Office Action dated Apr. 9, 2012 for U.S. Appl. No. 12/450,226.
EP Office Action dated Jul. 27, 2010 for EP application 08733651.7.
EP Office Action dated Dec. 8, 2010 for EP application 08733651.7.
EP Office Action dated Jul. 28, 2011 for EP application 08733651.7.
EP Office Action dated Jan. 24, 2012 for EP application 08733651.7.
EP Office Action dated Jun. 19, 2012 for EP application 08733651.7.
EP Office Action dated Jul. 31, 2012 for EP application 08733651.7.

* cited by examiner

Figure 1A. Amino-acid sequences corresponding to intrinsically unstructured regions in the extracellular portions of select TGF-β-superfamily receptors.

| TGF-β-superfamily receptor | Sequences corresponding to unstructured extracellular regions | |
|---|---|---|
| Human TβR-II | $^{1}$IPPHVQKSVNNDMIVTDNNGAVKFP$^{25}$ | SEQ ID NO 31 |
| | $^{127}$SEEYNTSNPD$^{136}$ | SEQ ID NO 32 |
| Human TβR-IIb | $^{1}$IPPHVQKSDVEMEAQKDEIICPSCNRTAHPLRHINNDMIVTDNNGAVKFP$^{50}$ | SEQ ID NO 33 |
| | $^{152}$SEEYNTSNPD$^{161}$ | SEQ ID NO 34 |
| Human TβR-I | $^{1}$AALLPGAT$^{8}$ | SEQ ID NO 35 |
| | $^{88}$PTTVKSSPGLGPVE$^{101}$ | SEQ ID NO 36 |
| Human ActR-IIa | $^{1}$AILGRSE$^{7}$ | SEQ ID NO 37 |
| | $^{99}$EMEVTQPTSNPVTPKPPYYNI$^{120}$ | SEQ ID NO 38 |
| Human ActR-IIb | $^{1}$SGRGEAET$^{8}$ | SEQ ID NO 39 |
| | $^{99}$EAGGPEVTYEPPPTAPT$^{116}$ | SEQ ID NO 40 |
| Human BMPR-Ia | $^{1}$QNLDSMLHGTGMKSDSDQKKSENGVTLAPED$^{31}$ | SEQ ID NO 41 |
| | $^{117}$PVVIGPFFDGSIR$^{129}$ | SEQ ID NO 42 |

Note: Residue numbering starts after signal peptide.

Figure 1B. Amino-acid sequences corresponding to structured ligand-binding domain regions in the extracellular portions of select TGF-β-superfamily receptors.

| TGF-β-superfamily receptor | Sequences corresponding to structured extracellular regions (ligand-binding domains) |
|---|---|
| Human TβR-II | $^{26}$QLCKFCDVRFSTCDNQKSCMSNCSITSICEKPQEVCVAVWRKNDENITLETVCHDPKLPYHDFILE DAASPKCIMKEKKKPGETFFMCSCSSDECNDNIIF$^{126}$     SEQ ID NO 43 |
| Human TβR-IIb | $^{51}$QLCKFCDVRFSTCDNQKSCMSNCSITSICEKPQEVCVAVWRKNDENITLETVCHDPKLPYHDFILE DAASPKCIMKEKKKPGETFFMCSCSSDECNDNIIF$^{151}$     SEQ ID NO 44 |
| Human TβR-I | $^{9}$ALQCFCHLCTKDNFTCVTDGLCFVSVTETTDKVIHNSMCIAEIDLIPRDRPFVCAPSSKTGSVTTY CCNQDHCNKIEL$^{87}$     SEQ ID NO 45 |
| Human ActR-IIa | $^{8}$TQECLFFNANWEKDRTNQTGVEPCYGDKDKRRHCFATWKNISGSIEIVKQGCWLDDINCYDRTDCVE KKDSPEVYFCCCEGNMCNEKFSYFP$^{98}$     SEQ ID NO 46 |
| Human ActR-IIb | $^{9}$RECIYYNANWELERTNQSGLERCEGEQDKRLHCYASWRNSSGTIELVKKGCWLDDFNCYDRQECVAT EENPQVYFCCCEGNFCNERFTHLPEAGGPEVTYEPPPTAPT$^{98}$     SEQ ID NO 47 |
| Human BMPR-Ia | $^{32}$TLPFLKCYCSGHCPDDAINNTCITNGHCFAIIEEDDQGETTLASGCMKYEGSDFQCKDSPKAQLRR TIECCRTNLCNQYLQPTLPPVVIGPFFDGSIR$^{116}$     SEQ ID NO 48 |

Note: Residue numbering starts after signal peptide.

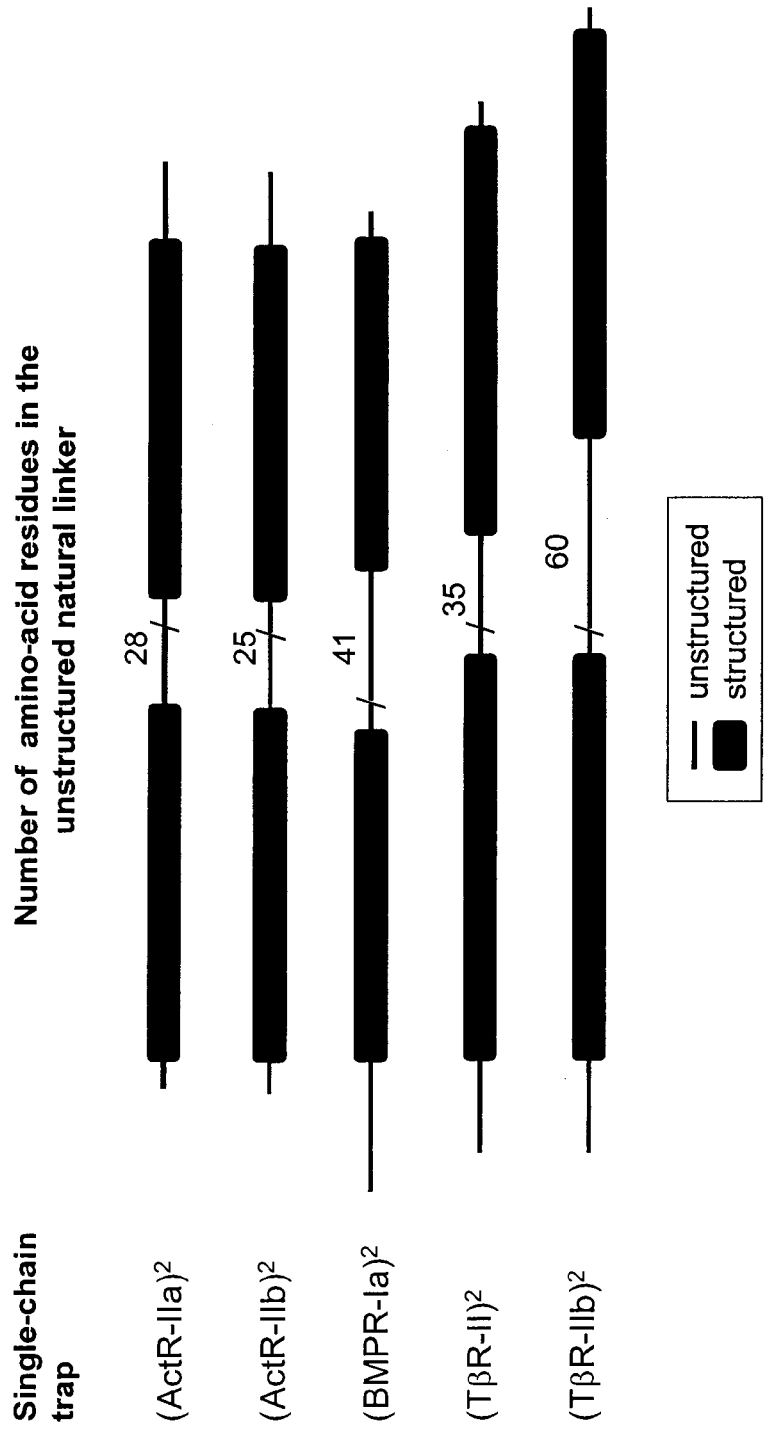
Figure 2A. Examples of in-line fused receptor ectodomains as homo-bivalent single-chain bivalent traps of several TGF-β-family growth factors. The "/" sign indicates the point of fusion.

Figure 2B. Examples of sequences corresponding to natural linkers of homo-bivalent single-chain traps resulting from fusion of the entire extracellular portions of select TGF-β-superfamily receptors.

| Single-chain trap | Linker length (a.a.) | Linkers of natural sequence | |
|---|---|---|---|
| (TβR-II)$_2$ | 35 | $^{127}$SEEYNTSNPD:IPPHVQKSVNNDMIVTDNNGAVKFP$^{161}$ | SEQ ID NO 49 |
| (TβR-IIb)$_2$ | 60 | $^{127}$SEEYNTSNPD:IPPHVQKSDVEMEAQKDEIICPSCNRTAHPLRHINNDMIVTDNNGAVKFP$^{187}$ | SEQ ID NO 50 |
| (ActR-IIb)$_2$ | 25 | $^{99}$EAGGPEVTYEPPPTAPT:SGRGEAET$^{124}$ | SEQ ID NO 51 |
| (BMPR-Ia)$_2$ | 44 | $^{117}$PVVIGPFFDGSIR:QNLDSMLHGTGMKSDSDQKKSENGVTLAPED$^{160}$ | SEQ ID NO 52 |

Notes: Residue numbering corresponds to trap construct and starts after N-terminal tag. Fusion position is indicated by (:).

Figure 2C. Examples of sequences corresponding to artificial linkers for homo-bivalent single-chain traps at varying sequence identity to natural linker sequences.

| Single-chain parent trap | Identity to natural linker (%) | Linkers of artificial sequence | |
|---|---|---|---|
| (BMPR-Ia)² | 98 | $^{117}$PVVIGPFFDGSIRG<u>N</u>LDSMLHGTGMKSDSDQKKSENGVTLAPED$^{160}$ | SEQ ID NO 53 |
| (TβR-II)² | 97 | $^{127}$SEEYNTSNPDGPPHVQKSVNNDMIVTD<u>N</u>NGAVKFP$^{161}$ | SEQ ID NO 54 |
| (ActR-IIb)² | 96 | $^{99}$<u>E</u>AGGPEVTGEPPPTAPTSGRGEAET$^{124}$ | SEQ ID NO 55 |
| (TβR-IIb)² | 95 | $^{127}$SEEYNTSNPDGGRHVQKSDVEMEAQKDEIICPSCNRTAHPLRHINNDMIVTDNNGAVKFP$^{187}$ | SEQ ID NO 56 |
| (TβR-II)² | 94 | $^{127}$SEEYNTSNPDGGPHVQKSVNNDMIVTDNNGAVKFP$^{161}$ | SEQ ID NO 57 |
| (TβR-II)² | 91 | $^{127}$SEEYNTSNPDGGRHVQKSVNNDMIVTDNNGAVKFP$^{161}$ * | SEQ ID NO 58 |
| (TβR-IIb)² SEQ ID NO 59 | 85 | $^{127}$SEEYNTSNPS<u>GGGSGGG</u>MEAQKDEIICPSCNRTAHPLRHINNDMIVTDNNGAVKFP$^{187}$ | |
| (TβR-II)² | 80 | $^{127}$SEEYNTSNPS<u>GGGSGGG</u>KSVNNDMIVTDNNGAVKFP$^{161}$ | SEQ ID NO 60 |
| (TβR-II)² | 69 | $^{127}$SEEYNTSNPS<u>GGGSGGGSGGGSGGG</u>DMIVTDNNGAVKFP$^{161}$ | SEQ ID NO 61 |
| (TβR-IIb)² | 57 | $^{127}$SEEYNTSNPDIPPHVQKS<u>GGGSGGGSGGGSGGGSGGGSGGGSGGGSGGG</u>NNDMIVTDNNGAVKFP$^{187}$ | SEQ ID NO 62 |
| (TβR-IIb)² | 43 | $^{127}$SEEYNTSNPD<u>GGGSGGGSGGGSGGGSGGGSGGGSGGGSGGGSGGGSGGGSGGG</u>NNDMIVTDNNGAVKFP$^{187}$ | SEQ ID NO 63 |

Notes: Residue numbering corresponds to single-chain trap. Changed amino-acid residues relative to natural sequence are underlined.
* This linker corresponds to the "prototype" (TβR-II)² described in the text.

Figure 2D. Examples of sequences corresponding to varying the linker length for homo-bivalent single-chain traps by deleting or repeating of natural sequences, or by inserting of artificial sequences, into the natural linker sequence.

| Single-chain trap | Linker length (a.a.) | Linker sequences | |
|---|---|---|---|
| (TβR-II)² | 35 | $^{127}$SEEYNTSNPDIPPHVQKSVNNDMIVTDNNGAVKFP$^{161}$ | SEQ ID NO 64 |
| (TβR-II)²-repeat | 48 | $^{127}$SEEYNTSNPDIPPHVQKSVNNDMIPPHVQKSVNNDMIVTDNNGAVKFP$^{174}$ | SEQ ID NO 65 |
| (TβR-II)²-delete | 33 | $^{127}$SEEYNTSN--PPHVQKSVNNDMIVTDNNGAVKFP$^{159}$ | SEQ ID NO 66 |
| (TβR-II)2-G8 | 43 | $^{127}$SEEYNTSNPDGGGGGGGIPPHVQKSVNNDMIVTDNNGAVKFP$^{169}$ | SEQ ID NO 67 |
| (TβR-II)²-(G3S)₃ | 47 | $^{127}$SEEYNTSNPDGGGSGGGSGGGSIPPHVQKSVNNDMIVTDNNGAVKFP$^{173}$ | SEQ ID NO 68 |
| (TβR-IIb)² | 60 | $^{127}$SEEYNTSNPDIPPHVQKSDVEMEAQKDEIICPSCNRTAHPLRHINNDMIVTDNNGAVKFP$^{187}$ | SEQ ID NO 69 |
| (TβR-IIb)²-delete | 53 | $^{127}$SEEYNTSNPDIPPHVQKSDVEMEAQKDE------RTAHPLRHINNDMIVTDNNGAVKFP$^{180}$ | SEQ ID NO 70 |
| (ActR-IIb)² | 25 | $^{99}$EAGGPEVTYEPPPTAPTSGRGEAET$^{124}$ | SEQ ID NO 71 |
| (ActR-IIb)²-G10 | 35 | $^{99}$EAGGPEVTYEPPPTAPTGGGGGGGGGSGRGEAET$^{134}$ | SEQ ID NO 72 |
| (BMPR-Ia)² | 44 | $^{117}$PVVIGPFFDGSIRQNLDSMLHGTGMKSDSDQKKSENGVTLAPED$^{160}$ | SEQ ID NO 73 |
| (BMPR-Ia)²-delete | 40 | $^{117}$PVVIGP--DGSIRQNLDS--HGTGMKSDSDQKKSENGVTLAPED$^{156}$ | SEQ ID NO 74 |

Notes: Residue numbering corresponds to trap construct and starts after N-terminal tag. Added amino-acid sequences, either natural or artificial, are underlined. Deletions are denoted by dashes. Natural linker sequences are also included as reference.

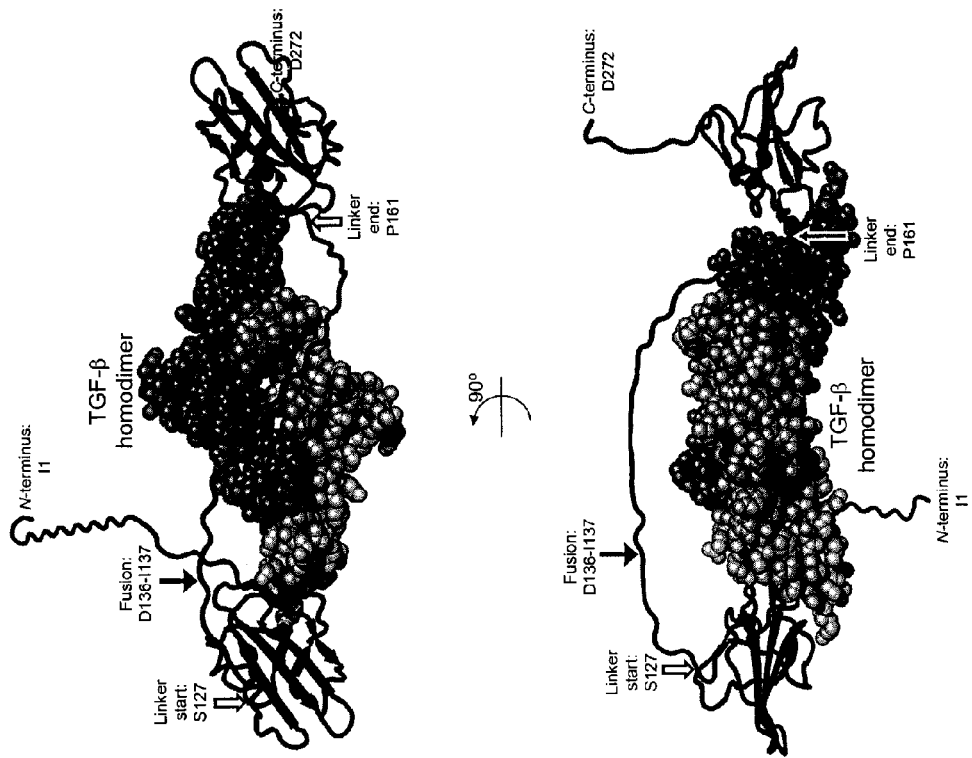
Figure 3. Illustration of the (TβR-II)² single-chain trap construct on a three-dimensional molecular mechanical model of the (TβR-II)² single-chain trap b

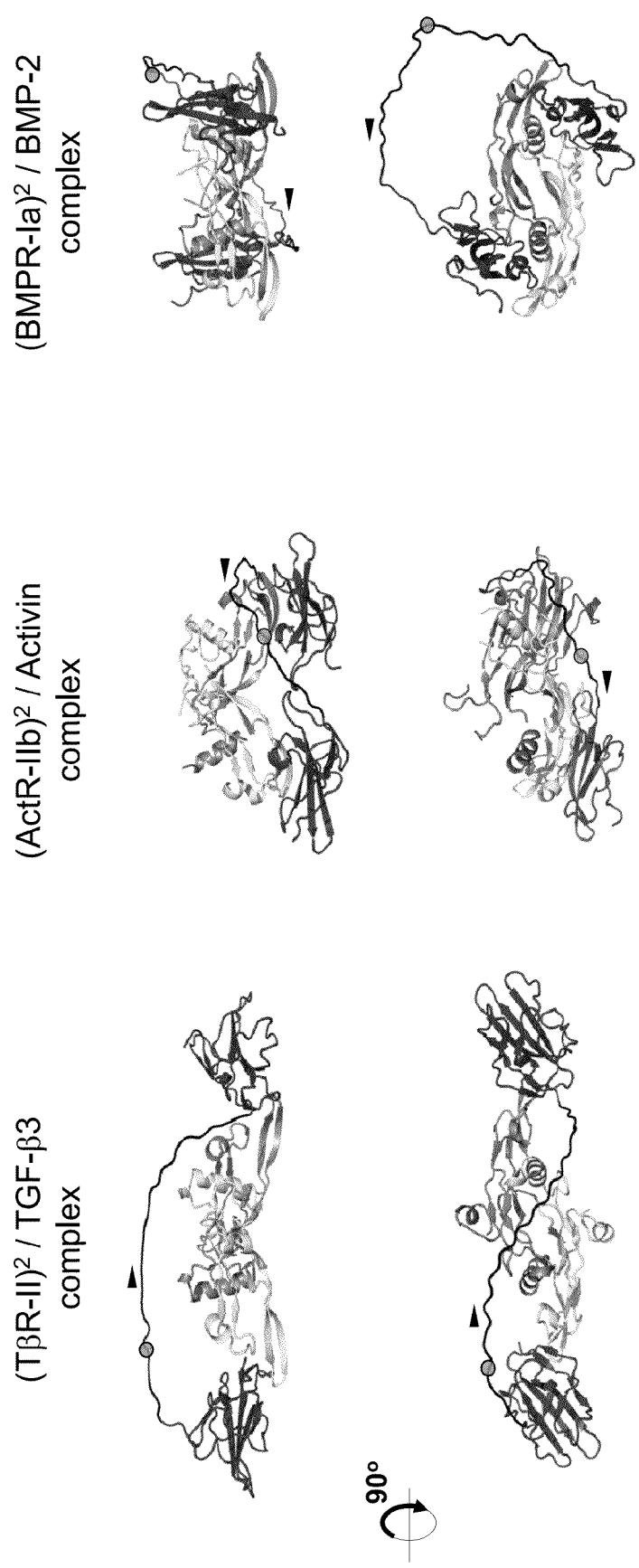
Figure 4. Feasibility of trap constructs with natural linkers from three-dimensional structural models.

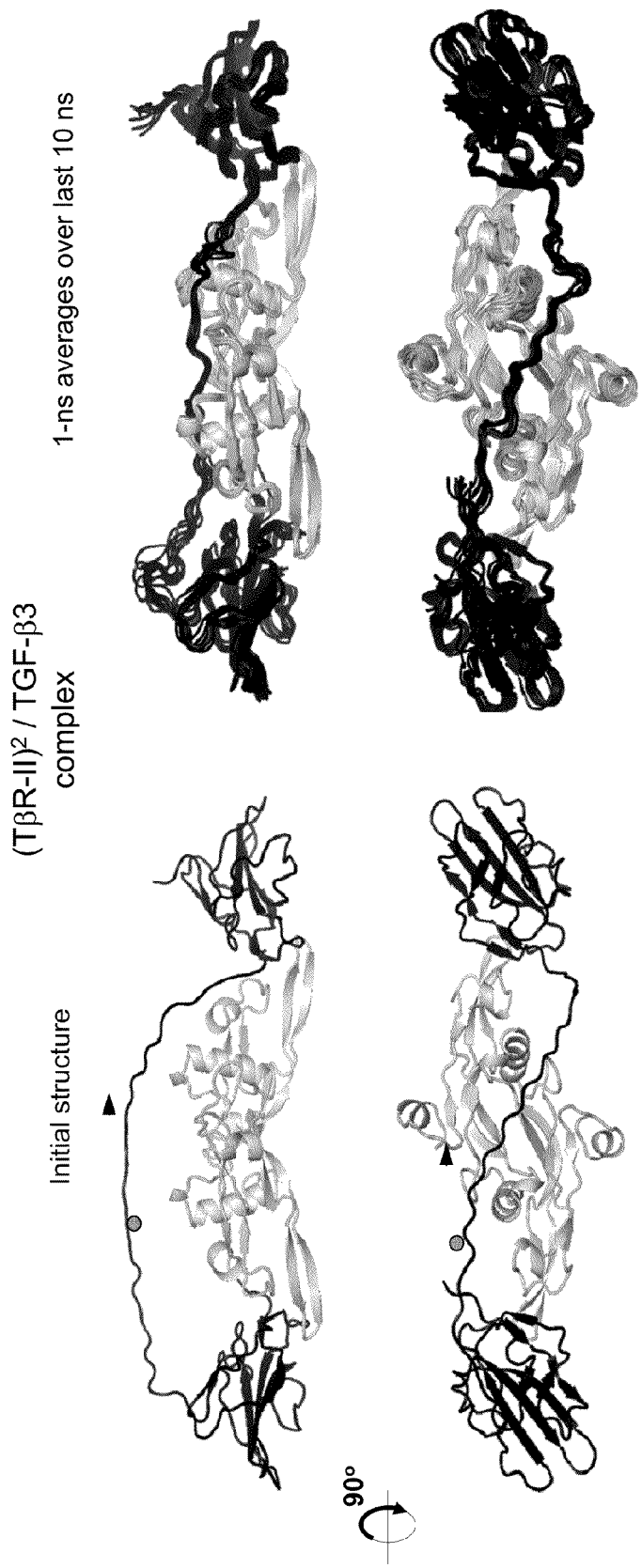
Figure 5A. Molecular dynamics (MD) model for the (TβR-II)² homo-bivalent single-chain trap bound to the TGF-β3 growth factor (right images). An initial model with energy-minimized linker and with ligand-binding domains in crystallographic positions bound onto the growth factor is also shown for reference (left images, see also Figs. 3 and 4).

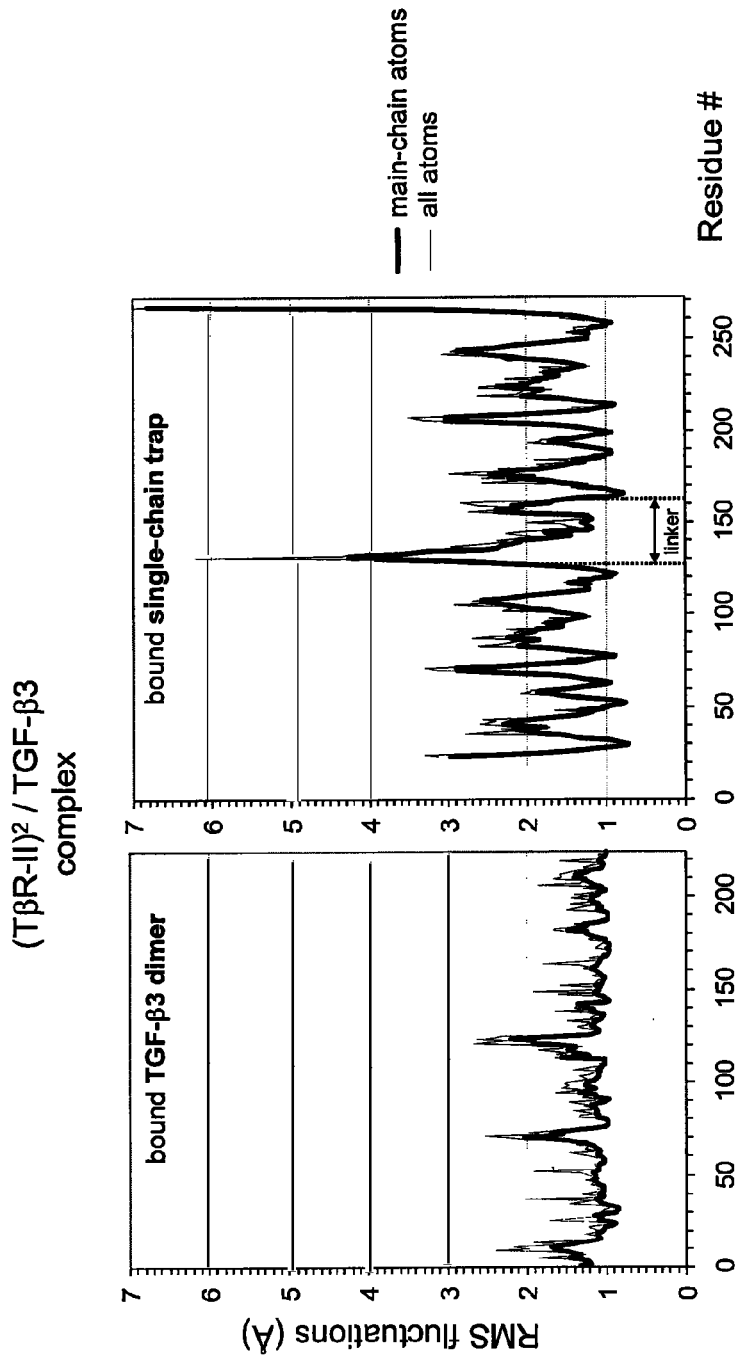
Figure 5B. Per residue root-mean-square (RMS) fluctuations of the (TβR-II)² / TGF-β3 complex, time-averaged over the last 10 ns of MD simulation.

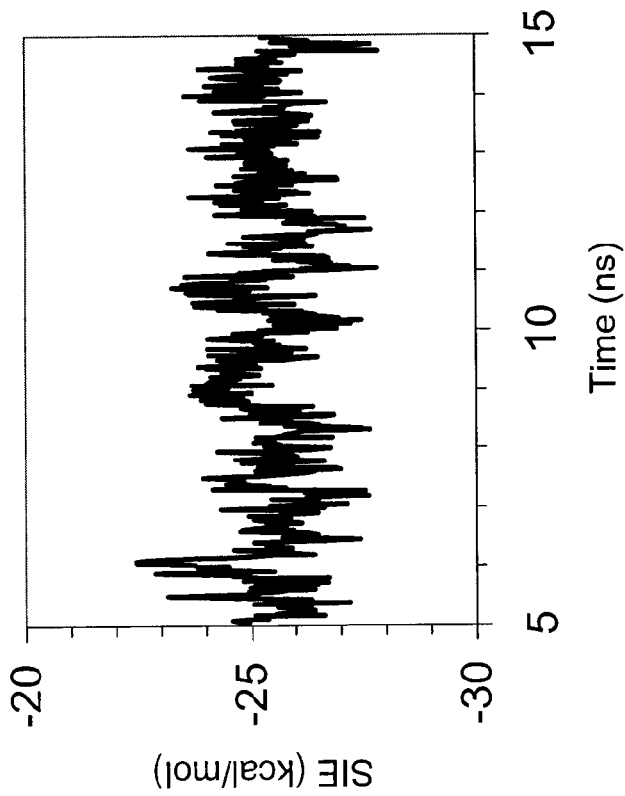
Figure 5C. Solvated Interaction Energy (SIE) between the single-chain (TβR-II)² trap and the TGF-β3 ligand over the last 10 ns of MD simulation of their complex, with an average value of -25.4 kcal/mol.

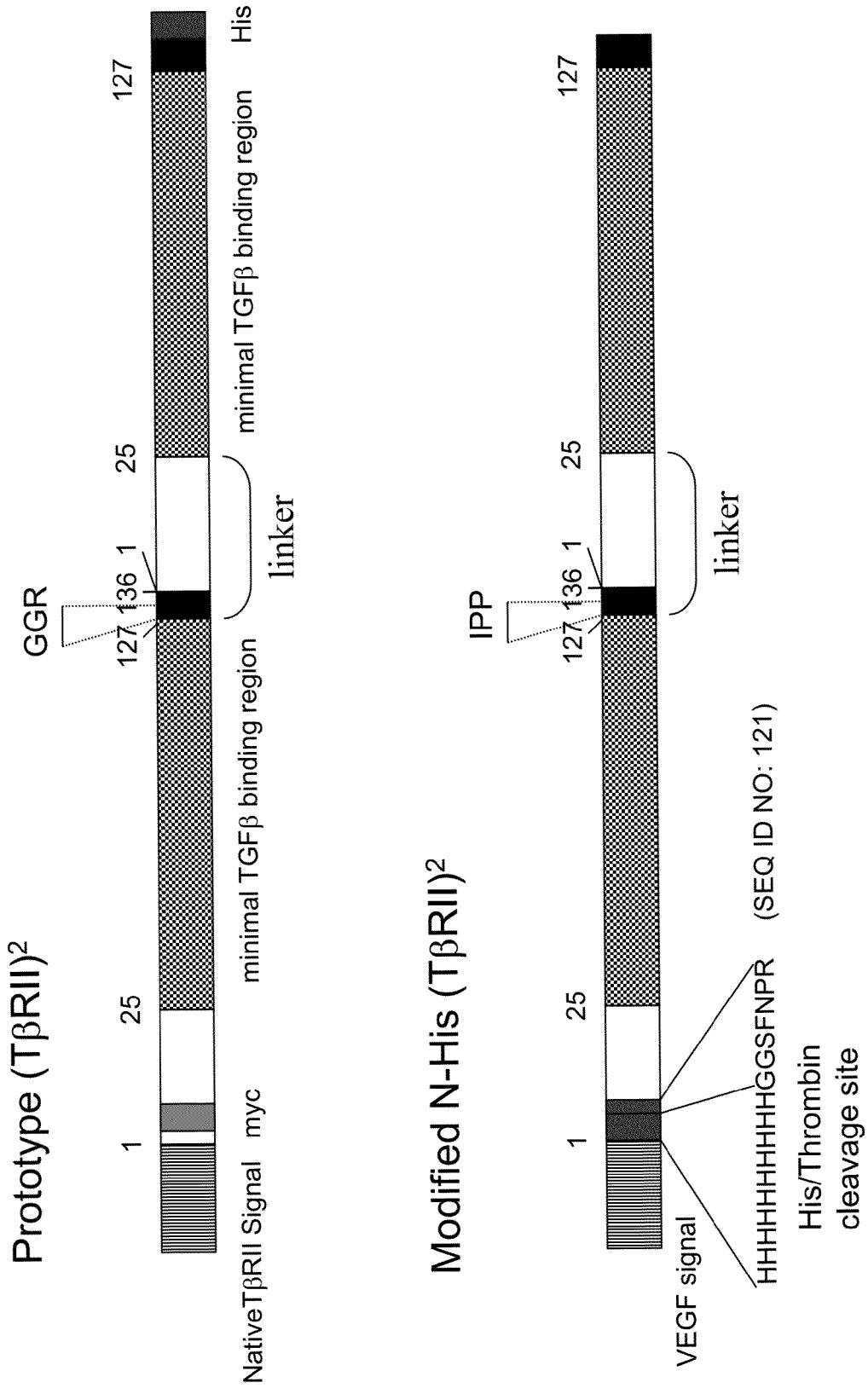
Figure 6. Schematic of prototype (TβRII)² and modified N-His (TβRII)² traps.

Figure 7A. Surface plasmon resonance sensogram showing prototype (TβRII)² (in diluted conditioned media from different % transfections) binding to surface-immobilized TGF-β3 ligand.

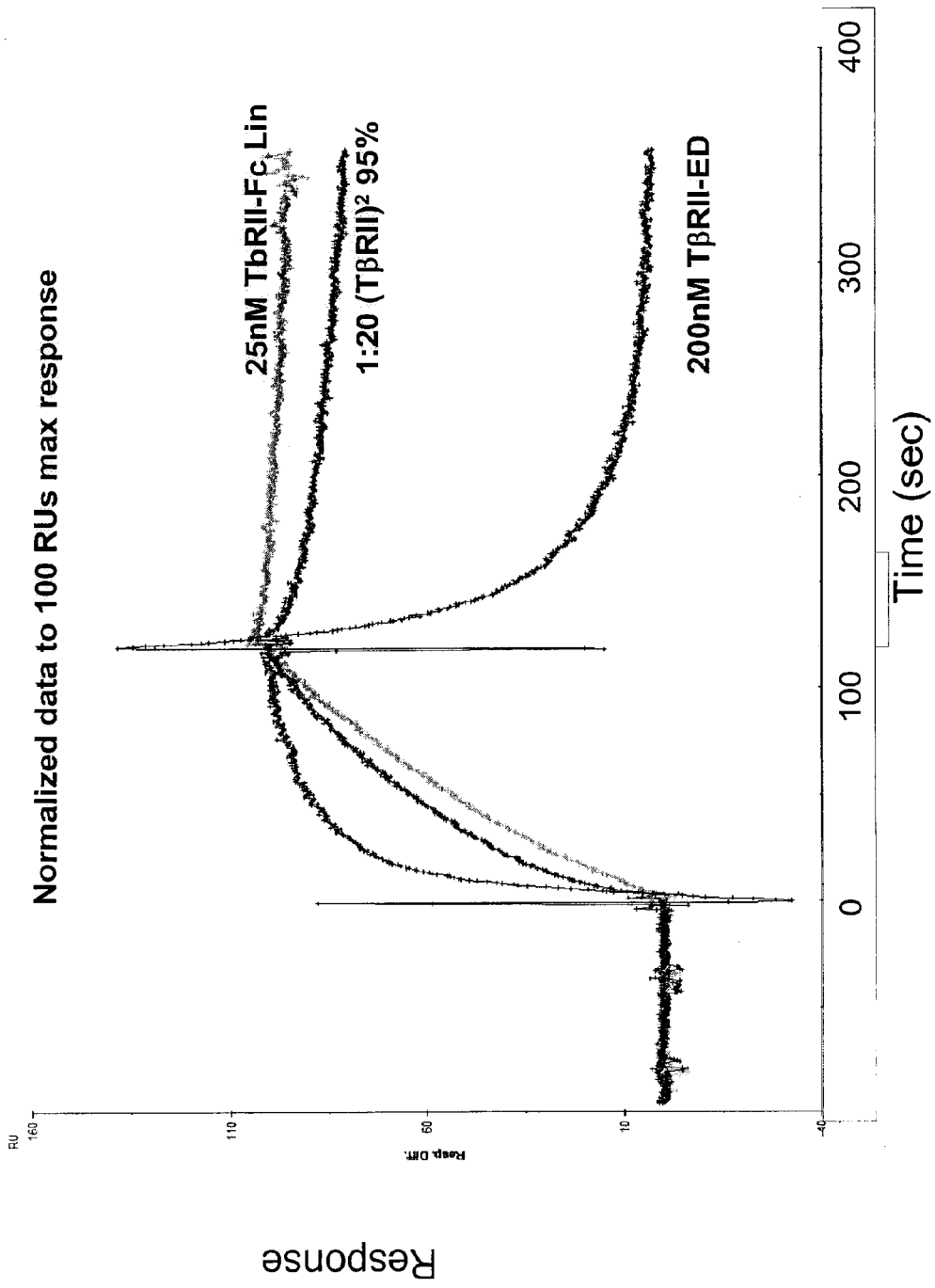
Figure 7B. Surface plasmon resonance sensograms comparing binding of bivalent prototype (TβRII)$^2$, bivalent TβRII-Fc and monovalent TβRII to 270 RUs surface-immobilized TGF-β3 ligand.

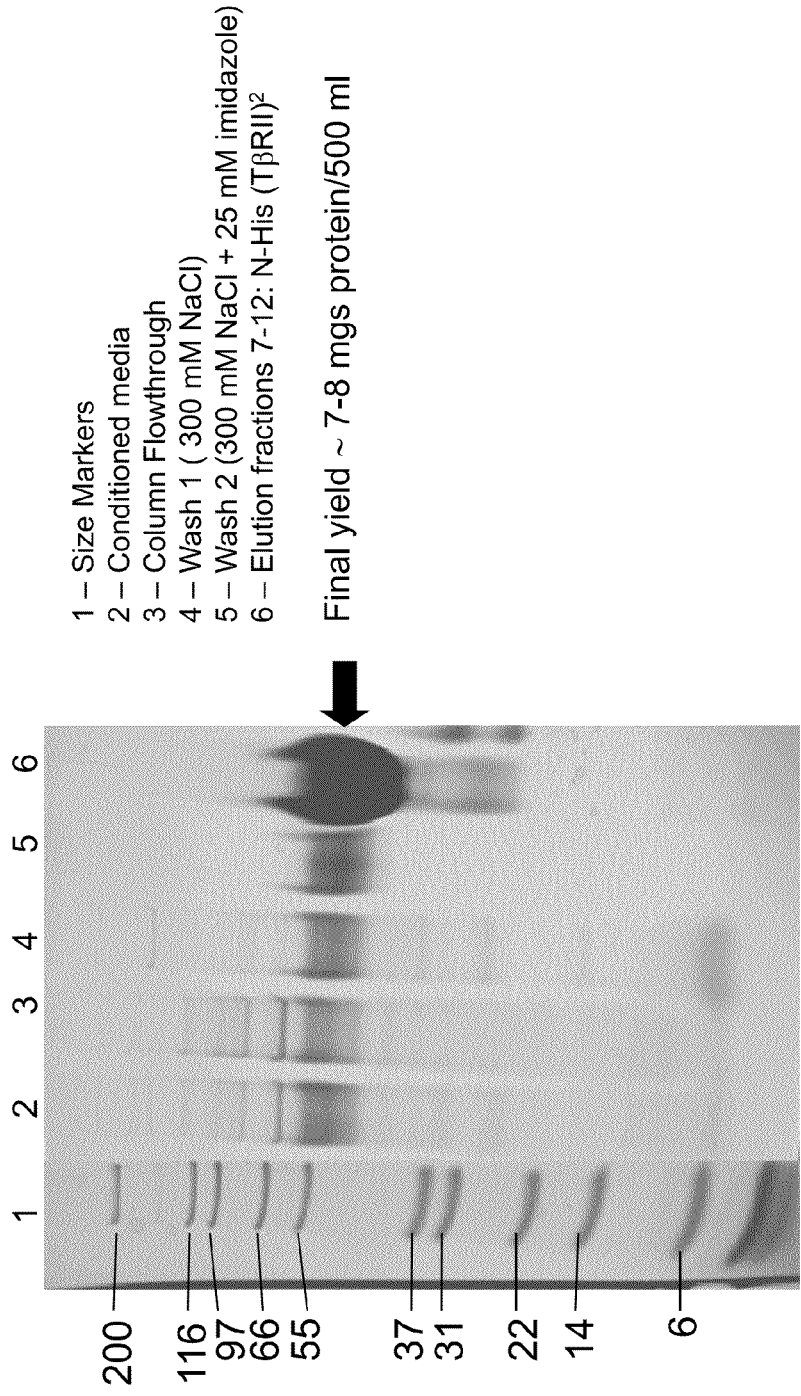
Figure 8. High level production and purification yield of N-His (TβRII)2 protein from 500 ml culture of transfected 293 cells.

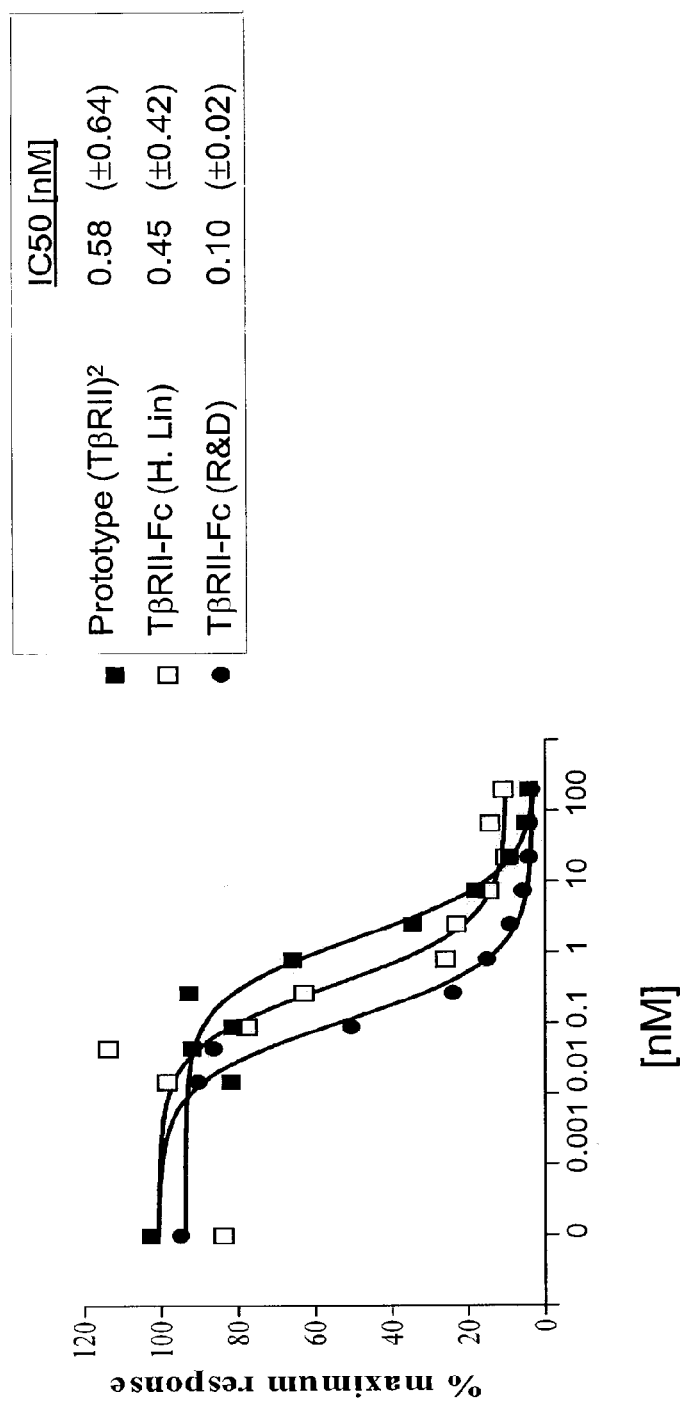
Figure 9A. Inhibition of TGF-β signaling in Mv1Lu luciferase reporter cells by prototype (TbRII)$^2$ compared to TβRII-Fc.

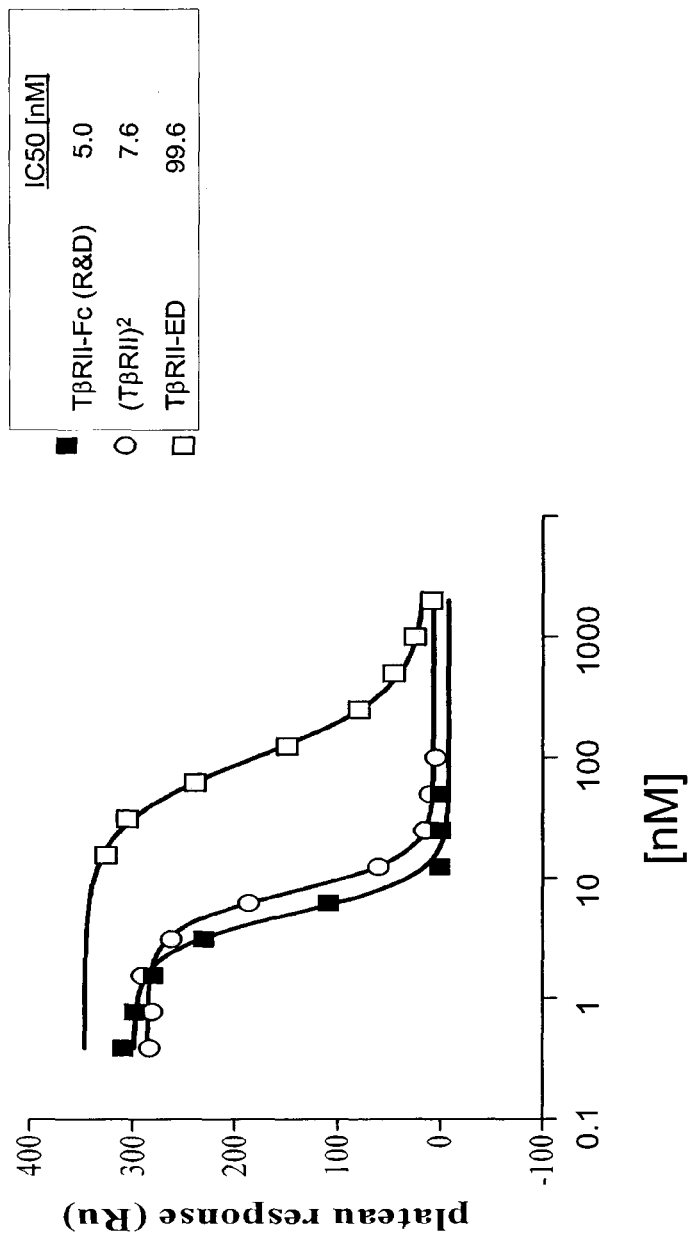
Figure 9B. SPR-based determination of trap binding of TGF-β in solution by prototype (TβRII)² and TβRII-Fc compared to monomeric TβRII-ED.

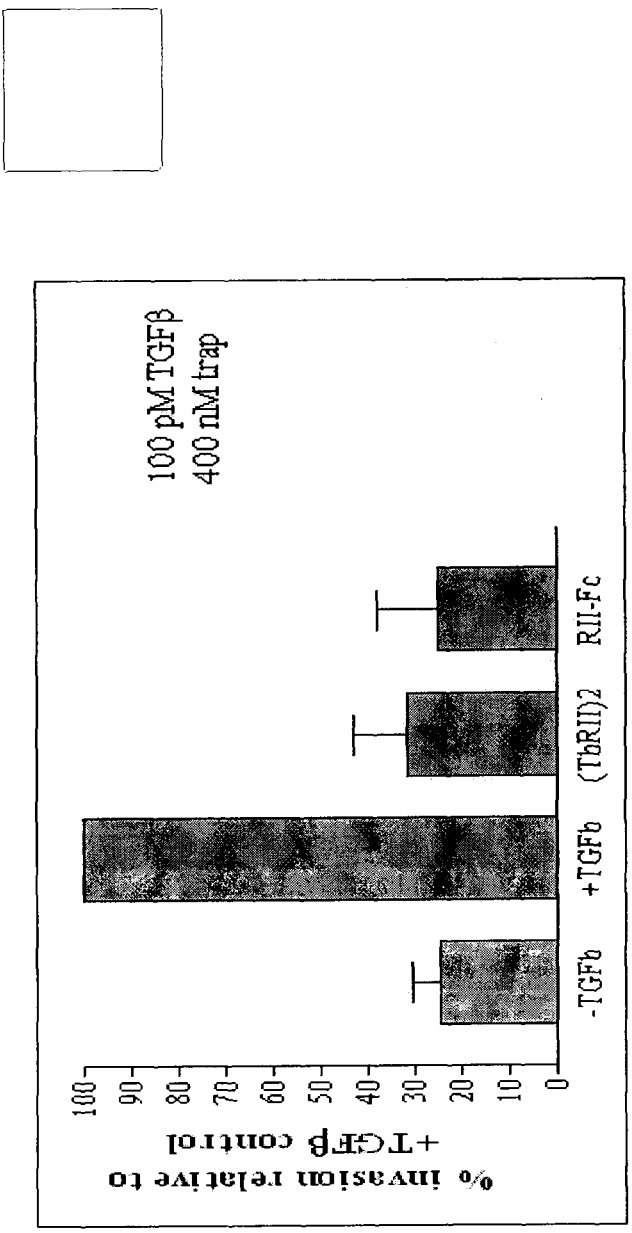
Figure 9C. Inhibition of TGFβ1-induced 4T1 cell invasion *in vitro* by prototype (TβRII)² and TβRII-Fc traps.

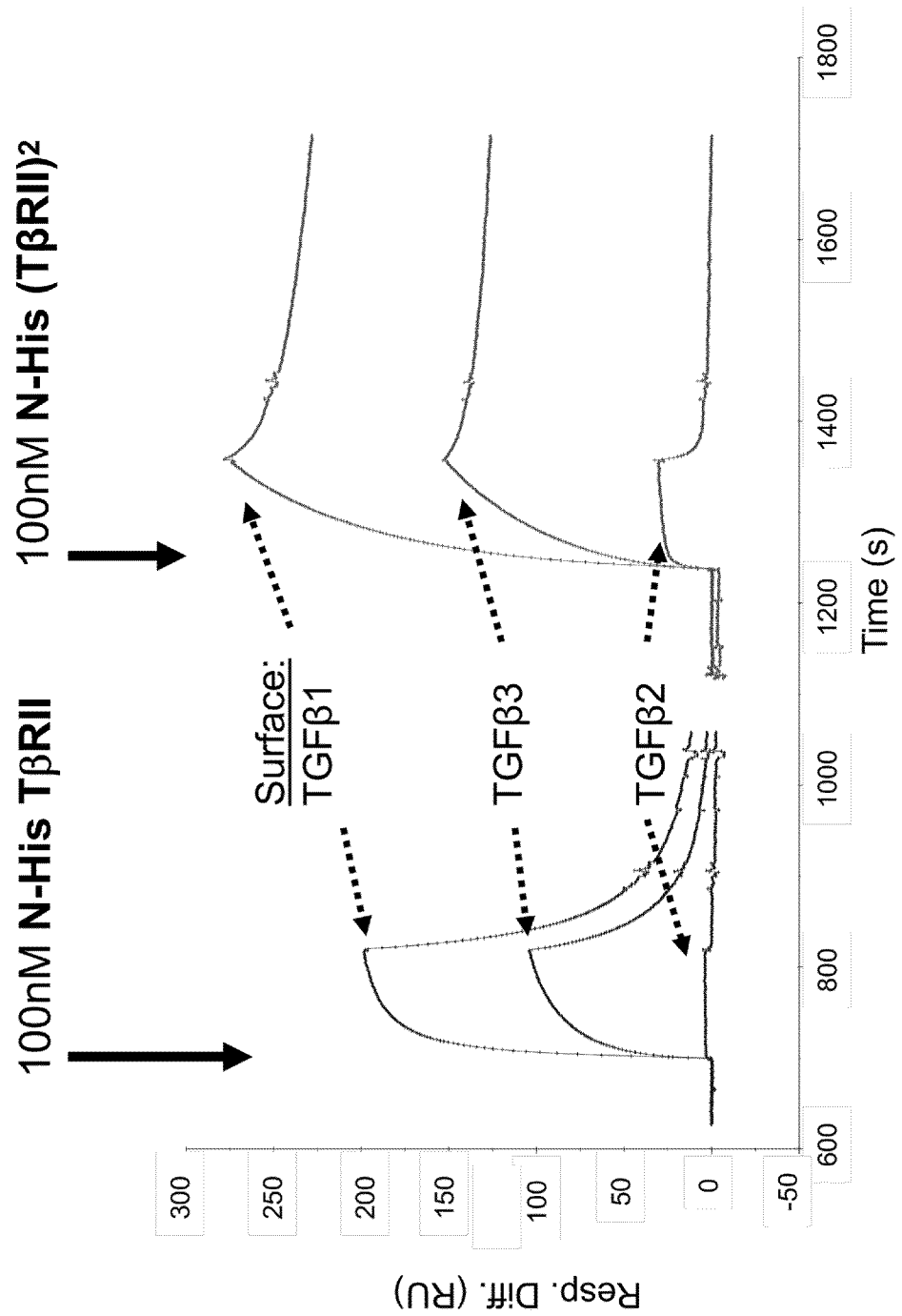
Figure 10A. Biacore sensogram showing direct binding of N-His (TβRII)² and monomeric N-His TβRII to different isoforms of TGF-β.

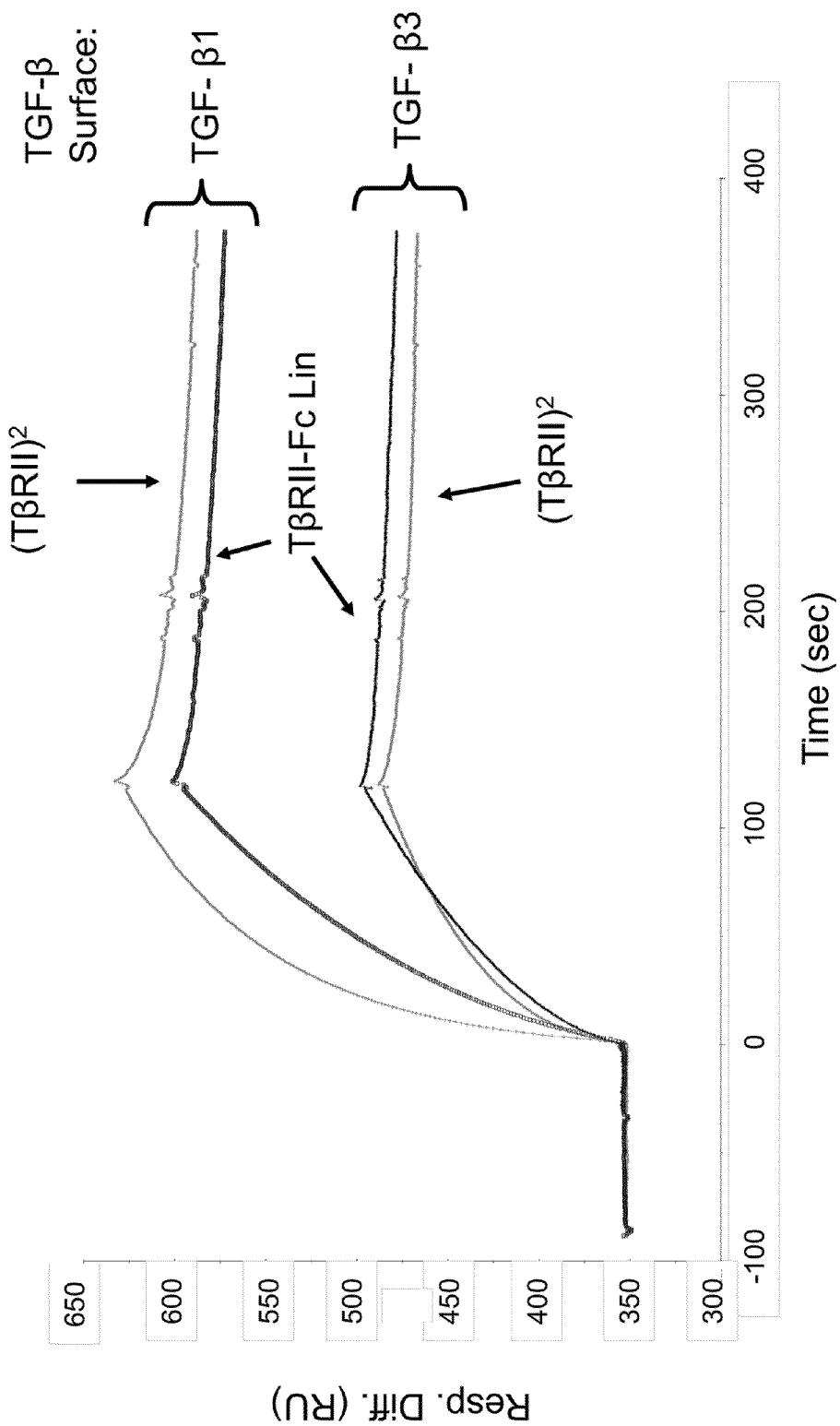
Figure 10B. Comparison of 100 nM N-His (TβRII)² and TβRII-Fc binding to 500 RUs each of TGF-β1 or TGF-β3

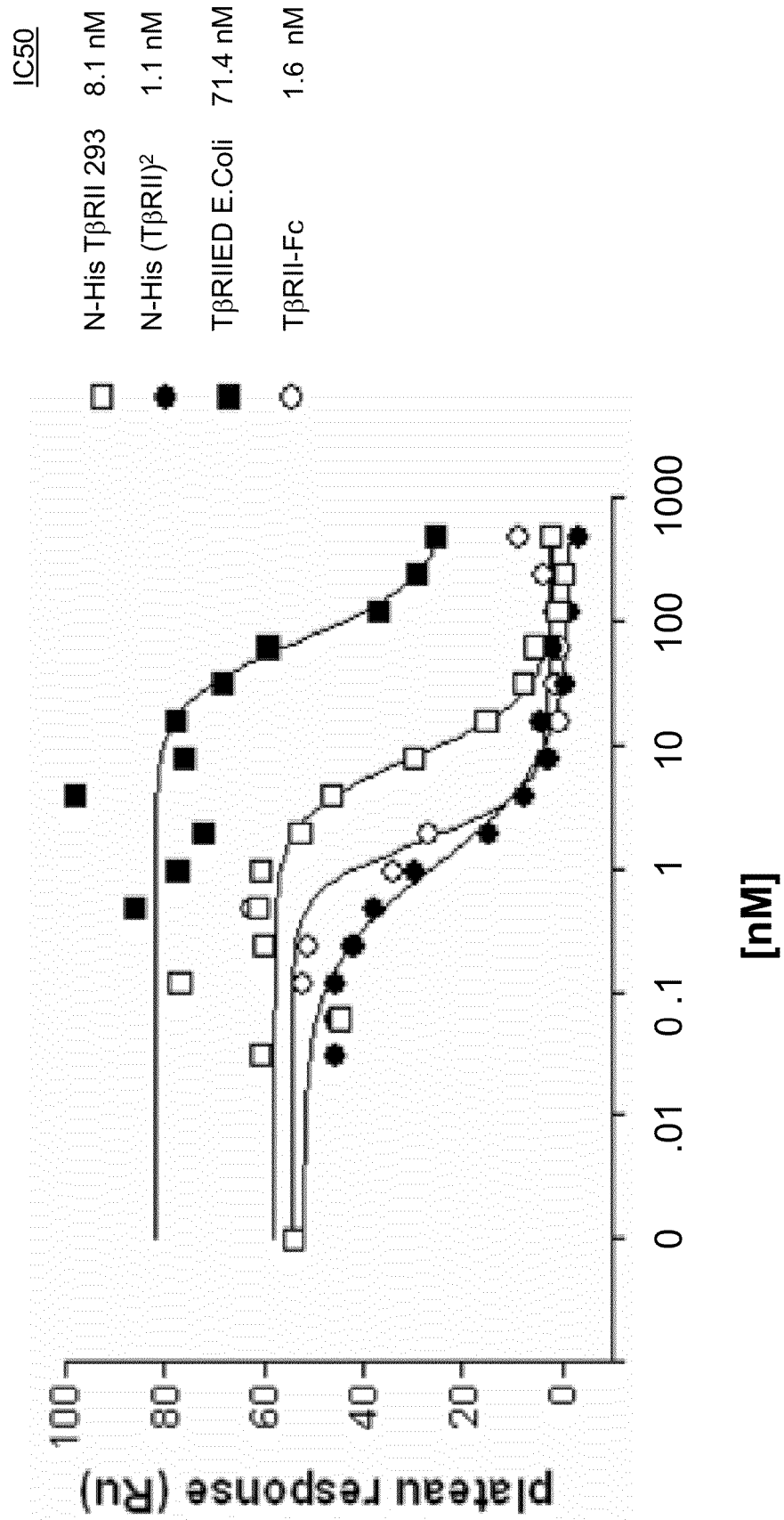
Figure 10C. SPR-based determination of IC50 for trap binding of TGF-β1 (5 nM) in solution.

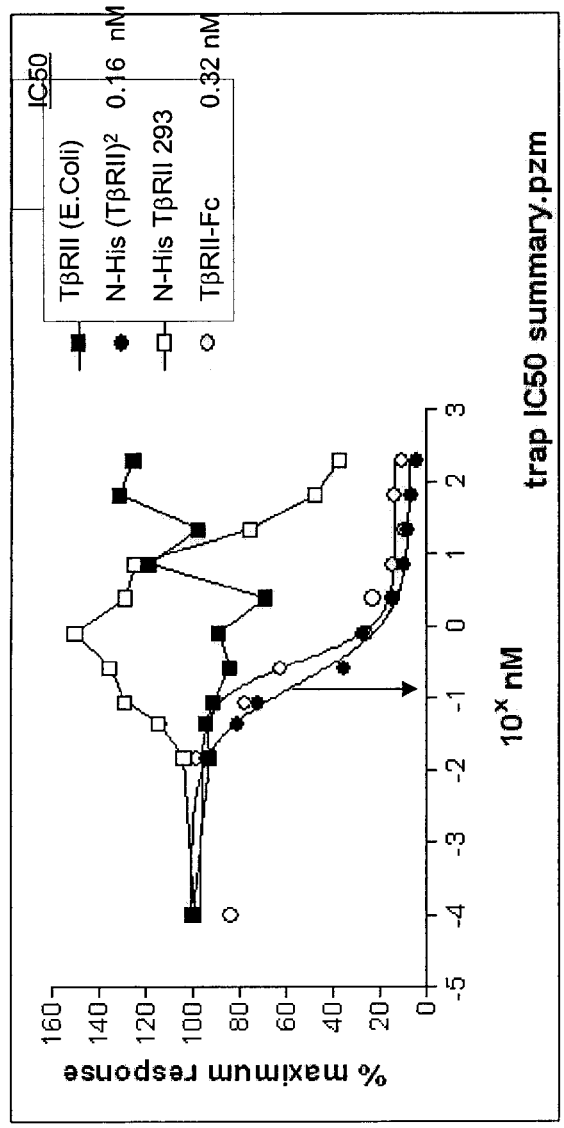
Figure 10D. Efficient inhibition of TGF-β signaling in Mv1Lu luciferase reporter cells by N-His (TbRII)² and TβRII-Fc compared to poor inhibition by monomeric TβRII (293 cell-produced and E-Coli-produced).

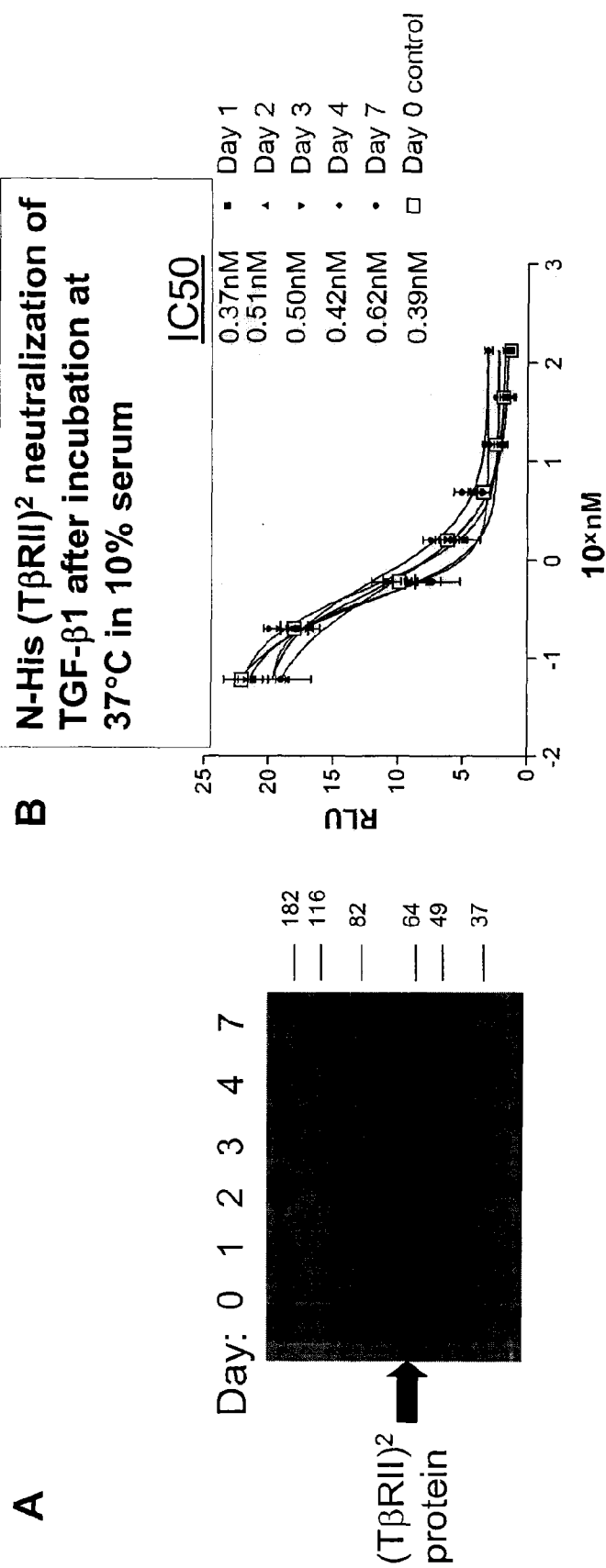
Figure 11. N-His (TβRII)² exhibits long-term stability and activity in 10% serum at 37°C

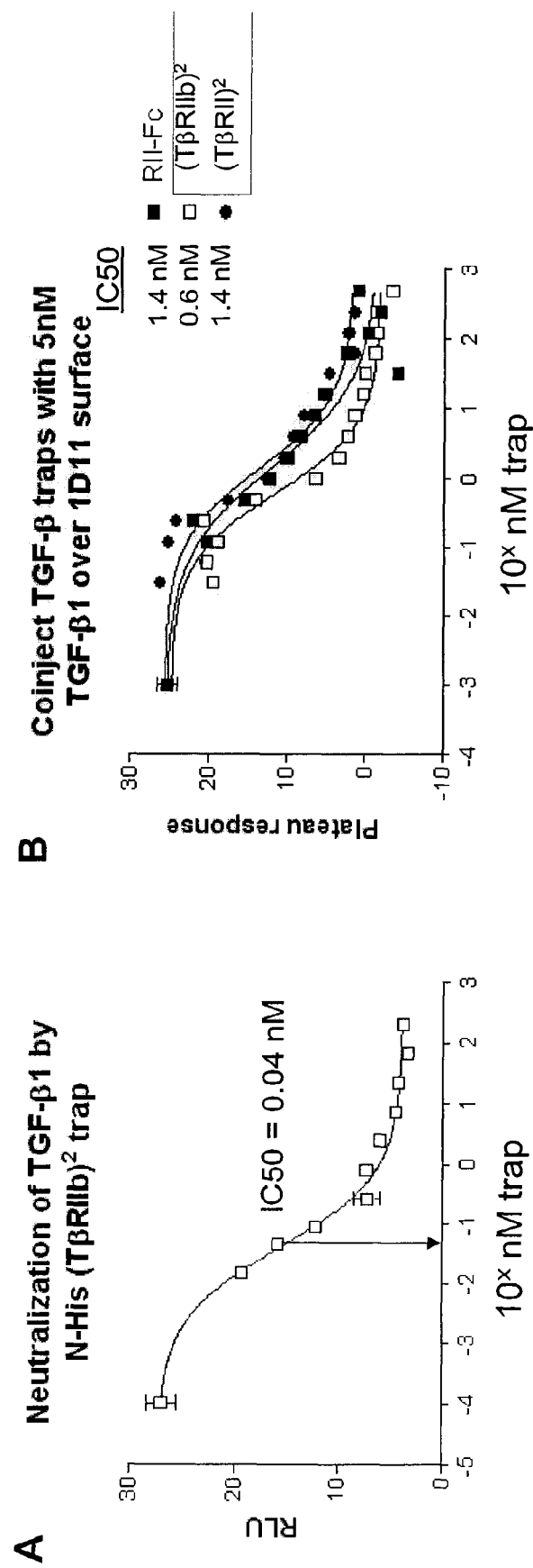
Figure 12. Efficient neutralization of TGF-β1 (A) and binding of TGF-β1 in solution (B) by (TβRIIb)² trap having 60 amino acid linker.

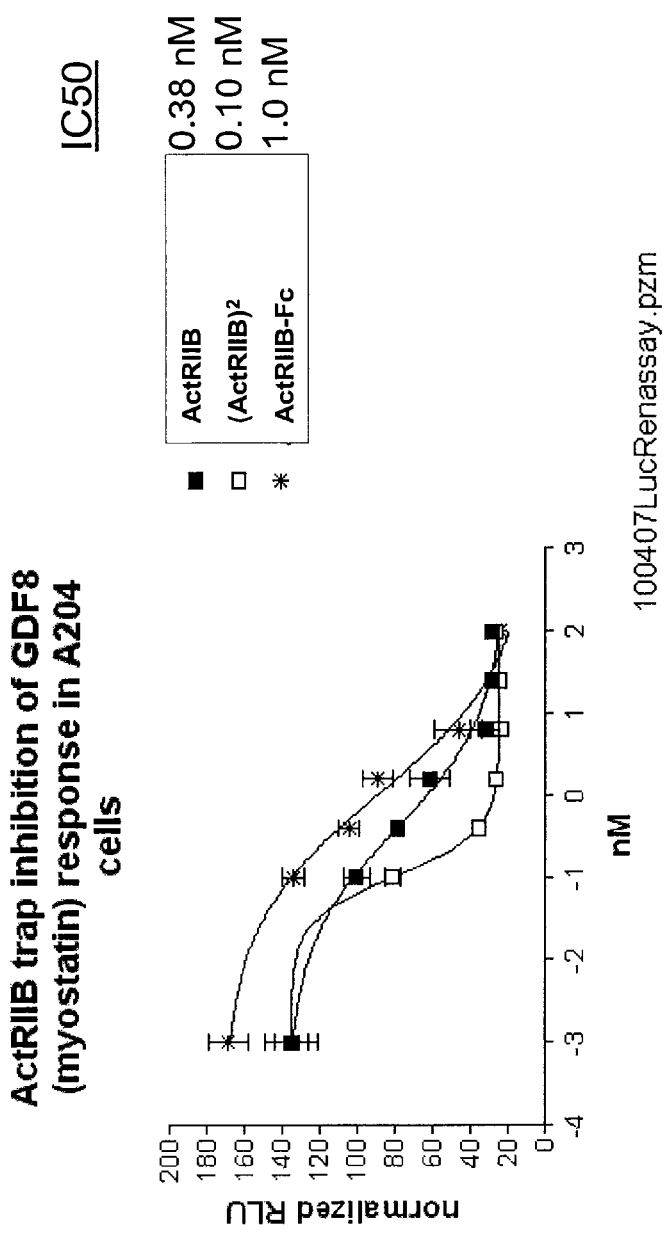
Figure 13. Efficient inhibition of Myostatin signaling in A204 cells by (ActRIIB)² trap compared to the less potent inhibition of ActRIIB-Fc and monomeric ActRIIB.

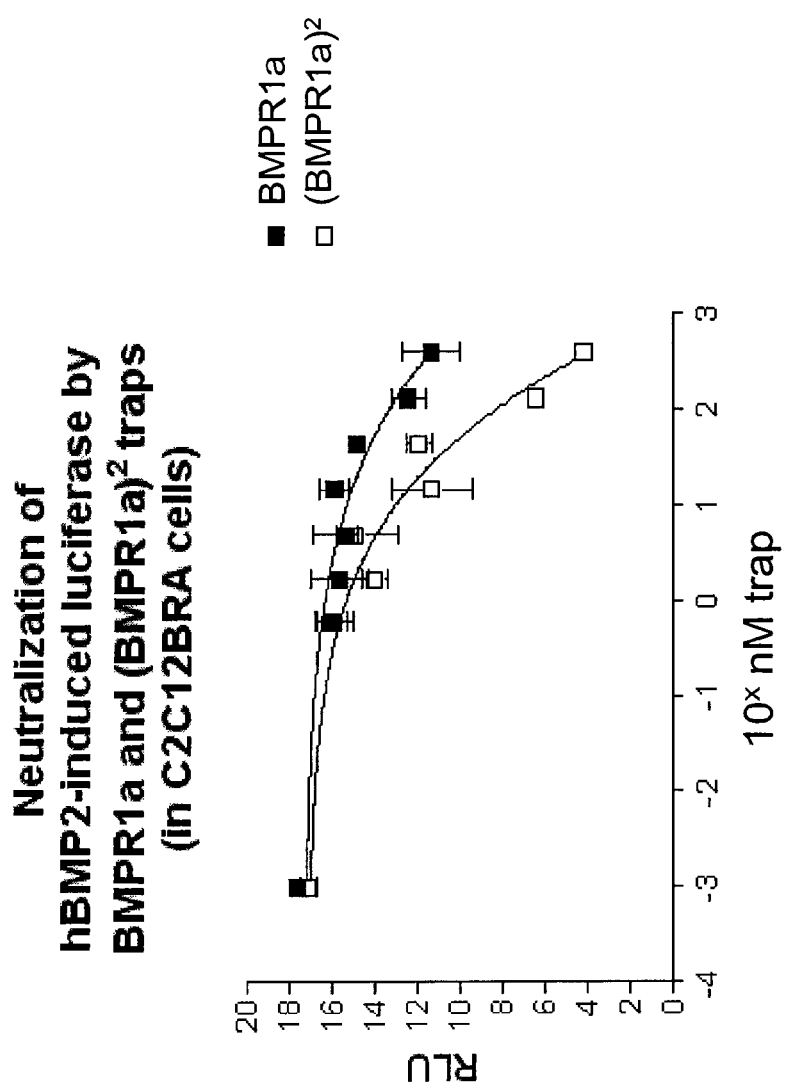
Figure 14. Bivalent (BMPR1a)² trap is more potent than monovalent BMPR1a trap for neutralization of BMP2.

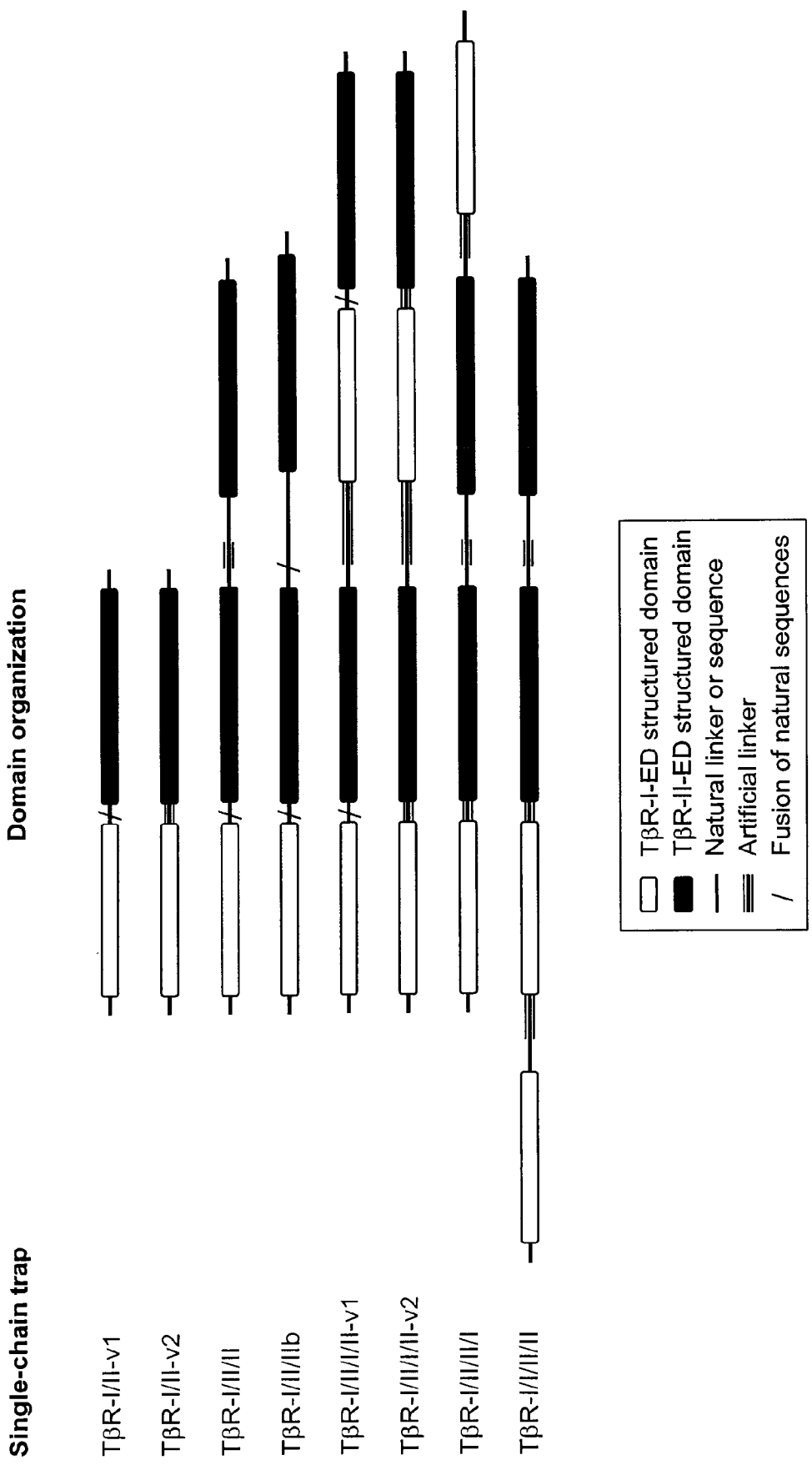
Figure 15A. Schematic diagrams exemplifying in-line fusions of receptor ectodomains leading to heterovalent single-chain traps of TGF-β-superfamily growth factors.

Figure 15B Part 1. Amino-acid sequences exemplifying heterovalent single-chain traps of TGF-β-superfamily growth factors, and corresponding to the domain organization diagrams depicted in panel (15A).

TβR-I/II-v1
SEQ ID NO 75

*AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF*
CDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD

TβR-I/II-v2
SEQ ID NO 76

*AALLPGATALQCFCHLCTKDNFTCVTDGLCFVSVTETTDKVIHNSMCIAEIDLIPRDRPFVCAPSSKTGSVTTTYCCNQDHCNKIELGGGGGNGAVKFPQLCKF*
CDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD

TβR-I/II/II
SEQ ID NO 77

*AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF*
CDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD
*GGGSGGGSGGGSI*PPHVQKSVNNDMIVTDNNGAVKFPQLCKFCDVRFSTCDNQKSCMSNCSITSICEKPQEVCVAVWRKNDENITLETVCHDPKLPYHDFILEDAA
SPKCIMKEKKKPGETFFMCSCSSDECNDNIIFSEEYNTSNPD

TβR-I/II/IIb
SEQ ID NO 78

*AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF*
CDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD
IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYNTSNPD

TβR-I/II/II-v1
SEQ ID NO 79

*AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF*
CDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDHC
*GGGSGGGSGGGSGGGSGGGSGGGSALQ*CFCHLCTKDNFCVTDGLCFVSVTETTDKVIHNSMCIAEIDLIPRDRPFVCAPSSKTGSVTTTYCCNQDHC
*NKIELPTTV*TDNNGAVKFPQLCKFCDVRFSTCDNQKSCMSNCSITSICEKPQEVCVAVWRKNDENITLETVCHDPKLPYHDFILEDAASPKCIMKEKKKPGETFFM
CSCSSDECNDNIIFSEEYNTSNPD

Key: underlined: natural linker or sequence; *underlined-italics*: artificial linker; bold: TβR-II-ED structured domain; *bold-italics*: TβR-I-ED structured domain; regular: unstructured region of TβR-II-ED that becomes structured in the ternary complex TβR-I/TβR-II/TGF-β [Groppe et al. 2008].

Figure 15B Part 2. Amino-acid sequences exemplifying heterovalent single-chain traps of TGF-β-superfamily growth factors, and corresponding to the domain organization diagrams depicted in panel (15A).

TβR-I/II/II-v2
SEQ ID NO 80

AALLPGATALQCFCHLCTKDNFTCVTDGLCFVSVTETTDKVIHNSMCIAEIDLIPRDRPFVCAPSSKTGSVTTTYCCNQDHCNKIELGGGGGGNGAVKFPQLCKF
CDVRFSTCDNQKSCMSNCSITSICEKPQEVCVAVWRKNDENITLETVCHDPKLPYHDFILEDAASPKCIMKEKKPGETFFMCSCSSDECNDNIIFSEEYNTSNPD
GGGSGGGS

US 8,734,760 B2

1

ANTAGONISTS OF LIGANDS AND USES THEREOF

This application is a divisional application of U.S. application Ser. No. 12/450,226 filed Dec. 22, 2009, which is a national entry of International Patent Application PCT/CA2008/000547 filed Mar. 19, 2008 which claims priority from U.S. Provisional Application No. 60/907,059 filed Mar. 19, 2007.

FIELD OF INVENTION

The invention relates to the field of antagonists and, more specifically, to polypeptide antagonists capable of use as single chain multivalent ligand traps.

BACKGROUND OF INVENTION

Many undesirable biological processes occur via ligand binding to cell surface receptors. Thus, it is sometimes desirable to have compounds and methods to reduce or modulate such binding.

The TGF-β superfamily includes a number of ligands of biological significance.

TGF-β and Activin play critical pathogenic roles in many diseases including the progression of cancer and uncontrolled fibrosis and scarring of tissues, e.g. kidney, lung and liver fibrotic diseases. Furthermore, Myostatin/GDF8 is another ligand which is related to Activin and which shares binding to the same Type II receptor (ActivinRIIb). Myostatin is a powerful inhibitor of skeletal muscle growth and is a validated therapeutic target for muscle wasting diseases such as muscular dystrophy. Bone morphogenetic proteins (BMP), which are other ligands in the TGF-β family, have been implicated in cardiovascular diseases. For example, high levels of both BMP2 and BMP4 have been found in calcified atherosclerotic plaques and diseased aortic valves.

Principal agents that target these ligands are ligand traps/antagonists that bind and sequester ligand. Two examples are: 1) anti-ligand antibodies and 2) soluble receptor ectodomains.

Efforts have been made to identify methods to reduce ligand binding by trapping ligand and preventing its interaction with the cell surface receptors. Inhibition of certain ligands has been reported using anti-ligand antibodies that trap and neutralize the ligand directly. For therapeutic and diagnostic applications, however, antibodies are problematic, particularly due to issues arising from their immunogenicity (and the danger of adverse immune response in patients) and their large size (restricting their ability to reach targets outside the bloodstream).

Soluble versions of receptor ectodomains antagonize ligands directly by binding to them and preventing them from interacting with cell surface receptors. In the case of TGF-β, in animal models, expression of a TGF-β receptor type II (TβRII) ectodomain (ED) partially restored host immunity and promoted tumor clearance, indicating that receptor ectodomain-mediated neutralization of TGF-β inhibits tumor progression. It has been shown, however, that the efficacy of monovalent TβRII to antagonize TGF-β is less than could be desired. Attempts to overcome this led to the production of an artificially dimerized form of versions of TβRII-ED, dimerized, via fusion to either coiled-coil domains or the Fc domain of IgG. This dimerization improved the antagonist effect.

Bivalent receptor-based traps/neutralizers that antagonize multimeric ligand activity have the potential to act as therapeutic or diagnostic (imaging or non-imaging) agents for diseases/disorders caused by over-production/activity of the target ligand. It has been demonstrated that non-covalent dimerization of TβRII-ED (for example, via fusion to heterodimerizing coil strands (coiled-coil TβRII-ED)), greatly enhances the antagonist potency of TβRII-ED (De Crescenzo et al., 2004, J. Biol. Chem. 279: 26013).

A significant disadvantage of the coiled-coil fused dimer is that the non-covalent nature of the dimerization domain limits its potency, i.e. it dissociates at low concentrations such that a large portion of the coil-fused receptor ectodomain will be acting as a monomer rather than a dimer. Use of the Fc domain of IgG provides a covalent interaction, but at the cost of large size and increased probability of immunogenicity.

BRIEF DESCRIPTION OF THE DRAWINGS

FIG. 1A. Depicts embodiments of amino-acid sequences corresponding to intrinsically unstructured regions in the extracellular portions of select TGF-β-superfamily receptors.

FIG. 1B. Depicts embodiments of amino-acid sequences corresponding to structured ligand-binding domain regions in the extracellular portions of select TGF-β-superfamily receptors.

FIG. 2A. Depicts examples of embodiments of in-line fused receptor ectodomains as homo-bivalent single-chain traps of several TGF-β-family growth factors. The "I" sign indicates the point of fusion.

FIG. 2B. Depicts examples of sequences corresponding to natural linkers of embodiments of homo-bivalent single-chain traps resulting from fusion of the entire extracellular portions of select TGF-β-superfamily receptors.

FIG. 2C. Depicts examples of sequences corresponding to embodiments of artificial linkers for homo-bivalent single-chain traps at varying sequence identity to natural linker sequences.

FIG. 2D. Depicts examples of sequences corresponding to varying the linker length for embodiments of homo-bivalent single-chain traps by deleting or repeating of natural sequences, or by inserting of artificial sequences, into the natural linker sequence.

FIG. 3. Depicts an illustration of an embodiment of the (TβR-II)$^2$ single-chain trap construct on a three-dimensional molecular mechanical model of the (TβR-II)$^2$ single-chain trap bound to the TGF-β3 growth factor. Two 90°-rotated views are provided.

FIG. 4. Depicts diagrams relating to the feasibility of specific embodiments of trap constructs with natural linkers from three-dimensional structural models. Shown are molecular mechanics energy-minimized natural linkers for embodiments of (TβR-II)$^2$, (ActR-IIb)$^2$ and (BMPR-Ia)$^2$ homo-bivalent single-chain traps in complex with the TGF-β3, Activin and BMP-2 growth factors, respectively. Each growth factor covalent dimer is rendered in gray. Each single-chain trap is rendered in black, and consists of two folded binding domains and an intervening unstructured linker. Each dot indicates the point of fusion in the linker region between two receptor ectodomains to generate the single-chain trap. Arrowheads indicate polypeptide chain direction in the trap's linker. Two 90°-rotated views are provided for each complex.

FIG. 5A. Depicts molecular dynamics (MD) model for an embodiment of the (TβR-II)$^2$ homo-bivalent single-chain trap bound to the TGF-β3 growth factor (right images). An initial model with energy-minimized linker and with ligand-binding domains in crystallographic positions bound onto the growth factor is also shown for reference (left images, see also FIGS. 3 and 4). The single-chain trap is rendered in black and the growth factor covalent dimer is rendered in gray. Ten time-averaged structures (each over 1 ns) covering 10 ns timeframe of MD simulation are overlaid. Two 90°-rotated views are provided FIG. 5B. is a graphical representation of per residue root-mean-square (RMS) fluctuations of an embodiment of the (TβRII)²/TGF-β3 complex, time-averaged over the last 10 ns of MD simulation.

FIG. 5C. is a graphical representation of solvated Interaction Energy (SIE) between an embodiment of a single-chain (TβRII)² trap and the TGF-β3 ligand over the last 10 ns of MD simulation of their complex, with an average value of −25.4 kcal/mol.

FIG. 6. Depicts a schematic of embodiments of prototype (TβRII)² and modified N-His (TβRII)² traps.

FIG. 7A. Depicts surface plasmon resonance (SPR)-based biosensor (Biacore™) sensograms showing an embodiment of a prototype (TβRII)² (in diluted conditioned media from different % transfections) binding to surface-immobilized TGF-β3 ligand.

FIG. 7B. Depicts surface plasmon resonance sensograms comparing binding of embodiments of bivalent prototype (TβRII)², bivalent TβRII-Fc and monovalent TβRII to 270 RUs surface-immobilized TGF-β3 ligand.

FIG. 8. Is a photographic depiction of a gel showing high level production and purification yield of an embodiment of N-His (TβRII)² protein from 500 ml culture of transfected 293 cells.

FIG. 9A. Is a graphical depiction of inhibition of TGF-β signaling in Mv1 Lu luciferase reporter cells by an embodiment of prototype (TβRII)² compared to TβRII-Fc.

FIG. 9B. Is a graphical depiction of SPR-based determination of trap binding of TGF-β in solution by an embodiment of prototype (TβRII)² and TβRII-Fc compared to monomeric TβRII-ED.

FIG. 9C. Is a graphical depiction of inhibition of TGFβ1-induced 4T1 cell invasion in vitro by an embodiment of prototype (TβRII)² and TβRII-Fc traps.

FIG. 10A. Is a Biacore™ sensogram showing direct binding of embodiments of N-His (TβRII)² and monomeric N-His TβRII to different isoforms of TGF-β.

FIG. 10B. Is a graphical depiction of a Biacore™ comparison of performance of embodiments of 100 nM N-His (TβRII)² and TβRII-Fc to bind to 500 RUs each of TGF-β1 or TGF-β3

FIG. 10C. Is a graphical depiction of SPR-based determination of IC50 for trap binding to TGF-β1 (5 nM) in solution. The graph shows efficient binding of TGF-β1 by an embodiment of a N-His (TβRII)² trap and TβRII-Fc trap versus reduced binding by monomeric TβRII (293 cell-produced or E. coli-produced).

FIG. 10D. Is a graphical depiction showing efficient inhibition of TGF-β signaling in Mv1Lu luciferase reporter cells by an embodiment of N-His (TβRII)² and TβRII-Fc compared to poor inhibition by monomeric TβRII (293 cell-produced and E-Coli-produced).

FIG. 11. (A) is a photographic depiction and (B) is a graphical depiction of results showing that an embodiment of N-His (TβRII)² exhibits long-term stability and activity in 10% serum at 37° C.

FIG. 12. Provides graphical depictions showing efficient neutralization of TGF-β1 (A) and binding of TGF-β1 in solution (B) by an embodiment of a (TβRII)² trap (ligand binding agent) having a 60 amino acid linker.

FIG. 13. Is a graphical depiction showing efficient inhibition of Myostatin signaling in A204 cells by an embodiment of an (ActRIIB)² trap (ligand binding agent) compared to the less potent inhibition of ActRIIB-Fc and monomeric ActRIIB.

FIG. 14. Is a graphical depiction of results showing that an embodiment of a bivalent (BMPR1a)² trap (ligand binding agent) is more potent than monovalent BMPR1a trap for neutralization of BMP2.

FIG. 15A. Provides schematic diagrams exemplifying embodiments of in-line fusions of receptor ectodomains leading to embodiments of heterovalent single-chain traps of TGF-β-superfamily growth factors.

FIG. 15B parts 1 and 2. Depict embodiments of amino-acid sequences exemplifying embodiments of heterovalent single-chain traps (ligand binding agents) of TGF-β-superfamily growth factors, and corresponding to the domain organization diagrams depicted in FIG. 15A.

SUMMARY OF INVENTION

The invention relates to ligand binding agents capable of permitting modulation of cellular response to members of the TGF-β superfamily by binding one or more members of the TGF-β superfamily and preventing interaction with cellular receptors, and methods of designing and using such agents. The ligand binding agents taught herein are preferably single chain multivalent ligand binding agents. However, it would be possible to link such single-chain constructs to other uni- or multivalent molecules and/or to combine two or more such single chain traps using multimerization domains known in the art (e.g. coiled-coil domains, Fc domains, pentabodies) to form a multimeric trap if so desired and any such trap having a multivalent single chain portion falls within the scope of the present invention.

In an embodiment of the invention there is provided methods and processes to engineer multivalent receptor ectodomains using a single-chain approach.

The ligand binding agents of the invention are preferably multivalent ligand traps, having at least two binding domains (bd) which recognize different sites on (or the same site of different portions of) the same member of the TGF-β superfamily. The binding domains may be modified, for example to facilitate purification, so long as such modifications do not reduce binding affinity to unacceptable levels.

The binding domains (bd) of the ligand traps are preferably joined by a flexible polypeptide linker region. This linker should preferably include an unstructured amino acid sequence which in some embodiments is be either the same as or derived from conservative modifications to the sequence of a natural unstructured region in the extracellular portion of the receptor for the ligand of interest or another receptor in the TGF-β superfamily. In other instances, such linkers may be entirely artificial in composition and origin but will contain amino acids selected to provide an unstructured flexible linker with a low likelihood of encountering electrostatic or steric hindrance complications when brought into close proximity to the ligand of interest.

In some instances, the linker will include regions to facilitate purification (e.g. His tags) or to facilitate the addition of cargo or accessory molecules. When such additions affect the unstructured nature of the linker or introduce potential electrostatic or steric concerns, appropriate increases to the linker length will be made to ensure that the two binding domains are able to bind their respective sites on the ligand. In light of the methods and teachings herein, such determinations could be made routinely by one skilled in the art.

In an embodiment of the invention there are provided ligand traps having the general Structure I:

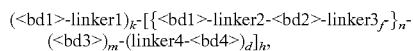

(<bd1>-linker1)$_k$-[{<bd1>-linker2-<bd2>-linker3$_f$}$_n$-(<bd3>)$_m$-(linker4-<bd4>)$_d$]$_h$, where:

n and h are independently greater than or equal to 1;

d, f, m and k are independently equal to or greater than zero;

bd1, bd2, bd3 and bd4 are polypeptide binding domains having an affinity for the same member of the TGF-β superfamily, with bd1, bd2, bd3, and bd4 being independently the same or different from each other; and, linker1, linker2, linker3 and linker4 are unstructured polypeptide sequences;

wherein the number of amino acids in each linker is determined independently and is greater than or equal to X/2.5; where, X equals the shortest linear distance between:

(a) the C-terminus of an isolated form of the binding domain that is located at the N-terminus of the linker and that is specifically bound to its ligand; and, (b) the N-terminus of an isolated form of the binding domain that is located at the C-terminus of the linker and that is specifically bound to its ligand.

As used herein "an isolated form" of a binding domain is a form of that binding domain acting as a monovalent monomer.

Subject to the constraints described herein, linkers 1, 2, 3, and 4 may be the same or different. In certain embodiments the linker is between 25 and 60 amino acids in length Also provided are nucleic acid sequences encoding such ligand traps.

Depending on the values selected for d, f, h, k, m, and n, the ligand trap structure may comprise a large number of repeating units in various combinations or may be a relatively simple structure such as Structure II <bd1>-linker-<bd2>.

In certain embodiments of the invention, the member of the TGF-β superfamily to which the binding domains (bd) have affinity is selected from the group consisting of: TGF-β1, TGF-β2, TGF-β3, activin βA, activin βB, activin βC, activin βE, bone morphogenic protein (BMP) 2, BMP 3, BMP4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin a, anti-Mullerian Hormone, Lefty 1, Lefty 2, arteman, Persephin and Neurturin.

In an embodiment of the invention there is provided a binding agent wherein one or more of bd1, bd2, bd3, and bd4 is selected from one of SEQ ID NO 43-48.

In an embodiment of the invention the binding agent comprises one or more of SEQ ID No 75 to 82.

In an embodiment of the invention the binding agent comprises one or more of SEQ ID NO 31-42 or 49-74 as a linker sequence.

The invention also provides a method of designing a multivalent binding agent useful in modulating responsiveness of a cell to a member of the TGF-β superfamily, said method comprising:

a) identifying a member of the TGF-β superfamily of interest;
b) obtaining two polypeptide binding domains having affinity for different sites on the member of the TGF-β superfamily member;

c) obtaining an unstructured polypeptide linker of at least a number of amino acids equal to (X/2.5) where X equals the shortest linear distance between:

(i) the C-terminus of an isolated form of the binding domain that is located at the N-terminus of the linker and that is specifically bound to its ligand; and, (ii) the N-terminus of an isolated form of the binding domain that is located at the C-terminus of the linker and that is specifically bound to its ligand; and, d) modelling the linker between the binding domains and carrying out molecular dynamics simulations to substantially minimize molecular mechanics energy and reduce steric and electrostatic incompatibility between the linker and the member of the TGF-β superfamily.

The design method can optionally be expanded to further include a step e) of producing a fusion protein comprising the two polypeptide binding domains joined by the unstructured polypeptide linker.

The ligand binding agents disclosed herein are also useful in purification of ligand, for example, by immobilization on an inert matrix on a solid support, on, for example, to nanoparticles to concentrate levels of ligand in a sample.

The invention also provides novel polypeptide sequences useful in a variety of applications. These sequences include SEQ ID NOs 53 to 74. Also provided are nucleic acid sequences encoding these polypeptide sequences.

Also provided is a method of modulating the response of a cell to TGF-β in its environment, said method comprising exposing the cell to a multivalent ligand trap comprising a ligand binding agent (ligand trap) disclosed herein.

In an embodiment of the invention there is provided a binding agent having the general structure V:

$R_3$ $R_4$ $R_5$ $R_6$ $R_7$ $R_8$ $R_9$ $R_1$-(<bd1>-linker1)$_k$-[{<bd1>-linker2-<bd2>-linker3$_f$}$_n$-(<bd3>)$_m$-(linker4-<bd4>)$_d$]$_h$-$R_2$ Wherein $R_1$, $R_2$, $R_3$, $R_4$, $R_5$, $R_6$, $R_7$, $R_8$, $R_9$, may be the same or different, may not be present and when present, may independently be one or more of a fusion protein for targeting, a single domain antibody, a radiotherapy agent, an imaging agent, a fluorescent dye, a fluorescent protein tag, a cytotoxic agent for chemotherapy a nano particle-based carrier, a polymer-conjugated to drug, nanocarrier or imaging agent, a stabilizing agent, a drug a nanocarrier and a dendrimer and a support for use in purification or concentration of ligand; and wherein bd1, bd2, bd3, bd4, linker1, linker2, linker3, linker4, k, f, n, m, d, and h are defined as in Structure I. In light of the disclosure herein, one skilled in the art can select suitable R-groups for diagnostic therapeutic or other applications.

In an embodiment of the invention there is provided an isolated polypeptide having at least 80%, 85%, 90%, 95%, 98%, 99% and 100% sequence identity to a natural unstructured region in the extracellular portion of a receptor for a member of the TGF-β superfamily and being substantially free of structured regions capable of specific binding to a member of the TGF-β superfamily. In some instances, this isolated polypeptide has at least 80%, 85%, 90%, 95%, 98%, 99% sequence identity to one or more of SEQ ID NO 31-42 and SEQ ID NOs 49-74.

In an embodiment of the invention there is provided a polypeptide comprising a region having at least 80%, 85%, 90%, 95%, 98%, 99% sequence identity to one or more of SEQ ID NOs 53-74 and SEQ ID NOs 82-118. In some instances this polypeptide has a region with at least 90%, 95%, 98%, 99% sequence identity to one or more of SEQ ID NOs 53-74.

In an embodiment of the invention there is provided a polypeptide having between 43% and 99% sequence identity to a naturally unstructured region in the ectodomain of a receptor for a member of the TGF-β superfamily.

In an embodiment of the invention there is provided a nucleic acid sequence encoding a polypeptide disclosed herein.

In an embodiment of the invention there is provided a method of modulating the response of a cell to a TGF-β superfamily member in its environment, said method comprising exposing the cell to a ligand binding agent disclosed herein.

In an embodiment of the invention there is provided a data storage medium comprising instructions for determining the minimum linker length when designing a ligand binding agent.

In an embodiment of the invention there is provided a data storage medium comprising a means for identifying acceptable minimal linker length when designing a ligand binding agent.

Linker length will be considered acceptable when it permits binding of binding domains located on each of the N- and C-termini of the linker to bind their natural binding sites on their natural ligand such that, with both binding domains so bound, the ligand is bound with a higher affinity than it would be bound by binding of only one of the binding domains.

BRIEF DESCRIPTION OF THE INVENTION

In an embodiment of the invention there is provided a single-chain non-naturally occurring polypeptide useful as a ligand binding agent. The ligand binding agent comprises structured ligand-binding domains (denoted bd) derived from or based on the extracellular portion of a natural receptor or receptors, joined by one or more polypeptide linkers. The ligand binding agent provides a multivalent binding agent and does not require fusion to any conventional dimerizing or multimerizing moieties such as coiled-coil domains of Fc domains in order to be multivalent.

In an embodiment of the invention, there is provided a multivalent binding agent with affinity for a member of the TGF-β superfamily, said agent comprising the general structure I:

(<bd1>-linker1)$_k$-[{<bd1>linker2-<bd2>-linker3}$_n$-(<bd3>)$_m$-(linker4-<bd4>)$_d$]$_h$, where:
n and h are independently greater than or equal to 1;
d, f, m and k are independently equal to or greater than zero;
bd1, bd2, bd3 and bd4 are polypeptide binding domains having an affinity for the same member of the TGF-β superfamily, with bd1, bd2, bd3 and bd4 being independently the same or different from each other; and,
linker1, linker2, linker3 and linker4 are unstructured polypeptide sequences; wherein the number of amino acids in each linker is determined independently and is greater than or equal to X/2.5; where,
X equals the shortest linear distance between:
(a) the C-terminus of an isolated form of the binding domain that is located at the N-terminus of the linker and that is specifically bound to its ligand; and,
(b) the N-terminus of an isolated form of the binding domain that is located at the C-terminus of the linker and that is specifically bound to its ligand.

As used herein "an isolated form" of a binding domain is a form of that binding domain acting as a monovalent monomer.

The length of the linker is considered to be the number of amino acids between:
(a) the C-terminal main chain carbon atom of the binding domain located at the linker's N-terminal end; and
(b) the N-terminal main-chain nitrogen atom of binding domain located at the linker's C-terminal end.

Non-limiting examples of useful linkers are found in the amino acid sequences in SEQ ID NOs 53 to 74 which should be read conventionally with the N-terminus on the left and the C-terminus on the right, and in corresponding reverse sequences having the same amino acids but wherein the C-terminus is on the left and the N-terminus is on the right as the sequences are written in full. In some embodiments, such reverse sequences will preferably be produced using D-amino acids. Where immunogencity is of concern, it will generally be desired to screen such reverse sequences for immunogenicity at an early stage. (For examples of reverse sequences, see SEQ ID NOs 82-118). All amino acids sequences in this document are written N-terminus to C-terminus unless otherwise noted. All sequences disclosed herein except SEQ ID NOs 82-118 are disclosed as using L-amino acids and the use of a D-amino acid is considered a variant affecting the percent sequence identity to the sequences as stated.

In an embodiment of the invention, the ligand binding agent has the general Structure II:

<bd1>-linker2-<bd2>.

In an embodiment of the invention, the ligand binding agent has the general Structure III <bd1>-(linker2-<bd2>)$_n$.

In an embodiment of the invention, the polypeptide has the general Structure IV:

([bd1]-[linker1]-[bd1])$_f$-[linker2]-([bd2]-[linker3]-[bd3])$_g$, when f and g are greater than or equal to one.

In an embodiment where bd2 and bd3 are the same, and f and g are the same number, this can result in a substantially mirror symmetric structure around linker 2, subject to differences in the linkers. In instances where bd3 is different from bd2 and and/or where f and g are different numbers, different structures will be produced. It is within the capacity of one of ordinary skill in the art to select suitable binding domains, linkers, and repeat frequencies in light of the disclosure herein.

In some instances, the binding domain region of the single-chain polypeptide will be selected for its ability to bind a growth-factor ligand having a covalently-stabilized dimeric quaternary structure, and may be selected from a list of growth factors from within the TGF-β family, e.g., transforming growth factor beta (TGF-β, bone morphogenetic protein (BMP), activin, myostatin, and including their naturally occurring isoforms.

In some instances, the polypeptide is designed to bind simultaneously to equivalent but spatially distinct sites on a multimeric ligand. As used herein "multimeric" includes dimeric, trimeric, and greater numbers of units, and "multivalent" includes bivalent, trivalent, and greater numbers of binding domains.

In some instances, the linker is independently selected to have varying degrees of sequence identity to naturally occurring unstructured amino acid sequences found in the native receptor sequence in the regions flanking the ligand binding domain, for example 70%, 80%, 90%, 95%, 98%, 99% or 100% sequence identity, whereas for entirely artificial linkers (e.g. poly-Gly or poly-Ser linkers, sequence identity will be even lower. Examples of linker sequences of varying degree of identity to the natural receptor sequence are given in FIG. 2C and SEQ ID NOs 82-118 (Table II).

In some instances, the number of amino acid residues in the linker of either natural or artificial origin is selected to be equal to or greater than the minimum required distance for simultaneous (bridged) binding to two binding sites on the growth factor to be bound by the relevant binding domains. An example of an embodiment of such a determination is given in the section "Feasibility assessment procedure for designed single-chain bivalent traps". Examples of natural and artificial linker sequences of varying length are given in FIG. 2D and SEQ ID NOs 82-118. In some instances, linker length is between 18-80 a.a., 25-60 a.a., 35-45 a.a.

In some instances, the overall molecular mass of bivalent agents disclosed herein before glycosylation is between about 29 kDa and 37 kDa, and the overall mass following typical glycosylation is between about 40 kDa and 60 kDa. Thus, there is provided herein, multivalent ligand traps having a pre-glycosylation size of between about 12 kDa and 19 kDa per binding domain.

The ligand traps disclosed herein will generally have a lower molecular mass than comparable multimeric ligand traps constructed using known multimerization domains.

Example of Selected Ligand Trap Sizes

| Agent | Predicted for protein | Actual (with glycosylation) based on SDS-PAGE |
|---|---|---|
| (TβRII)$^2$ | 34 kDa | 50-60 kDa |
| (TβRIIb)$^2$ | 37 kDa | 50-60 kDa |
| (ActRIIB)$^2$ | 30 kDa | 50-60 kDa |
| (BMPR1a)$^2$ | 29 kDa | 40-50 kDa |
| RIIEcoil + RIIKcoil | | 37 Kd + 40 kDa = 77 kDa |
| TβRII-Fc | | 60 Kd + 60 kDa = 120 kDa |

Polypeptides of the invention can be useful as therapeutic agents that neutralize the action of disease-associated covalently-stabilized dimeric ligands such as growth factors. They may also have commercial potential for use as diagnostic agents to detect the presence of disease-associated covalently-stabilized dimeric ligands such as growth factors in imaging and non-imaging diagnostic applications. They can also be useful in the purification and/or concentration or segregation of ligand in vitro.

DETAILED DESCRIPTION OF INVENTION

Although the invention is described with reference to specific examples, it will be understood that it is not so limited.

Experiment #1: Design Strategy of Simile-Chain Bivalent Traps for TGF-β-Family Ligands 1. Single-chain recombinant traps were designed against growth factors that belong to the transforming growth factor TGF-β superfamily of cysteine-knot cytokines according to SCOP (Andreeva et al., 2008, Nucl. Acid Res. 36: D419) and Pfam (Finn et al., 2006, Nucl Acid Res. 34: D247) structural classifications. More specifically, these growth factors including, for example, TGF-βs, activins and BMPs, share the same 3D architecture and form covalent disulfide-linked homodimers. The method disclosed herein is applicable to all members of the TGF-βsuperfamily, including TGF-β1, -β2, -β3; activin βA, βB, βC, βE; bone morphogenetic proteins (BMP) 2-15; growth differentiation factors (GDF) 1, 3, 8 (myostatin), 9 and 15; Nodal; Inhibin α; anti-Mullerian hormone (AMH); Lefty 1 and 2; Arteman, Persephin and Neurturin.

2. Single-chain recombinant traps against TGF-β superfamily growth-factors were designed from the extracellular portion of their cognate natural receptors. The extracellular segment of all these TGF-β superfamily receptors contain a single structured domain that belongs to the snake-toxin family according to SCOP (Andreeva et al., 2008, Nucl. Acid Res. 36: D419) and Pfam (Finn et al., 2006, Nucl Acid Res. 34: D247) structural classifications. The complete extracellular portion of these receptors typically includes unstructured segments flanking their folded ligand-binding domain. These unstructured extracellular portions were apparent from the experimentally determined 3D structures available from the PDB database (Berman et al., 2000, Nucl. Acid Res. 28: 235), e.g., crystal structures for type II TGF-β receptor ectodomain (Hart et al., 2002 Nat. Struct. Biol. 9: 203; Boesen et al., 2002, Structure 10: 913; Groppe et al., 2008, Mol. Cell 29: 157), type I TGF-β receptor ectodomain (Groppe et al., 2008, Mol. Cell 29:157), type IIa activin receptor ectodomain (Allendorph et al., 2006, Proc. Natl. Acad. Sci. USA 103: 7643), type IIb activin receptor ectodomain (Thompson et al., 2003, EMBO J. 22: 1555; Greenwald et al., 2004, Mol. Cell 15: 485), type I BMP receptor ectodomain (Kirsch et al., 2000, Nat. Struct. Biol. 7: 492), or the NMR structure of the type II TGF-β receptor ectodomain (Deep et al., 2003, Biochemistry 42: 10126). In the absence of experimental data, as for example in the case the extracellular region of the IIb splicing variant of the TGF-β type II receptor, unstructured extracellular segments were defined by: (i) sequence portions falling outside of the folded ligand-binding domain boundaries located by comparative analysis against structurally characterized homologs, and (ii) predictions based on knowledge-based algorithms, e.g., DISOPRED (Ward et al., 2004, J. Mol. Biol. 337: 635). Amino acid sequences corresponding to the unstructured (i.e., flexible) and structured (i.e., folded, ligand-binding domain) regions from the ectodomains of several receptors of TGF-β-superfamily growth factors, are given in FIGS. 1A and 1B, respectively.

3. Homo-bivalent single-chain recombinant traps hereby designed against TGF-β-superfamily growth factors disclosed herein were designed with regard to the experimentally determined binding mode between TGF-β-family ligands and the extracellular portion of their cognate natural receptors. The ligand-receptor binding mode was provided at atomic level by the high-resolution 3D structures available for several members of the TGF-β-superfamily ligands in complex with their cognate receptor ectodomains. Examples of experimental molecular structures for TGF-β-superfamily-growth-factor/receptor ectodomain complexes include TGF-β3 bound to TβR-II-ED (Hart et al., 2002 Nat. Struct. Biol. 9: 203), activin bound to ActR-IIb-ED (Thompson et al., 2003, EMBO J. 22: 1555; Greenwald et al., 2004, Mol. Cell 15: 485), BMP-2 bound to type Ia BMP receptor ectodomain BMPR-Ia-ED (Kirsch et al., 2000, Nat. Struct. Biol. 7: 492) and ActR-IIa-ED (Allendorph et al., 2006, Proc. Natl. Acad. Sci. USA 103: 7643), BMP-7 bound to ActR-IIa-ED (Greenwald et al., 2003, Mol. Cell 11: 605). These structures provided the relative spatial orientation between two separate receptor ectodomain chains (molecules) binding simultaneously onto one covalently homodimerized ligand molecule, i.e., 2:1 receptor:ligand stoichiometry. Higher-order ligand-receptor assemblies between a particular TGF-β-superfamily growth factor and ectodomains from different receptor types have also been determined, for example the ternary complexes between TGF-β3, TβR-II-ED and TβR-I-ED (Groppe et al., 2008, Mol. Cell 29:157) or between BMP-2, ActR-IIa-ED and BMPR-Ia-ED (Allendorph et al., 2006, Proc. Natl. Acad. Sci. USA 103: 7643). These structures provide the relative spatial orientation between four separate receptor ectodomain chains (molecules) binding simultaneously onto one covalently homodimerized ligand molecule, i.e., 2:2:1 high-affinity-receptor:low-affinity-receptor: ligand stoichiometry. Such structures were used as guides to design hetero-bivalent, hetero-trivalent and hetero-tetravalent single-chain traps of TGF-β-superfamily growth factors and are useful in designing single-chain traps for other suitable ligands of interest involving the TGF-β superfamily.

4. Homo-bivalent single-chain traps of TGF-β-family ligands were therefore designed as unnatural fusion proteins consisting of the sequence (excluding the signal peptide) of the natural extracellular portion of the receptor repeated twice. FIG. 2A presents schematically homo-bivalent single-chain traps with natural linkers for three TGF-β-family ligands, where structured and unstructured regions are based on experimental data for single-domain extracellular portions, as presented in FIGS. 1A and 1B. This resulted in constructs with two structured domains for binding to select TGF-β-superfamily ligand(s), spaced by an unstructured flexible linker formed by fusing the unstructured C-terminus of the first domain to the unstructured N-terminus of the second domain. The natural linker was also progressively substituted by artificial sequences as well as varied in length (FIGS. 2B-D). From thermodynamic and kinetic considerations, it was expected that divalent receptor ectodomains would provide increased ligand-binding affinities and slower ligand-dissociation rates relative to single-domain receptor ectodomains.

Experiment #2: Feasibility Assessment Procedure for Designed Single-Chain Bivalent Traps To the extent to which the structures of various TGF-β-superfamily growth factors are conserved, the structures of their cognate receptor ectodomains are conserved, and the 2:1 receptor-ligand binding stoichiometry is conserved, the concept of fusing two natural receptor ectodomain sequences to produce single-chain homo-bivalent traps with improved in vitro ligand binding affinity and cellular ligand neutralizing activity relative to respective monovalent receptor ectodomains, is applicable to the entire family of TGF-β family. The feasibility of these ligand traps can be theoretically assessed routinely by following the stepwise procedure outlined below. Although the procedure is presented for homo-bivalent single-chain traps, it also applies to other designs covered here, e.g., hetero-bivalent and hetero-tetravalent single-chain traps.

1. The linear distance is measured between the C-terminal main-chain carbon atom of one domain and the N-terminal main-chain nitrogen atom of the other domain when bound to the covalently-dimerized ligand. Alternate structures of the complex reflecting internal geometrical flexibility in the homodimerization mode of the disulfide-stabilized ligand when bound to the receptor ectodomains, as reported in several cases (Greenwald et al., 2004, Mol. Cell 15: 485), can be included in the design process. A computer hardware equipped with commercial/public software appropriate for manipulating molecular structures on an available graphics device can be routinely employed to this end.

2. The linear distance (in Å units, 1 Å=$10^{-10}$ m) is divided by a factor of 2.5 to calculate the minimum number of amino acid residues that the flexible linker should posses (Table 1) in order to allow simultaneous binding of the folded domains to their binding sites on the homodimeric ligand. The 2.5 factor is based on the Cα-Cα extent of fully extended linkers, which peaks at 3.0 Å (George and Heringa, 2002, Protein Eng. 15: 871), minus an average tolerance of 0.5 Å per amino acid residue to allow for deviations of the linker path from linearity.

(Table 1. Linker characteristics for select examples of single-chain traps of TGF-β-family growth factors. Minimum number of residues required for linkage represents the structure-based linear distance for linkage (Å) divided by a factor of 2.5.)

3. The number of amino acid residues in the unstructured linker portion of the bivalent single-chain trap should be at least equal to the estimated minimum number of linker residues required. Receptor isoforms that differ in the length of the extracellular unstructured segments, such as the TGF-β receptor isoforms II and IIb (FIG. 2B), can be included in the design process. The natural sequence-based linker can also be shortened up to the estimated minimum number of amino acid residues without significantly impairing the ligand binding affinity and neutralizing activity of the trap. A preferable location for shortening the unstructured linker is from the point of fusion (see FIG. 3) in either or both directions relative to the amino acid sequence. Example of shortened natural linkers that can be utilized in single-chain trap design are given in FIG. 2D. As listed in Table 1, the required minimal length of the linker varies between various single-chain traps of TGF-β-superfamily growth factors. An upper limit for the length of the unstructured linker is not defined. Hence, ligand binding agent (trap) constructs with linkers comprising unstructured sequence segments repeated in whole or in part are envisioned to comply with bivalent design and preserve the desired characteristics of the trap. The natural linker can be progressively substituted by artificial sequences, which may or may not result in different linker lengths. Examples of linkers longer than the natural linker designed by repeating of natural sequence or by introducing of artificial sequence are given in FIG. 2D.

4. Finally, atomic-level theoretical analysis is to be carried out, where the linker is modeled between the structured domains and the molecular structure of the trap-ligand complex is refined by minimizing the molecular mechanics energy and by carrying out molecular dynamics simulations (Cornell et al., 1995, J. Am. Chem. Soc. 117: 5179). This may, in some cases, highlight regions of steric and/or electrostatic incompatibility between the trap's linker and the growth-factor, and suggest that the length and/or composition of the linker may be incompatible with the bivalent design, even if the linker complies with the minimum number of amino acids requirement as per step (3.) above. If the linker can be accommodated without affecting the simultaneous binding of the structured domains to their binding sites on the ligand, then the trap construct is deemed feasible for the proposed application. Computer hardware equipped with commercial/public software appropriate for manipulating molecular structures on an available graphics device, and for performing energy calculation and simulation based on molecular mechanics force fields, e.g., the AMBER force field (Cornell et al., 1995, J. Am. Chem. Soc. 117: 5179), can be routinely employed by one skilled in the art in order to carry out this structural modeling analysis. A detailed molecular modeling analysis of the (TβR-II)$^2$ homo-bivalent single-chain trap is provided as an example in the following section and includes molecular dynamics simulation. Examples of molecular mechanics energy-refined models of three single-chain homo-bivalent traps: (TβR-II)$^2$, (ActR-IIb)$^2$ and (BMPR-Ia)$^2$, bound to their respective growth factors are shown in FIGS. 3 and 4. These atomic-level models represent starting points for further computer-based optimization of linker composition and length.

This process is explained in greater detail in the example below:

Modeling Example A, Experiment #2 i. In one example, the atomic-level solution structure of the single-chain homo-bivalent trap (TβR-II)$^2$ was simulated in complex with the growth factor TGF-β3.

The starting point for molecular design of the (TβR-II)$^2$ trap was the 2.15 Å-resolution crystal structure of the disulfide-linked dimeric human TGF-β3 complexed with two TGF-β type II receptor ectodomains (Hart et al., 2002 Nat. Struct. Biol. 9: 203, deposited in the Protein Data Bank (Berman et al., 2000, Nucl. Acid Res. 28: 235) under the code 1 KTZ. Because this structure displays the growth factor in a non-canonical conformation probably due to the low pH used in the crystallization conditions (Hart et al., 2002 Nat. Struct. Biol. 9: 203; Groppe et al., 2008, Mol. Cell 29:157), the binary complex structure was first reconstructed with the ligand in canonical conformation as reported previously (Hinck et al., 1996, Biochemistry 35: 8517; Mittl et al., 1996, Protein Sci. 5: 1261), which was also recently confirmed by the ternary structure of TGF-β ligand-receptor assembly (Groppe et al., 2008, Mol. Cell 29:157). An initial 3D molecular model of the (TβR-II)$^2$ trap incorporating an inter-domain natural linker of 35 amino-acid residues (as per sequence listed in FIG. 2B) was constructed from standard geometries followed by conjugate-gradient energy minimization of the molecular mechanics force field energy using an AMBER all-atom force field (Cornell et al., 1995, J. Am. Chem. Soc. 117: 5179) and the AMBER 9 suite of programs (Case et al., 2005, J Comput. Chem. 26: 1668). During energy minimizations, only the linker regions of the traps were allowed to move, while the coordinates of the growth factors and of the folded domains of the traps were fixed. The resulting 3D molecular model of the homo-bivalent single-chain trap (TβRII)$^2$ bound to TGF-β3 is depicted in FIG. 4.

This initial model of the complex was used as input for molecular dynamics (MD) simulation carried out together with AMBER FF03 force field (Duan et al., 2003, J. Comput. Chem. 24: 1999; Lee & Duan, 2004, Proteins 55: 620) within the AMBER 9 suite of programs (Case et al., 2005, J. Comput. Chem. 26: 1668). The molecular system consisting of 245 amino-acid residues from the single-chain trap (from the full-length (TβR-II)$^2$ trap with 272 amino-acid residues, 21 unstructured residues from the N-terminus and 6 flexible residues from the C-terminus were not included in the MD simulation), 224 amino-acid residues of the TGF-β3 dimer and 14 Na$^+$ counterions (added to maintain electroneutrality) was solvated in rectangular water box using the Xleap program in the AMBER 9 software. The distance between the wall of the box and the closest atom of the solute was 12.0 Å, and the closest distance between the solute and solvent atoms was 0.8 Å. The entire system was energy-minimized by applying harmonic restraints with force constants of 10 kcal/mol/Å$^2$ to all solute atoms, followed by heating from 100K to 300K over 25 ps in the canonical ensemble (NVT), and by equilibrating to adjust the solvent density under 1 atm pressure over 25 ps in the isothermal-isobaric ensemble (NPT) simulation. The harmonic restraints were then gradually reduced to zero with four rounds of 25 ps NPT simulations. After additional 25 ps simulation, a 15 ns production run was obtained with snapshots collected every 1 ps. For all simulations, 2 fs time-step and 9 Å non-bonded cutoff were used. The Particle Mesh Ewald method (Darden et al., 1993, J. Chem. Phys. 98: 10089) was used to treat long-range electrostatics, and bond lengths involving bonds to hydrogen atoms were constrained by SHAKE (Ryckaert et al. 1977, J. Compt. Phys. 23: 327). No other constraints were imposed during the MD simulation.

As seen from FIG. 5A, the single-chain trap (TβR-II)$^2$ bound to TGF-β3 attains a stable MD solution structure that preserves the simultaneous binding of the two ligand-binding domains onto the dimeric growth factor as observed in the crystal structure of unlinked receptor ectodomains (Hart et al., 2002 Nat. Struct. Biol. 9: 203, Groppe et al., 2008, Mol. Cell 29:157). This substantiates the feasibility of the designed single-chain TGF-β trap in terms of the length of the linker. The MD analysis also reveals that in the complex, the linker region of the single-chain trap becomes relatively rigid, with only 6 residues experiencing greater mobility (expressed as per-residue and time-averaged root-mean-square fluctuations) than the rest of the trap's amino acid residues (FIG. 5B). In addition, the single-chain trap established favorable interaction with the growth factor, as evaluated by the solvated interaction energy function for scoring protein-ligand binding affinity (SIE) (Naim et al., 2007, J. Chem. Inf. Model. 47: 122). A highly favorable SIE value of −25.4 kcal/mol was calculated as an average over the last 10 ns of MD simulation (FIG. 5C). This further indicates the feasibility of the employed natural linker in terms of amino acid composition, that is, there were no significant unfavorable steric and electrostatic contacts predicted between the trap's linker and the growth factor.

ii. In one example, structure-based design leads to a divalent molecule consisting of two human TβRII ectodomains that are fused in tandem into a single polypeptide chain (schematically shown in FIG. 6). In this construct, an intervening linker sequence is formed from the unstructured natural C-terminal sequence of one ectodomain (black, 10 residues) and the unstructured natural N-terminal sequence of the other ectodomain (white, 25 residues). This linker bridges between the two structured TGF-β-binding domains. This TGF-β trap is hereby named prototype (TβRII)$^2$. The construct also contains an N-terminal myc tag and C-terminal 6× His tag for ease of detection androtein purification. In the prototype (TβRII)$^2$ the native IPP sequence is replaced by GGR within the linker due to a NotI restriction site inserted during construction of the (TβRII)$^2$ gene. Also shown is another construct with a 35 amino acid residues linker with native IPP restored, and having a N-terminal His tag. This construct is termed "modified N-His" (TβRII)$^2$ and features a native linker sequence. Predicted molecular models of (TβRII)$^2$ bound to TGF-β are given

FIGS. 3-5.

Experiment #3: Small Scale Production of Prototype (TβRII)$^2$ and Demonstration of TGF-β-binding Activity FIG. 6 shows a schematic of prototype (TβRII)$^2$. The prototype (TβRII)$^2$ gene was cloned into mammalian expression vector pTT and increasing amounts were transiently transfected into HEK293 cells. The conditioned media from the transfected cells were collected after 5 days and tested via SPR Biacore analysis for the binding of secreted (TβRII)² to a TGF-β3 surface (FIG. 7A). The sensogram shows increasing levels of binding that correlates with cells transfected with increasing levels of (TβRII)² plasmid (ranging from 1% to 95% transfected cells), indicating a dosage effect and specific binding. The binding characteristics of (TβRII)² (produced from 95%-transfected cells) was compared with dimerized TβRII-Fc and monomeric TβRII (FIG. 7B). The sensogram of prototype
(TβRII)² was similar to the TβRII-Fc interaction (slow off rate), and both were distinct from monomeric TβRII interaction (fast off rate), indicating that (TβRII)² interacts with the TGF-β3 surface in a high-affinity, bivalent manner.

Experiment #4: Production and Purification of Prototype and Modified N-His (TβRII)²

Scaleup production of prototype (TβRII)² in 293 cells resulted in variable yields of protein (1-3 mgs per 1 liter culture) upon purification via cobalt column, perhaps due to a less accessible His tag at the C-terminus. A modified version was constructed having a N-terminal His tag, termed N-His (TβRII)², as shown in FIG. 6. N-His (TβRII)²-transfected HEK293 cells were grown in 500 ml culture. The media was collected, concentrated 5-fold by 10 kDa Centricon filtration and then passed through a 10 ml Fractogel Cobalt column. FIG. 8 shows a SDS-PAGE analysis of N-His (TβRII)² at the various stages of purification. The N-His (TβRII)² in the eluted fractions (lane 6) is relatively pure and migrates as a smear (likely due to glycosylation) in the 50-60 kDa range. The total yield from 500 ml culture was 7-8 mgs, indicating that the N-His (TβRII)² protein is amenable to large-scale production.

Experiment #5: Demonstration that (TβRII)² is a Potent TGF-β Trap

The ability of purified prototype (TβRII)² to neutralize TGF-β was tested on Mv1Lu cells having a TGF-β-responsive luciferase reporter gene and compared with TβRII-Fc from two sources, commercial R&D and collaborator H. Lin (FIG. 9A). The resulting inhibition curves indicated the average $IC_{50}$ for prototype (TβRII)² is 0.58 nM (S.D. 0.64) which is in the same range as for TβRII-Fc Lin (0.45 nM) and slightly higher than TβRII-Fc R&D (0.1 nM). Purified prototype (TβRII)² was also compared with dimeric TβRII-Fc and monomeric TβRII-ED for their ability to competitively bind TGF-β in solution via Biacore analysis (FIG. 9B). Increasing amounts of each binder was added separately to a constant amount of TGF-β1 or -β3 (5 nM) followed by coinjection of this mixture over a TGF-β-specific antibody surface. The level of unbound TGF-β at equilibrium is assessed by the maximum/plateau level of the surface binding curve (FIG. 9B) Prototype (TβRII)² and TβRII-Fc have similarly low IC50s in the range of 5-8 nM, as would be expected for intra-molecular, divalent binding of TGF-β. In contrast, the IC50 for monovalent TβRII-ED is 10-20 fold higher. One might predict, for full avidity, that the IC50 for dimeric (TβRII)² could be at least 100-fold greater than for monomeric TβRII-ED. In order to augment avidity, variable linker lengths may be sampled for (TβRII)² (see FIGS. 2C and 2D). These results (FIGS. 9A and 9B) indicate that (TβRII)² is an excellent trapping/neutralizing reagent for TGF-β and hence is a good candidate therapeutic and/or diagnostic agent for diseases in which TGF-β is causative and overexpressed/overactive (e.g. breast tumors). To this end we examined the ability of prototype (TβRII)² to prevent TGF-β-induced invasion of 4T1 breast cancer cells in vitro (FIG. 9C). Similar to TβRII-Fc, prototype (TβRII)² reduced 4T1 cell invasion to approximately 20% of the non-trap treated (+TGF-β) control.

Experiment #6: Assessment of Binding Characteristics and Efficacy of N-His (TβRII)²

The two different SPR Biacore assays that were utilized in FIG. 7 and FIG. 9B were used again to characterize the N-His (TβRII)²—TGF-β ligand interaction. First, the direct binding assay was utilized where the TGF-β trap was injected over various immobilized TGF-β isoform surfaces. While this assay can verify binding to different TGF-β isoform surfaces, it cannot verify that a 1:1 trap: TGF-β homodimer interaction is occurring in solution due to the nature of using an immobilized TGF-β surface. In order to show trap binding enhancement to soluble TGF-β ligand, indirect binding assays were carried out in which a constant TGF-β concentration was preincubated with various trap or TβRII monomer concentrations and then injected over a 1D11 antibody surface (anti-TGF-β1 to 3). In this manner, the 1D11 surface measures the amount of free (or unbound) TGF-β. A lower IC50 indicates binding enhancement due solely to avidity. In the direct binding assay, the binding of bivalent N-His (TβRII)² to immobilized TGF-β1 and 3 was compared to that of the monomeric N-His TβRII construct (FIG. 10A). N-His (TβRII)² bound to all TGF-β isoforms (1-3), showing a fast on rate and significantly slower off rate of binding to TGF-β1 and β3 compared with monomeric N-His TβRII, as is expected for a bivalent binding interaction. In addition, N-His (TβRII)² showed binding to TGF-β2 whereas monomeric TβRII binding to this isoform was undetectable. We also compared binding of N-His (TβRII)² and TβRII-Fc to TGF-β1 and β3 (FIG. 10B). Both traps showed similar binding kinetics with characteristic fast on rates and slow off rates. In order to assess trap binding to ligand in solution, the indirect binding assay to determine IC50s as carried out using 5 nM TGF-β1. IC50 curves for bivalent N-His (TβRII)², TβRII-Fc and monovalent TβRII (produced either in 293 cells or E. coli) were generated (FIG. 10C). N-His (TβRII)² and TβRII-Fc both showed efficient binding, having IC50s of 1.1 and 1.6 nM, respectively. The IC50s of N-His TβRII (293 cells) and TβRI-IED (E. coli) were approximately 8 and 70 fold higher (respectively) than that of N-His (TβRII)². Similar differences between bivalent and monovalent traps were observed in neutralization assays using Mv1Lu luciferase reporter cells (FIG. 10D). The IC50s for N-His (TβRII)² and TβRII-Fc in this assay were in the sub nM range whereas monomeric N-His TβRII (293 cells) showed only partial neutralization in the 10-100 nM range, and monomeric TβRII (E. coli) was unable to neutralize TGF-β. The results also show that, compared to prototype (TβRII)², the modified N-His (TβRII)² was most efficient in neutralizing TGF-β (compare FIGS. 9A and 10D).

Experiment #7: N-His (TβRII)² Exhibits Long-Term Stability and Activity

The susceptibility of the N-His (TβRII)² to proteolytic degradation was assessed by incubating N-His (TβRII)² in the presence of 10% fetal bovine serum at 37° C. for a period of 7 days (FIG. 11). The western blot on the left shows that N-His (TβRII)² protein remains intact throughout the 7 day period. In addition, the neutralization curves on the right demonstrate that N-His (TβRII)² retains its activity. These results show that N-His (TβRII)² is not adversely sensitive to proteolysis and therefore is a good candidate therapeutic and/or imaging agent for animal studies.

Experiment #8: The N-His (TβRIIb)², Which has a Long Linker (60 Amino Acids, See FIGS. 1A and 2A) is More Potent Than N-His (TβRII)²

The IC50 for N-His (TβRIIb)² for neutralization of TGFβ1 was 0.04 nM (FIG. 12A), which is 4-fold more potent than N-His (TβR11)² (IC50=0.16 nM, FIG. 10D). Similarly, when tested by SPR analysis (Biacore) for binding TGF-β1 in solution, N-His (TβRIIb)² was more potent that N-His (TβRII)² (FIG. 12B). These results illustrate that modification of linker length is at least one parameter whereby trap efficiency can be improved.

Experiment #9: (ActRIIb)²: Another Example of a Single-Chain Receptor Trap Within the TGF-β Family In order to show that the single-chain bivalent receptor strategy taught herein can be applied to other ligands of the TGF-β family, (ActRIIb)² (shown schematically in FIG. 2A) was constructed from the human ActRIIb receptor using this strategy. ActRIIb is the high affinity receptor for both myostatin and activin B. (ActRIIb)² and monomeric ActRIIb were produced in 293 cells and their ability to neutralize myostatin was tested using human rhabdosarcoma A204 cells. These cells have the ActRIIb receptor and were transfected with $(CAGA)_{12}$-luciferase reporter gene (responsive to activin and myostatin) (FIG. 13). (ActRIIb)² exceeded the neutralization potency of monomeric ActRIIb (IC50 of 0.1 and 0.38 nM, respectively), thus demonstrating the better binding efficiency of this bivalent trap. In addition, (ActRIIb)² was 10-fold more potent than dimeric ActRIIb-Fc. These results therefore indicate that the single-chain receptor strategy taught herein can be used as a platform technology to develop effective trapping reagents of other ligands within the TGF-β family.

Experiment #10: (BMPR1a)²: Another Example of a Single-Chain Receptor Trap Within the TGF-β Family Another example of a TGF-β family member trap is (BMPR1a)², shown schematically in FIG. 2A. The (BMPR1a)² trap was compared with monomeric BMPR1a for neutralization of BMP2 (FIG. 14). The bivalent (BMPR1a)² trap was clearly able to neutralize BMP2 whereas monomeric BMPR1a showed poor neutralization.

The multivalent polypeptide ligand binding agents described herein allow for high affinity and specificity by single-chain multivalency. This single-chain attribute is fundamentally different from existing multi-chain agents such as Fc-based fusions (covalent dimer), E/K-coiled-coil-based fusions (non-covalent dimer), or described cytokines and ligand traps that include fused multimerizing moieties. The present design can facilitate tissue penetration, thereby increasing access to sites of interest. The present design can also provide a shorter half life in systemic circulation, which can be desirable for certain applications such as imaging and other diagnostic applications, as well as where ongoing abundant systemic distribution of the antagonist is not desirable. In addition, the present design permits linkage of other cargo molecules (for example imaging agents like fluorescent molecules), toxins, etc.

Linkers can be designed to facilitate purification of the linker and/or ligand binding agent. The exact purification scheme chosen will determine what modifications are needed, for example, additions of purification "tags" such as His tags is contemplated.

The general Structure I

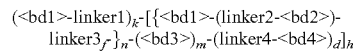

can be modified to add one or more cargo and/or accessory molecules (referred to collectively herein by $R_1$, $R_2$, $R_3$, $R_4$, etc.).

For example, to provide Structure V:

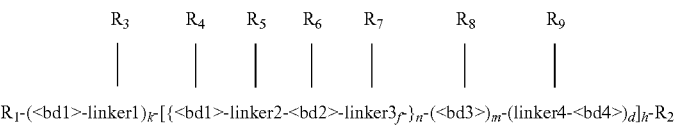

Where bd1, bd2, bd3, bd4, linker1, linker2, linker3, linker4, k, f, n, m, d, and h are defined as in Structure I.

Without limiting the generality of R substitutients available, $R_1$, $R_2$, $R_3$, $R_4$, $R_5$, $R_6$, $R_7$, $R_8$, $R_9$, may be the same or different, may not be present and when present, may independently be one or more of:

- A fusion protein for targeting such as an antibody fragment (e.g. single chain Fv) and/or a single domain antibody (sdAb).
- A radiotherapy and/or imaging agent such as a radionuceotide (e.g., $^{123}I$, $^{111}In$, $^{18}F$, $^{64}C$, $^{68}Y$, $^{124}I$, $^{131}I$, $^{90}Y$, $^{177}Lu$, $^{67}Cu$, $^{213}Bi$, $^{211}At$), a fluorescent dye (e.g. Alexa Fluor, Cy dye) and/or a fluorescent protein tag (e.g. GFP, DsRed).
- A cytotoxic agent for chemotherapy such as doxorubicin, calicheamicin, a maytansinoid derivatives (e.g. DM1, DM4), a toxin (e.g. truncated Pseudomonas endotoxin A, diphtheria toxin).
- A nano particle-based carrier such as polyethylene glycol (PEG), a polymer-conjugated to drug, nanocarrier or imaging agent (e.g. of a polymer N-(2-hydorxylpropyl) methacrylamide (HPMA), glutamic acid, PEG, dextran).
- A drug (e.g. doxorubicin, camptothecin, paclitaxel, palatinate).
- A nanocarrier such as a nanoshell or liposome.
- An imaging agent such as Supermagnetic Iron Oxide (SPIO)
- A dendrimer
- A solid support for use in ligand purification, concentration or sequestration (e.g. nanoparticles, inert resins, suitable silica supports).

In general, it will not be preferable to have cargo or accessory molecules in all possible positions, as this may cause steric or electrostatic complications. However, the effects of adding a cargo or accessory molecule to any given position or positions on the structure can be determined routinely in light of the disclosure herein by modeling the linker between the binding domains and carrying out molecular dynamics simulations to substantially minimize molecular mechanics energy and reduce steric and electrostatic incompatibility between the linker and the member of the TGF-β superfamily as taught herein.

It will frequently be preferable to add the cargo or accessory molecule to the linker portion of the agent, rather to the binding domain, to reduce the likelihood of interference in binding function. However, addition to the binding domain is possible and could be desirable in some instances and the effect of such an addition can be determined routinely in advance by modeling the binding agent and the linker with the proposed addition as described herein.

In certain embodiments of conjugation to cargo molecules and accessory molecules, the following structures will be produced:
R-[bd]-(linker-[bd])$_n$
[bd]-(R-linker-[bd])$_n$
R-[bd]-(linker-[bd]-R)$_n$
R-[bd]-(R-linker-[bd])$_n$
[bd]-(R-linker-[bd]-R)$_n$
R-[bd]-(R-linker-[bd]-R)$_n$ Conjugation methodologies are somewhat diverse but typically can be performed using commercial kits that enable conjugation via common reactive groups such as primary amines, succinimidyl (NHS) esters and sulfhydral-reactive groups. Some examples are; Alexa Fluor 488 protein labeling kit (Molecular Probes, Invitrogen detection technologies) and PEGylation kits (Pierce Biotechnology Inc.).

Many embodiments of the binding agents taught herein will have a lower molecular mass, as compared with competing multivalent receptor-based neutralizing agents.

In an embodiment of the invention there is provided ligand binding agents wherein the intervening linker sequence, between the ligand-binding domains, is composed of native amino acids, the sequence of which is based on the receptor ectodomains (e.g. the various linkers shown in FIG. 2B and the "repeat" and "delete" linkers shown in FIG. 2D) or conservative substitutions of natural or unnatural amino acids into such regions or reversal of such natural or modified sequences. It will frequently be considered preferable to use unstructured regions from these receptor ectodomains as the template for linker design. Once linkers have been designed, it will generally be preferred to test their effectiveness using the procedures described herein or other substantially functionally equivalent procedures. Routine testing for immunogenicity may be desired for in vivo use.

In some instances, it will be desirable to subject the polypeptide-based linking design of the ligand binding agents disclosed herein to optimization of characteristics desired for a particular application. For example, the linker may be modified in length and composition based on atomic-level simulations and knowledge-based design in order to improve binding affinity, specificity, immunogenicity and stability. This is applicable to a wide range of molecular systems exhibiting homomeric, heteromeric, dimeric and multimeric ligand-receptor structural characteristics Additional different binding domains can be incorporated to generate multivalent traps with even higher binding potency.

In an embodiment of the invention, a non-naturally occurring single-chain hetero-bivalent polypeptide is produced by the inline fusion of two or more different structured ligand-binding domains (denoted <bd1>, <bd2>, <bd3> and <bd4>) from the extracellular portion of distinct natural receptors, and which is not fused to any dimerizing or multimerizing moieties. In some instances, this polypeptide will have the general structure <bd1>-linker2-<bd2>. In some instances, the binding domains will be selected from the ectodomains of the TβR-II and TβRI receptors, and fused to produce hetero-bivalent single-chain traps active against TGF-β isoforms. In other instances, the binding domains will be selected from the ectodomains of the ActR-IIa and BMPR-Ia receptors and fused to generate single-chain hetero-bivalent traps active against activin, myostatin and BMP isoforms. In other embodiments, the binding domains are selected from other receptors tomembers of the TGF-β superfamily.

In another embodiment of the invention a non-naturally occurring single-chain hetero-trivalent polypeptide is produced by the inline fusion of two or more different structured ligand-binding domains (denoted bd1 and bd2) from the extracellular portion of distinct natural receptors, and which is not fused to any dimerizing or multimerizing moieties. In some instances, this polypeptide will have the general structure [bd1]-linker1-[bd2]-linker2-[bd2]. In other instances, this polypeptide will have the general structure [bd1]-linker1-[bd1]-linker2-[bd2]. In some instances, [bd1] and [bd2] will be selected from the ectodomains of the TβR-II and TβRI receptors, and fused to produce hetero-bivalent single-chain traps active against TGF-β isoforms. In other instances, bd1 and bd2 will be selected from the ectodomains of the ActR-IIa and BMPR-Ia receptors and fused to generate single-chain hetero-bivalent traps active against activin, myostatin and BMP isoforms.

In another embodiment of the invention a non-naturally occurring single-chain hetero-tetravalent polypeptide is produced by the inline fusion of two or more identical or different structured ligand-binding domains from the extracellular portion of natural receptors repeated twice or more times in various orders. In an embodiment to the invention this heterotetravalent polypeptide is not fused to any dimerizing or multimerizing moieties. In one embodiment, this polypeptide will have the general structure [bd1]-linker1-[bd2]-linker2-[bd1]-linker1-[bd2]. In other instances, this polypeptide will have the general structure [bd1]-linker1-[bd1]-linker2-[bd2]-linker3-[bd2].

In one embodiment, this polypeptide will have the general structure [bd1]-linker1-[bd2]-linker2-[bd2]-linker3-[bd1]. In some instances, [bd1] and [bd2] will be selected from the ectodomains of the TβR-II and TβR-I receptors, and fused to produce single-chain hetero-tetravalent traps active against TGF-β isoforms. In other instances, [bd1] and [bd2] will be selected from the ectodomains of the ActR-IIa and BMPR-Ia receptors and fused to generate single-chain hetero-tetravalent traps active against activin, myostatin and BMP isoforms.

Specific non-limiting examples of embodiments of heteromeric single-chain traps against TGF-β are represented schematically as well as with full sequence details in FIGS. 15A and 15B.

A nucleotide sequence encoding a single-chain protein produced according to the teachings herein can be cloned and inserted into any suitable vector and therefore is very amenable to production (i.e. there is no requirement for two vectors, or one vector with two promoters, to express two receptor ectodomains).

The linker region provides a segment that is distinct from the structured ligand binding domains and thus can be used for conjugation to accessory molecules (for example, molecules useful in increasing stability such as PEGylation moieties) or cargo molecules such as contrast agents (for imaging) without having to chemically modify the binding domains.

In an embodiment of the invention in which the ligand-binding domains and the linker contain primarily natural sequences they would not ordinarily be expected to be severely immunogenic or toxic in a typical patient.

Smaller size (for example, 50-60 kDa for (TβRII)$^2$ compared to 100-120 kDa for TβRII-Fc or 150 kDa for monoclonal antibodies) will generally be expected to increase access to target tissues.

Large scale production is an attainable goal. One 500 ml scale-up of N-His (TβRII)² in 293 cells yielded 7 mg of purified protein.

In some instances, it may be desirable to permit a computer or other machine capable of calculation to determine linker length according to the disclosure herein. Thus, in an embodiment of the invention there is provided a data storage medium comprising instructions for determining the minimum linker length. In an embodiment of the invention there is provided a data storage medium comprising a means for identifying acceptable minimal linker length.

Linker length will be considered acceptable when it permits binding of binding domains located on each of the N- and C-termini of the linker to bind their natural binding sites on their natural ligand such that, with both binding domains so bound, the ligand is bound with a higher affinity than it would be bound by binding of only one of the binding domains.

Methods
Construction and Cloning of TGFβ Family Traps
1) Prototype (TβRII)²
Step 1: The mammalian expression vector pTT2-RIIE (De Crescenzo el al., 2003, J. Mol. Biol. 328: 1173), which contains a myc-tagged ectodomain of the human type II TGF-β receptor (TβRII) was cut with NotI and BamHI to eliminate E-coil/His regions. Step 2: A second ectodomain of TβRII was PCR amplified from plasmid huTGFβRII/pCDNA3 as template and using primers R2ECD3'Bamrev2 and R2ECD 5'Not to incorporate a 3' 6-His tag+Bam HI site, and a 5' Not I restriction site, respectively.

```
R2ECD3'Bamrev2:
                                    SEQ ID NO 1
GACAGGATCCTAGTGATGATGGTGGTGATGGTCAGGATTGCTGGTGT

TATATTC

R2ECD 5'Not:
                                    SEQ ID NO 2
CACGGCGGCCGCCACGTTCAGAAGTCGGTTAATAAC
```

This PCR product was ligated to pCDNA3 cut with NotII- and BamHI. The insert was verified by sequencing, re-excised by Not I/Bam HI digestion and then cloned into the vector from step 1, resulting in the assembly of two TβRII ectodomains in tandem. The sequence of this construct was verified by sequencing and the amino acid sequence of the prototype (TβRII)² protein is shown below and is presented schematically in FIG. 6.

```
Prototype (TβRII)²:
                                    SEQ ID NO 3
[MGRGLLRGLWPLHIVLWTRIAST]IPP EQKLISEEDLL HVQKSVNNDM

IVTDNNGAVKFPQLCKFCDVRFSTCDNQKSCMSNCSITSICEKPQEVCV

AVWRKNDENITLETVCHDPKLPYHDFILEDAASPKCIMKEKKKPGETFF

MCSCSSDECNDNIIFSEEYNTSNPDGGRHVQKSVNNDMIVTDNNGAVKF

PQLCKFCDVRFSTCDNQKSCMSNCSITSICEKPQEVCVAVWRKNDENIT

LETVCHDPKLPYHDFILEDAASPKCIMKEKKKPGETFFMCSCSSDECND

NIIFSEEYNTSNPD HHHHHH
```

* The gray sequence within brackets denotes the huTβRII signal peptide which is cleaved upon processing in 293 cells. The boxed sequences (EQK . . . LL and HH . . . HH), are Myc and His tags, respectively.

2) Modified N-His (TβRII)² and N-His TβRII Monomer
Step 1: Reversion of non-native amino acids GGR to native amino acids IPP in the linkers of prototype (TβRII)²

The Not1 site within the linker coding sequence of prototype (TβRII)² created a GGR sequence (underlined in the amino acid sequences shown above). This was reverted back to the native IPP sequence by PCR-based mutagenesis. Internal primers 2XR2mutfor and 2Xmutrev span the region to be mutated and two flanking primers pTT2 5' and pTT2 3' contain the flanking regions.

```
2XR2mutfor:
                                    SEQ ID NO 4
CCTGACATCCCACCGCAGGTTCAGAAG 2Xmutrev:
                                    SEQ ID NO 5
GAACGTGCGGTGGGATGTCAGGATTGC pTT2 5'
                                    SEQ ID NO 6
ATACACTTGAGTGACAATGACA pTT2 3'
                                    SEQ ID NO 7
AAAATTCCAACACACTACTTTGCAATCT
```

The template used was pTT2-prototype(TβRII)². Primers pTT2 5' and 2XR2mutrev were paired to create PCR fragment 1. Primers 2XR2mutfor and pTT2 3' were paired to create PCR fragment 2. The PCR fragments 1 and 2 were heated at 95° C. and allowed to anneal together. The flanking primers were then used to amplify the assembled fragment 1+2. The amplified fragment 1+2 was then cut with HindIII and BamHI and inserted into pTT vector also cut with HindIII and BamHI. The resultant plasmid was designated pTT2-native (TβRII)².

Step 2: Elimination of C-terminal His and N-terminal Myc tags and fusion with N-terminal His tag/thrombin cleavage site.

Two primers were designed, incorporating the desired sequence change (restriction sites, thrombin cleavage site, and eliminating the mycMyc tag, and the His tag).

```
BamHI-Thr-IPP-R2ECD_for:
                                    SEQ ID NO 8
GGATCCTTCAACCCGCGTATTCCGCCGCACGTTCAGAAGTCGGTT BstBI stop R2ECD rev:
                                    SEQ ID NO 9
GCGTTCGAACTAGTCAGGATTGCTGGTGTTATATTC
```

These primers were used to generate two fragments by PCR using pTT2-native(TβRII)² as a template: fragment 1XECD (monomer) and 2XECD (dimer). Both fragments were digested with BstBI and BamHI and cloned separately into plasmid vector pTTVH8G (unpublished, derived from pTT vector; Durocher et al., 2002, Nucl. Acid. Res. 30: No. 2 e9) which has the human VEGF signal sequence/10 N-terminal amino acids of VEGF and 8× his tag. The protein sequences of the resulting constructs are as follows:

N-His (TβRII)²:
SEQ ID NO 10

[MNFLLSWVHWSLALLLYLHHAKWSQA]APMAEGGGQNHHHH

HHHHGGSFNPRIPP HVQKSVNNDMIVTDNNGAVKFPQLCKF

CDVRFSTCDNQKSCMSNCSITSICEKPQEVCVAVWRKNDEN

ITLETVCHDPKLPYHDFILEDAASPKCIMKEKKKPGETFFMC

SCSSDECNDNIIFSEEYNTSNPDIPPHVQKSVNNDMIVTDN

NGAVKFPQLCKFCDVRFSTCDNQKSCMSNCSITSICEKPQE

VCVAVWRKNDENITLETVCHDPKLPYHDFILEDAASPKCIMK

EKKKPGETFFMCSCSSDECNDNIIFSEEYNTSNPD

* The gray sequence within brackets denotes the VEGF signal peptide. The boxed sequences; (HH . . . HH and IPP), are the His tag and reverted IPP sequence, respectively.

N-His TβRII monomer:
SEQ ID NO 11

[MNFLLSWVHWSLALLLYLHHAKWSQA]APMAEGGGQNHHHH

HHHHGGSFNPRIPP HVQKSVNNDMIVTDNNGAVKFPQLCKF

CDVRFSTCDNQKSCMSNCSITSICEKPQEVCVAVWRKNDEN

ITLETVCHDPKLPYHDFILEDAASPKCIMKEKKKPGETFFMC

SCSSDECNDNIIFSEEYNTSNPD

3) N-His (TβRIIb)²

Step 1: Assembly of (TβRIIb)2 Gene.

a. Plasmid pTT2-native(TβRII)² was cut with NotI and BamHI to eliminate the second TβRIIECD.

b. A PCR fragment was generated using plasmid pRC/CMV-huTβRIIb (containing the human TβRIIb gene) as a template with the following primers:

```
R2ECD-3'Bamrev-2:
                                SEQ ID NO 12
GACAGGATCCTAGTGATGATGGTGGTGATGGTCAGGATTGCTGGT GTTATATTC
and R2bECD 5'Not for:
                                SEQ ID NO 13
CACGGCGGCCGCCACGTTCAGAAGTCGGATGTGG
```

The resulting fragment comprised the TβRIIb with a 3' 6-His tag, Bam HI site and stop codon, and Not I at the 5' end. This fragment was cut with Not I and Bam HI and then cloned into the the vector from step a.

Step 2:

Using the plasmid from step 1b as template a PCR fragment was generated (that eliminates the N-terminal Myc tag and C-terminal His tags) with the following primers:

```
BamHI-Thr-IPP-R2-ECD-for:
                                SEQ ID NO 14
GGATCCTTCAACCCGCGTATTCCGCCGCACGTTCAGAAGTCGGTT
```

```
BstBI stop R2ECD rev:
                                SEQ ID NO 15
GCGTTCGAACTAGTCAGGATTGCTGGTGTTATATTC
```

The resulting PCR fragment was digested with the appropriate enzymes and subcloned into pTTVH8G. The protein sequence of the this trap is as follows:

N-His (TβRIIb)2:
SEQ ID NO 16

[MNFLLSWVHWSLALLLYLHHAKWSQA]APMAEGGGQNHHHHHHHHGGSF

NPRIPPHVQKSVNNDMIVTDNNGAVKFPQLCKFCDVRFSTCDNQKSCMSN

CSITSICEKPQEVCVAVWRKNDENITLETVCHDPKLPYHDFILEDAASPK

CIMKEKKKPGETFFMCSCSSDECNDNIIFSEEYNTSNPDIPPHVQKSDVE

MEAQKDEIICPSCNRTAHPLRHINNDMIVTDNNGAVKFPQLCKFCDVRFS

TCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPD

* The gray sequence within brackets denotes the VEGF signal peptide. The boxed sequence is the His tag.

4) (ActRIIB)² and ActRIIB Monomer

For construction of (ActRIIB)², three primer pairs (1+2, 3+4, 5+6) were used to generate 3 PCR fragments (A, B and C) using a plasmid containing the human ActRIIB sequence as a template.

```
Primer1:
                                SEQ ID NO 17
cgcagatctgcggccgcATGACGGCGCCCTGGGTGGCCCTCGC

CCTCCTCTGGGGATCGCTGTGCGCAGGATCAGGATCAGAACAG

AAGCTGATCaGCG

Primer2:
                                SEQ ID NO 18
CCGtGATCAGCTTCTGTTCTGATCCTGATCCTGCGCACAGCGA TCCCCAGAGGAGGGCGAGGGCCACCCAGGGCGCCGTCATgcgg ccgcagatctggc Primer3:
                                SEQ ID NO 19
GGCaGATCTCCGAGGAAGATTTACTAGGGCGTGGGGAGGCTGA

GACACGGGAGTG CATC

Primer4:
                                SEQ ID NO 20
ccgactagtGGGGGCTGTCGGGGGTGGCTC Primer5:
                                SEQ ID NO 21
ccgactagtGGGCGTGGGGAGGCTGAGAC Primer6:
                                SEQ ID NO 22
cgctggatccCTAATGGTGATGATGGTGATGGGTGGGGCTGTC

GGGGGTGGC
```

PCR Fragment A containins 5' Bgl II and NotI sites, the ATG start codon, the signal peptide and the 5' half of the Myc tag and Bcl I site. PCR fragment B contains the first ECD, with a BgIII site and the 3' half of the Myc tag and SpeI site. Fragment C contains the second ECD, SpeI site at the 5' end, and a BamHI site, stop codon, the 6× his tag at the 3' end.

These fragments were subcloned into pGemT vector (Promega), digested with the appropriate enzymes, and ligated together. The resulting A+B+C fragment, which encodes the (ActRIIB)² single chain dimer, was cut using NotI and BamH1 and inserted into pTT expression vector. The ActRIIB monomer was assembled in a similar manner using primer pairs 1+2 and 3+6. The resulting constructs have the following protein sequences:

(ActRIIB)²:
SEQ ID NO 23
[MTAPWVALALLWGSLCAG] SGS EQKLISEEDLL GRGEAETRECIYYNA

NWELERTNQSGLERCEGEQDKRLHCYASWRNSSGTIELVKKGCWLDDFN

CYDRQECVATEENPQVYFCCCEGNFCNERFTHLPEAGGPEVTYEPPPTA

PTSGRGEAETRECIYYNANWELERTNQSGLERCEGEQDKRLHCYASWRN

SSGTIELVKKGCWLDDFNCYDRQECVATEENPQVYFCCCEGNFCNERFT

HLPEAGGPEVTYEPPPTAPT HHHHHH

ActRIIB monomer:
SEQ ID NO 24
[MTAPWVALALLWGSLCAG] SGS EQKLISEEDLL GRGEAETRECIYYNA

NWELERTNQSGLERCEGEQDKRLHCYASWRNSSGTIELVKKGCWLDDFN

CYDRQECVATEENPQVYFCCCEGNFCNERFTHLPEAGGPEVTYEPPPTA

PT HHHHHH

*The gray sequence within brackets denotes the human ActRIIB signal peptide. The boxed sequences; (EQK . . . LL and HH . . . HH), are Myc and His tags, respectively.

5) (BMPR1a)² and BMPR1a Monomer

For construction of (BMPR1a)², 2 primer pairs (1+2, 5+6) were used to generate two PCR fragments (A, B) using a plasmid containing the human BMPR1a (ALK3) sequence as a template.

```
Primer1for:
                                    SEQ ID NO 25
GCG AAG CTT ATG CCT CAG CTA TAC ATT TAC ATC Primer4rev:
                                    SEQ ID NO 26
CGGC CTC CGG ATG CTG CCA TCA AAA AAC GG Primer5for:
                                    SEQ ID NO 27
CCGCG CGC CGG CAG AAT CTG GAT AGT ATG CTT
C Primer6rev:
                                    SEQ ID NO 28
CGAC AGG ATC CTA GTG ATG ATG GTG GTG ATG

TCG AAT GCT GCC ATC AAA AAA CGG
```

PCR fragment A contains a 5'Hind III site, start codon, signal peptide and first BMPR1aECD. PCR fragment B contains the second BMPR1aECD, 6× his tag, stop codon and BamHI site.

These fragments were subcloned into pGemT vector (Promega), digested with the appropriate enzymes, and ligated together. The resulting A+B fragment, which encodes the (BMPR1a)² single-chain dimer, was cut with HindIII and BamH1 and inserted into pTT2 expression vector. The BMPR1a monomer was assembled using primer pairs 1+6. The resulting constructs have the following protein sequences:

(BMPR1a)²:
SEQ ID NO 29
[MPQLYIYIRLLGAYLFIISRVQG] QNLDSMLHGTGMKSDSDQKKSENG

VTLAPEDTLPFLKCYCSGHCPDDAINNTCITNGHCFAIIEEDDQGETTL

ASGCMKYEGSDFQCKDSPKAQLRRTIECCRTNLCNQYLQPTLPPVVIGP

FFDGSIRQNLDSMLHGTGMKSDSDQKKSENGVTLAPEDTLPFLKCYCSG

HCPDDAINNTCITNGHCFAIIEEDDQGETTLASGCMKYEGSDFQCKDSP

KAQLRRTIECCRTNLCNQYLQPTLPPVVIGPFFDGSIR HHHHHH

BMPR1a monomer:
SEQ ID NO 30
[MPQLYIYIRLLGAYLFIISRVQG] QNLDSMLHGTGMKSDSDQKKSENG

VTLAPEDTLPFLKCYCSGHCPDDAINNTCITNGHCFAIIEEDDQGETTL

ASGCMKYEGSDFQCKDSPKAQLRRTIECCRTNLCNQYLQPTLPPVVIGP

FFDGSIR HHHHHH

* The gray sequence within brackets denotes the human BMPR1a signal peptide. The boxed sequence is the His tag.

Expression and Purification of Ligand Binding Agents

Modifed human embryonic kidney cells (293-EBNA1 clone 6E) stably expressing EBNA1 were transfected using 25 kDa linear polyethylenimine (PEI) (Poysciences, Warrington, Pa.) as described below (and Durocher et al., 2002, Nucl. Acid Res. 30: e9)). The cells growing as suspension cultures in Freestyle medium (Invitrogen) were transfected at $1\times10^6$ cells/ml with variable amounts of pTT vector plasmid DNA (for small scale cultures), or a fixed amount of plasmid DNA (for large scale culture), and 2 ug/ml PEI.

1. Small-Scale Transient Transfections:

Five hundred microliters of the suspension culture was distributed per well in a 12-well plate. DNA was diluted in Freestyle medium (in a volume equivalent to one-tenth of the culture to be transfected), PEI was added, and the mixture immediately vortexed and incubated for 10 min at room temperature prior to its addition to the cells. Following 3 h incubation with DNA-PEI complexes, culture medium was completed to 1 ml. The culture was harvested 5 days after transfection and the media was clarified by centrifugation at 3500 g for 10 min and sterile filtered. Aliquots of conditioned media were analyzed for TGF-β binding activity via SPR analyses (see below and FIG. 7A)

2. Large-Scale Cultures and Protein Purification:

Large scale cultures were processed as per (Pham et al., 2005: Biotechnol. Bioeng. 90: 332). Bioreactors of 1 L (Biostat Q, B. Braun, Germany) were equipped with 45° pitched blade impellers and stirring speed was maintained at 100 rpm. Surface aeration was applied with a gas mixture of nitrogen, carbon dioxide and oxygen at a gas-flow rate of 100 standard cubic cm/min). The dissolved oxygen tension was controlled at 40% air saturation. The temperature was maintained at 37° C. and the pH was maintained at 7.15 with $CO_2$ at the beginning of the run and with $NaHCO_3$ (7.5% w/v) during the cell growth phase. A feed with 0.5% (w/v) TN1 peptone (OrganoTechnie) was done 24 hours post-transfection. The culture medium was harvested 120 hours post transfection and trap protein was purified by immobilized metal affinity chromatography on Fractogel-Cobalt column as previously described (Cass et al., 2005, Protein Expr. Purf. 40: 77) except that wash and elution steps contained 25 mM and 300 mM imidazole respectively. A 10 ml column packed with 5 cm Talon Metal Affinity Resin (BD Biosciences, Mississauga, Ont.) and was equilibrated with 10 column bed volumes (CVs) of Talon Wash Buffer (TWB: 50 mM sodium phosphate, 300 mM NaCl, pH 7). The conditioned medium was passed through a 0.22 µm filter, and then loaded by gravity. The column was washed with 10 CVs of TWB and (TβRII)$^2$ was eluted in 1 ml fractions using 300 mM imidazole in TWB. Eluted trap protein was then desalted in PBS using a HiPrep 26/10 desalting column (GE-Healthcare) as recommended by the manufacturer. Protein concentration was determined by Bradford using BSA as a standard. The progress of the various stages of purifcation for N-His (TβRII)$^2$ is seen in FIG. 8.

Surface Plasmon Resonance (SPR) Experiments

Analyses of Conditioned Media of Transfected 293-EBNA1 clone 6E Cells for TGFβ-Binding Activity Conditioned media from cells, transfected with increasing amounts of pTT2-prototype (TβRII)$^2$ plasmid (to generate increasing percentages of transfected cells ranging form 1-95%), were collected 5 days post-transfection and sterile filtered (0.22 µm). The samples were diluted to 1:100 or 1:20 using HBS buffer (10 mM HEPES, 150 mM NaCl, 3.4 mM EDTA, and 0.02% Tween 20) prior to surface plasmon resonance (SPR) analysis of the (TβRII)$^2$ interaction with TGF-β3. SPR data was generated using a Biacore 3000 instrument (G.E. Healthcare Inc.) at 25° C. using HBS as running buffer. Ligand was prepared by covalently immobilizing 2000 resonance units (RUs) of TGF-β3, along with a mock blank control surface, onto a Biacore CM-5 sensor chip using standard amine coupling methods. Samples were injected simultaneously over the TGF-β3-immobilized and blank surfaces for 240 s followed by a 240 s dissociation time at a flow rate of 10 µl/min. Specific (TβRII)$^2$-TGF-β3 interaction sensograms were generated by subtracting the sensogram generated from the blank surface from the one generated from the TGF-β3-immobilized surface. The sensograms were aligned to the injection start points using BiaEval software version 4.1 (Biacore Inc.), as shown in FIG. 7A.

Association and Dissociation of TβRII, Prototype (TβRII)$^2$ and TβRII-Fc with TGFβ

Sensograms comparing (TβRII)$^2$ with TβRII-Fc and *E. coli*-produced monomeric TβRII ectodomain were generated. The ligand surface and injection conditions were the same as described above except injection times were for 120 s. Solutions containing 200 nM purified TβRII and 25 nM TβRII-Fc in HBS buffer were used for analysis. (TβRII)$^2$-conditioned media (from 95% transfected cells) was diluted 1:20 in HBS buffer. The SPR sensograms generated from these sample injections were aligned to their injection start point and normalized to a maximum RU response of 100 using Biacore BiaEval software version 4.1 (Biacore Inc.), as shown in FIG. 7B.

Comparison of the TGFβ-Binding Efficacies of Purified (TβRII)$^2$, TβRII-Fc and TβRII Monomer Solutions containing a TβRII variant ((TβRII)$^2$, TβRII-Fc or *E. coli*-produced TβRII) and 5 nM of TGF-β V or (β1 or β3) were pre-incubated and then injected over covalently immobilized 1D11 anti-TGF-β antibody (R&D Systems) under mass-transport limiting conditions to measure free TGF-β. SPR data was generated using a Biacore 3000 instrument (G.E. Healthcare Inc.) using HBS as running buffer. A high density 1D11 surface (approximately 10,000 RUs) and matching blank control surface were created on a Biacore CM-5 sensorchip using standard amine coupling methods. A twenty-fold stock concentration of TGF-β (100 nM in 10 mM acetic acid) was used. This gave the final 1-fold assay concentration of TGF-β (5 nM) when 10 µl was added to 190 µl HBS containing a TβRII variant at a 1.05 times final concentration. Blank injection samples were made from 10 µl 10 mM acetic acid mixed with 190 uL HBS. TGF-β was added to the TβRII variant solution using the TRANSFER command, mixed, and incubated for 120 s at 4° C. prior to injection over the 1D11 surface. Using the KINJECT command, samples were simultaneously injected for 5 min over the 1D11 and control surfaces with a 30 s dissociation time at a flow rate of 5 µl/min at 25° C. The 1D11 surface was regenerated for the next cycle by injecting 10 mM HCl for 15 s at 20 µl/min using the INJECT command. All sensogram analysis was carried out using Biacore BiaEvaluation software v4.1 (G.E. Healthcare Inc.). TβRII variant sensograms were aligned to the injection start point, and double-referenced using the control surface and blank injection sensograms. The plateau levels (which measure the amount of free TGFβ) were taken from the average value of the stabilized dissociation phase of each double-referenced sensogram. Examples are shown in FIGS. 9B, 10C and 12B.

Comparison of the Antagonistic/Inhibitor Potencies of Various Binding Agents by Luciferase Reporter Assays 1. Luciferase Assay for a TGF-β Binding Agent in Mink Lung Epithelial (Mv1Lu) Cells.

Mink lung epithelial cells, stably transfected with the TGF-β-responsive PAI-1 promoter fused to the firefly luciferase reporter gene (Abe et al., 1994, Anal. Biochem. 216: 276), were used. These cells were plated in 96-well tissue culture plates ($2 \times 10^4$ cells/well) in Dulbecco's modified Eagle's medium containing 5% fetal bovine serum and were allowed to attach for at least 6 h at 37° C. Cells were then washed with phosphate buffered saline (PBS), and the medium was replaced by Dulbecco's modified Eagle's medium containing 1.0% fetal bovine serum and 0.1% bovine serum albumin (DMEM-1, 0.1% BSA). Various concentrations of purified (TβRII)$^2$ or (TβRIIb)$^2$ trap or TβRII-Fc (either from R&D Systems or collaborator Dr. Herbert Lin) were mixed with 20 pM TGF-β1 in DMEM-1, 0.1% BSA) and added to the cells. After 16 hr. incubation at 37° C., the medium was removed, and the cells were washed once with PBS. Cells were then lysed with 25 µl reporter lysis buffer (Promega Corp.) and assayed for luciferase activity using the Promega luciferase assay kit according to the manufacturer's instructions. Luminescence was measured in a MRX (Dynex Inc.) or Lumioskan RS (Global Medical Instrumentation, Inc.) microplate reader. The activity is expressed as the percentage of the maximum TGF-β1 activity (i.e. in the absence of any antagonist) or relative luciferase units (RLU) (see examples shown in FIGS. 9A, 10D and 12A).

2. Luciferase Assay for ActRIIB Binding Agents in A204 Cells.

A204 cells (rhabdomyosarcoma, ATCC) were plated in 48-well culture plates ($5 \times 10^4$ cells/well) in McCoy's 5A Media (ATCC) supplemented with 10% Fetal bovine serum. After 24 hrs. the cells were transfected with (CAGA)$_{12}$MLP-Luc (luciferase reporter responsive to Activin and myostatin; Dennler et al., 1998, EMBO J. 17: 3091) and pRL-CMV (constitutive renilla reporter for normalization of transfections, Promega Corp.) using Lipofectamine 2000 transfection reagent, according to the manufacturer's specifications (Gibco-BRL). After 24 hours the cells were washed once with DMEM-1, 0.1% BSA and then treated with 4 nM human myostatin (GDF8, R&D Systems) without or with increasing concentrations of ActRIIb trap or ActRIIb-Fc (R&D Systems) for 6 hrs, 37° C. The cells were then washed once with PBS and lysed with 50 µl 1× Passive lysis buffer. The lysates were measured by a dual firefly/renilla luciferase reporter kit, according to the manufacturer's (Promega Corp). The activity is expressed as firefly RLU normalized to renilla (see example shown in FIG. 13).

3. Luciferase Assay for BMPR1a Binding Agents in C2C12BRA Cells.

C2C12BRA cells (mouse myoblast cells stably transfected with a BMP-luciferase reporter; Zilderberg et al., 2007, BMC Cell Biology 8: 41) were plated onto 96-well culture plates ($5 \times 10^3$ cells/well) in DMEM supplemented with 10% fetal bovine serum. After 24 hrs. the cells were washed once with DMEM-1, 0.1% BSA and then treated with 1 nM human BMP2 with or without increasing amounts of BMPR1a trap or BMPR1a-Fc (R&D Systems) for 24 hrs. at 37° C. The cells were then washed once with PBS and lysed with 50 µl X Reporter lysis buffer. The lysates were measured by a firefly luciferase reporter kit, according to the manufacturer's (Promega Corp). The activity is expressed as firefly RLU (see example FIG. 14).

Neutralization/Inhibition of TGF-β-Induced 4T1 Cell Invasion by TGF Binding Agents 4T1 cells (mouse mammary carcinoma, ATCC) were seeded onto BD BioCoat Matrigel invasion chambers (BD Biosciences) at $1 \times 10^5$ cells/chamber in DMEM containing no serum, without or with 100 pM TGF-β, and with 400 nM prototype (TβRII)$^2$ trap or TβRII-Fc. The cells were allowed to invade through the matrigel into the bottom chamber for 18 hrs at 37° C. The cells on the upper side of matrigel membrane were removed by scraping and invaded cells were stained/fixed with 0.2% crystal violet, 100% ethanol. The number of invaded cells was quantified for 4 fields of equal size via light microscopy. The example shown in FIG. 9C shows the average % invasion (relative to +TGF-β control) from 3 experiments.

Western Blot to Determine N-His (TβRII)$^2$ Protein Stability in serum

Equal amounts N-His (TβRII)$^2$ protein were incubated for 1-7 days at 37° C. in DMEM+10% fetal bovine serum. Equal aliquots were electopharesed in a 8% SDS-reducing gel followed by western blotting and probing with anti-TβRII antibody (R&D Systems). The result is shown in FIG. 11A.

TABLE 1

Linker characteristics for select examples of single-chain traps of TGF-β-family growth factors. Minimum number of residues required for linkage represents the structure-based linear distance for linkage (Å) divided by a factor of 2.5

| Single-chain trap | Targeted ligand(s) | Receptor ectodomain used | Reference structures (PDB entries) | Residues in "natural" linker | Linear distance (Å) for linkage | Minimum residues required for linkage |
|---|---|---|---|---|---|---|
| (ActR-IIa)$^2$ | BMP-7 | ActR-IIa-ED | 2GOO, 1LX5 | 28 | 70 | 28 |
| (ActR-IIb)$^2$ | Activin Myostatin | ActR-IIb-ED | 1S4Y, 1NYU | 25 | 45, 50 | 18 |
| (BMPR-Ia)$^2$ | BMP-2 | BMPR-Ia-ED | 2GOO, 1ES7 | 41 | 60 | 24 |
| (TβR-II)$^2$ | TGF-β1 TGF-β3 | TβR-II-ED | 1KTZ, 1PLO, 1M9Z | 35 | 80 | 32 |
| (TβR-IIb)$^2$ | TGF-β1 TGF-β3 | TβR-IIb-ED | 1KTZ, 1PLO, 1M9Z | 60 | 80 | 32 |

TABLE II

In addition to linkers disclosed elsewhere herein, the following polypeptide sequences may be useful as linkers or components thereof. These polypeptides may be useful when produced using either L- or D-amino acids. However, with respect to SEQ ID NOs 83 to 120, use of D-amino acids will frequently be preferred.

PFKVAGNNDTVIMDNNVSKQVHPPI (SEQ ID NO 119)

DPNSTNYEES (SEQ ID NO 83)

PFKVAGNNDTVIMDNNIHRLPHATRNCSPCIIEDKQAEMEVDSKQVHPPI (SEQ ID NO 84)

DPNSTNYEES (SEQ ID NO 85)

TAGPLLAA (SEQ ID NO 86)

EVPGLGPSSKVTTP (SEQ ID NO 87)

ESRGLIA (SEQ ID NO 88)

INYYPPKPTVPNSTPQTVEME (SEQ ID NO 89)

TEAEGRGS (SEQ ID NO 90)

TPATPPPEYTVEPGGAE (SEQ ID NO 91)

TABLE II-continued

In addition to linkers disclosed elsewhere herein, the following polypeptide sequences may be useful as linkers or components thereof. These polypeptides may be useful when produced using either L- or D-amino acids. However, with respect to SEQ ID NOs 83 to 120, use of D-amino acids will frequently be preferred.

DEPALTVGNESKKQDSDSKMGTGHLMSDLNQ (SEQ ID NO 92)

RISGDFFPGIVVP (SEQ ID NO 120)

PFKVAGNNDTVIMDNNVSKQVHPPIDPNSTNYEES (SEQ ID NO 93)

PFKVAGNNDTVIMDNNIHRLPHATRNCSPCIIEDKQAEMEVDSKQVHPPIDPNSTNYEES (SEQ ID NO 94)

TEAEGRGSTPATPPPEYTVEPGGAE (SEQ ID NO 95)

DEPALTVGNESKKQDSDSKMGTGHLMSDLNQRISGDFFPGIVVP (SEQ ID NO 96)

DEPALTVGNESKKQDSDSKMGTGHLMSDLNGRISGDFFPGIVVP (SEQ ID NO 97)

PFKVAGNNDTVIMDNNVSKQVHPPGDPNSTNYEES (SEQ ID NO 98)

TEAEGRGSTPATPPPEGTVEPGGAE (SEQ ID NO 99)

PFKVAGNNDTVIMDNNIHRLPHATRNCSPCIIEDKQAEMEVDSKQVHRGGDPNSTNYEES (SEQ ID NO 100)

PFKVAGNNDTVIMDNNVSKQVHPGGDPNSTNYEES (SEQ ID NO 101)

PFKVAGNNDTVIMDNNVSKQVHRGGDPNSTNYEES (SEQ ID NO 102)

PFKVAGNNDTVIMDNNIHRLPHATRNCSPCIIEDKQAEMGGGSGGGSGGGSPNSTNYEES (SEQ ID NO 103)

PFKVAGNNDTVIMDNNVSKGGSGGGSPNSTNYEES (SEQ ID NO 104)

PFKVAGNNDTVIMDGGGSGGGSGGGSPNSTNYEES (SEQ ID NO 105)

PFKVAGNNDTVIMDNNGGSGGGSGGGSGGGSGGGSGGGSGGGSKQVHPPIDPNSTNYEES (SEQ ID NO 106)

PFKVAGNNDTVIMDNNGGSGGGSGGGSGGGSGGGSGGGSGGGSGGGDPNSTNYEES (SEQ ID NO 107)

PFKVAGNNDTVIMDNNVSKQVHPPIDPNSTNYEES (SEQ ID NO 108)

PFKVAGNNDTVIMDNNVSKQVHPPIMDNNVSKQVHPPIDPNSTNYEES (SEQ ID NO 109)

PFKVAGNNDTVIMDNNVSKQVHPPNSTNYEES (SEQ ID NO 110)

PFKVAGNNDTVIMDNNVSKQVHPPIGGGGGGGGDPNSTNYEES (SEQ ID NO 111)

PFKVAGNNDTVIMDNNVSKQVHPPISGGGSGGGSGGGDPNSTNYEES (SEQ ID NO 112)

PFKVAGNNDTVIMDNNIHRLPHATRNCSPCIIEDKQAEMEVDSKQVHPPIDPNSTNYEES (SEQ ID NO 113)

PFKVAGNNDTVIMDNNIHRLPHATREDKQAEMEVDSKQVHPPIDPNSTNYEES (SEQ ID NO 114)

TEAEGRGSTPATPPPEYTVEPGGAE (SEQ ID NO 115)

TEAEGRGSGGGGGGGGGGTPATPPPEYTVEPGGAE (SEQ ID NO 116)

DEPALTVGNESKKQDSDSKMGTGHLMSDLNQRISGDFFPGIVVP (SEQ ID NO 117)

DEPALTVGNESKKQDSDSKMGTGHSDLNQRISGDPGIVVP (SEQ ID NO 118)

Also contemplated are nucleic acid sequences encoding such linkers.

---

We claim:

1. A multivalent binding agent with affinity for a member of the TGF-β superfamily, said agent comprising the general structure I:

($<$bd1$>$-linker1$)_k$-[{$<$bd1$>$linker2-$<$bd2$>$linker3$_f$}$_n$-($<$bd3$>$)$_m$-(linker4-$<$bd4$>$)$_d$]$_h$, where:
- n and h are independently greater than or equal to 1;
- d, f, m and k are independently equal to or greater than zero;
- bd1, bd2, bd3 and bd4 are polypeptide binding domains having an affinity for the same member of the TGF-β superfamily, with bd1, bd2, bd3, and bd4 being independently the same or different from each other; and,
- linker1, linker2, linker3 and linker4 are unstructured polypeptide sequences wherein one or more of linker1, linker2, linker3 and linker4 comprises the polypeptide sequence as set forth in SEQ ID NO: 37, SEQ ID NO: 38, SEQ ID NO: 39, SEQ ID NO: 40 or SEQ ID NO: 51;

wherein the number of amino acids in each linker is determined independently and is greater than or equal to X/2.5; where, X equals the shortest linear distance in A units between:
(a) the C-terminus of an isolated form of the binding domain that is located at the N-terminus of the linker and that is specifically bound to its ligand; and,
(b) the N-terminus of an isolated form of the binding domain that is located at the C-terminus of the linker and that is specifically bound to its ligand.

2. The agent of claim 1 wherein the member of the TGF-β superfamily to which the binding domains have affinity is selected from the group consisting of: TGF-β1, TGF-β2, TGF-β3, activin βA, activin βB, activin βC, activin βE, bone morphogenic protein (BMP) 2, BMP 3, BMP 4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin α, anti-Mullerian Hormone, Lefty 1, Lefty 2, arteman, Persephin and Neurturin.

3. The agent of claim 2 wherein the member of the TGF-β superfamily to which the binding domains have affinity is selected from the group consisting of: TGF-β1, TGF-β2, TGF-β3, BMP2, GDF 8, and activin.

4. The agent of claim 1 wherein each linker is between 25 and 60 amino acids in length.

5. The agent of claim 1 wherein bd4 is the same as bd1, bd2 is the same as bd3, h>0, and d, f, m, and n=1.

6. The agent of claim 1 wherein one of the linkers comprises SEQ ID NO: 37, SEQ ID NO: 38, SEQ ID NO: 39, SEQ ID NO: 40 or SEQ ID NO: 51 and the other linkers comprise one or more of SEQ ID NO 31-33, 35-42 or 49-74.

7. The agent of claim 1 wherein one or more of bd1, bd2, bd3, and bd4 is selected from one of SEQ ID NO 43-48.

8. The agent of claim 1 having the general structure V:

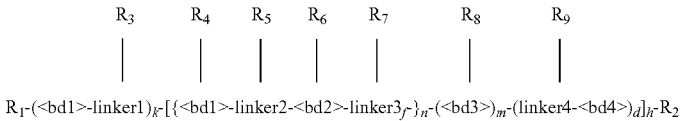

$R_1$-($<$bd1$>$-linker1$)_k$-[{$<$bd1$>$-linker2-$<$bd2$>$-linker3$_f$}$_n$-($<$bd3$>$)$_m$-(linker4-$<$bd4$>$)$_d$]$_h$-$R_2$ with $R_3, R_4, R_5, R_6, R_7, R_8, R_9$ as substituents wherein $R_1, R_2, R_3, R_4, R_5, R_6, R_7, R_8$, and $R_9$, may be the same or different, may not be present and when present, may independently be one or more of a fusion protein for targeting, a single domain antibody, a radiotherapy agent, an imaging agent, a fluorescent dye, a fluorescent protein tag, a cytotoxic agent for chemotherapy, a nano particle-based carrier, a polymer conjugated to drug, nanocarrier or imaging agent, a stabilizing agent, a drug, a nanocarrier, a support, and a dendrimer.

9. A method of modulating the response of a cell to a TGF-β superfamily member in its environment, said method comprising exposing the cell to an agent of claim 1.

10. A method of concentrating or purifying a ligand comprising contacting an agent of claim 1 with a sample containing the ligand.

11. A method of diagnosing a condition in a subject comprising administering an agent of claim 8 to the subject and detecting the presence of the agent in a body or portion thereof of the subject, wherein the agent comprises a radiotherapy agent, an imaging agent, a fluorescent dye or a fluorescent protein tag, and wherein the condition is characterized in whole or part by an abnormality in levels of one or more TGF-β superfamily members in the body or a portion thereof.

12. A method of targeting delivery of a compound to a site of interest within a body of a subject comprising administering an agent of claim 8 to the subject, wherein the agent comprises a fusion protein that targets the site of interest.

13. The agent of claim 1 comprising SEQ ID NO: 23.

14. The agent of claim 1 wherein the agent is a bivalent binding agent comprising general structure II:

<bd1>-linker-<bd2> where: bd1 and bd2 are polypeptide binding domains having an affinity for the same member of the TGF-β superfamily with bd1 and bd2 being independently the same or different from each other; and, linker comprises the polypeptide sequence as set forth in SEQ ID NO: 37, SEQ ID NO: 38, SEQ ID NO: 39, SEQ ID NO: 40 or SEQ ID NO: 51.

15. The agent of claim 14 wherein the member of the TGF-β superfamily to which the binding domains have affinity is TGF-β1, TGF-β2, TGF-β3, activin βA, activin βB, activin βC, activin βE, bone morphogenic protein (BMP) 2, BMP 3, BMP4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin α, anti-Mullerian Hormone, Lefty 1, Lefty 2, arteman, Persephin or Neurturin.

16. The agent of claim 14 wherein the member of the TGF-β superfamily to which the binding domains have affinity is TGF-β1, TGF-β2, TGF-β3, BMP2, GDF 8, or activin.

17. The agent of claim 14 wherein bd1 and bd2 are independently selected from the group consisting of SEQ ID NO 43, SEQ ID NO 44, SEQ ID NO 45, SEQ ID NO 46, SEQ ID NO 47 and SEQ ID NO 48.

18. The agent of claim 14 wherein bd1 and bd2 are the same.

19. The agent of claim 15 wherein bd1 and bd2 are the same.

20. The agent of claim 17 wherein bd1 and bd2 are the same.

21. The agent of claim 14 having the general structure:

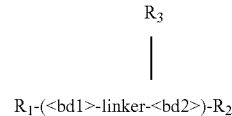

wherein $R_1$, $R_2$ and $R_3$ may be the same or different, may not be present and when present, may independently be one or more of a fusion protein for targeting, a single domain antibody, a radiotherapy agent, an imaging agent, a fluorescent dye, a fluorescent protein tag, a cytotoxic agent for chemotherapy, a nano particle-based carrier, a polymer-conjugated to drug, nanocarrier or imaging agent, a stabilizing agent, a drug, a nanocarrier, a support, and a dendrimer.

* * * * *

SEQUENCE LISTING

<160> NUMBER OF SEQ ID NOS: 121

<210> SEQ ID NO 1
<211> LENGTH: 54
<212> TYPE: DNA
<213> ORGANISM: Artificial Sequence
<220> FEATURE:
<223> OTHER INFORMATION: Synthetic Primer

<400> SEQUENCE: 1

```
gacaggatcc tagtgatgat ggtggtgatg gtcaggattg ctggtgttat attc    54
```

<210> SEQ ID NO 2
<211> LENGTH: 36
<212> TYPE: DNA
<213> ORGANISM: Artificial Sequence
<220> FEATURE:
<223> OTHER INFORMATION: Synthetic Primer

<400> SEQUENCE: 2

```
cacggcggcc gccacgttca gaagtcggtt aataac    36
```

<210> SEQ ID NO 3
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 3

```
Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg His Val Gln
                165                 170                 175

Lys Ser Val Asn Asn Asp Met Ile Val Thr Asp Asn Asn Gly Ala Val
            180                 185                 190

Lys Phe Pro Gln Leu Cys Lys Phe Cys Asp Val Arg Phe Ser Thr Cys
        195                 200                 205

Asp Asn Gln Lys Ser Cys Met Ser Asn Cys Ser Ile Thr Ser Ile Cys
    210                 215                 220

Glu Lys Pro Gln Glu Val Cys Val Ala Val Trp Arg Lys Asn Asp Glu
225                 230                 235                 240

Asn Ile Thr Leu Glu Thr Val Cys His Asp Pro Lys Leu Pro Tyr His
                245                 250                 255

Asp Phe Ile Leu Glu Asp Ala Ala Ser Pro Lys Cys Ile Met Lys Glu
            260                 265                 270

Lys Lys Lys Pro Gly Glu Thr Phe Phe Met Cys Ser Cys Ser Ser Asp
        275                 280                 285

Glu Cys Asn Asp Asn Ile Ile Phe Ser Glu Glu Tyr Asn Thr Ser Asn
```

|   | 290 | 295 | 300 |
|---|---|---|---|

Pro Asp His His His His His His
305          310

<210> SEQ ID NO 4
<211> LENGTH: 27
<212> TYPE: DNA
<213> ORGANISM: Artificial Sequence
<220> FEATURE:
<223> OTHER INFORMATION: Synthetic Primer

<400> SEQUENCE: 4
cctgacatcc caccgcaggt tcagaag                                27

<210> SEQ ID NO 5
<211> LENGTH: 27
<212> TYPE: DNA
<213> ORGANISM: Artificial Sequence
<220> FEATURE:
<223> OTHER INFORMATION: Synthetic Primer

<400> SEQUENCE: 5
gaacgtgcgg tgggatgtca ggattgc                                27

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
atacacttga gtgacaatga ca                                     22

<210> SEQ ID NO 7
<211> LENGTH: 28
<212> TYPE: DNA
<213> ORGANISM: Artificial Sequence
<220> FEATURE:
<223> OTHER INFORMATION: Synthetic Primer

<400> SEQUENCE: 7
aaaattccaa cacactactt tgcaatct                               28

<210> SEQ ID NO 8
<211> LENGTH: 45
<212> TYPE: DNA
<213> ORGANISM: Artificial Sequence
<220> FEATURE:
<223> OTHER INFORMATION: Synthetic Primer

<400> SEQUENCE: 8
ggatccttca acccgcgtat tccgccgcac gttcagaagt cggtt            45

<210> SEQ ID NO 9
<211> LENGTH: 36
<212> TYPE: DNA
<213> ORGANISM: Artificial Sequence
<220> FEATURE:
<223> OTHER INFORMATION: Synthetic Primer

<400> SEQUENCE: 9
gcgttcgaac tagtcaggat tgctggtgtt atattc                      36

<210> SEQ ID NO 10
<211> LENGTH: 323

```
<212> TYPE: PRT
<213> ORGANISM: Artificial Sequence
<220> FEATURE:
<223> OTHER INFORMATION: Synthetic Polypeptide

<400> SEQUENCE: 10

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His His His His His His Gly Gly Ser Phe
            35                  40                  45

Asn Pro Arg Ile Pro Pro His Val Gln Lys Ser Val Asn Asn Asp Met
    50                  55                  60

Ile Val Thr Asp Asn Asn Gly Ala Val Lys Phe Pro Gln Leu Cys Lys
65                  70                  75                  80

Phe Cys Asp Val Arg Phe Ser Thr Cys Asp Asn Gln Lys Ser Cys Met
                85                  90                  95

Ser Asn Cys Ser Ile Thr Ser Ile Cys Glu Lys Pro Gln Glu Val Cys
                100                 105                 110

Val Ala Val Trp Arg Lys Asn Asp Glu Asn Ile Thr Leu Glu Thr Val
                115                 120                 125

Cys His Asp Pro Lys Leu Pro Tyr His Asp Phe Ile Leu Glu Asp Ala
130                 135                 140

Ala Ser Pro Lys Cys Ile Met Lys Glu Lys Lys Pro Gly Glu Thr
145                 150                 155                 160

Phe Phe Met Cys Ser Cys Ser Asp Glu Cys Asn Asp Asn Ile Ile
                165                 170                 175

Phe Ser Glu Glu Tyr Asn Thr Ser Asn Pro Asp Ile Pro His Val
                180                 185                 190

Gln Lys Ser Val Asn Asn Asp Met Ile Val Thr Asp Asn Asn Gly Ala
                195                 200                 205

Val Lys Phe Pro Gln Leu Cys Lys Phe Cys Asp Val Arg Phe Ser Thr
                210                 215                 220

Cys Asp Asn Gln Lys Ser Cys Met Ser Asn Cys Ser Ile Thr Ser Ile
225                 230                 235                 240

Cys Glu Lys Pro Gln Glu Val Cys Val Ala Val Trp Arg Lys Asn Asp
                245                 250                 255

Glu Asn Ile Thr Leu Glu Thr Val Cys His Asp Pro Lys Leu Pro Tyr
                260                 265                 270

His Asp Phe Ile Leu Glu Asp Ala Ala Ser Pro Lys Cys Ile Met Lys
                275                 280                 285

Glu Lys Lys Pro Gly Glu Thr Phe Phe Met Cys Ser Cys Ser Ser
                290                 295                 300

Asp Glu Cys Asn Asp Asn Ile Ile Phe Ser Glu Glu Tyr Asn Thr Ser
305                 310                 315                 320

Asn Pro Asp

<210> SEQ ID NO 11
<211> LENGTH: 187
<212> TYPE: PRT
<213> ORGANISM: Artificial Sequence
<220> FEATURE:
<223> OTHER INFORMATION: Synthetic Polypeptide

<400> SEQUENCE: 11

Met Asn Phe Leu Leu Ser Trp Val His Trp Ser Leu Ala Leu Leu Leu
```

```
                1               5              10              15
            Tyr Leu His His Ala Lys Trp Ser Gln Ala Ala Pro Met Ala Glu Gly
                            20                  25                  30

Gly Gly Gln Asn His His His His His His His Gly Gly Ser Phe
                        35                  40                  45

Asn Pro Arg Ile Pro Pro His Val Gln Lys Ser Val Asn Asn Asp Met
             50                  55                  60

Ile Val Thr Asp Asn Asn Gly Ala Val Lys Phe Pro Gln Leu Cys Lys
             65                  70                  75                  80

Phe Cys Asp Val Arg Phe Ser Thr Cys Asp Asn Gln Lys Ser Cys Met
                            85                  90                  95

Ser Asn Cys Ser Ile Thr Ser Ile Cys Glu Lys Pro Gln Glu Val Cys
                        100                 105                 110

Val Ala Val Trp Arg Lys Asn Asp Glu Asn Ile Thr Leu Glu Thr Val
                        115                 120                 125

Cys His Asp Pro Lys Leu Pro Tyr His Asp Phe Ile Leu Glu Asp Ala
                        130                 135                 140

Ala Ser Pro Lys Cys Ile Met Lys Glu Lys Lys Pro Gly Glu Thr
            145                 150                 155                 160

Phe Phe Met Cys Ser Cys Ser Ser Asp Glu Cys Asn Asp Asn Ile Ile
                            165                 170                 175

Phe Ser Glu Glu Tyr Asn Thr Ser Asn Pro Asp
                        180                 185

<210> SEQ ID NO 12
<211> LENGTH: 54
<212> TYPE: DNA
<213> ORGANISM: Artificial Sequence
<220> FEATURE:
<223> OTHER INFORMATION: Synthetic Primer

<400> SEQUENCE: 12
gacaggatcc tagtgatgat ggtggtgatg gtcaggattg ctggtgttat attc       54

<210> SEQ ID NO 13
<211> LENGTH: 34
<212> TYPE: DNA
<213> ORGANISM: Artificial Sequence
<220> FEATURE:
<223> OTHER INFORMATION: Synthetic Primer

<400> SEQUENCE: 13
cacggcggcc gccacgttca gaagtcggat gtgg                             34

<210> SEQ ID NO 14
<211> LENGTH: 45
<212> TYPE: DNA
<213> ORGANISM: Artificial Sequence
<220> FEATURE:
<223> OTHER INFORMATION: Synthetic Primer

<400> SEQUENCE: 14
ggatccttca acccgcgtat tccgccgcac gttcagaagt cggtt                 45

<210> SEQ ID NO 15
<211> LENGTH: 36
<212> TYPE: DNA
<213> ORGANISM: Artificial Sequence
<220> FEATURE:
<223> OTHER INFORMATION: Synthetic Primer

<400> SEQUENCE: 15
```

```
gcgttcgaac tagtcaggat tgctggtgtt atattc                              36
```

<210> SEQ ID NO 16
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 16

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His His His His His Gly Gly Ser Phe
        35                  40                  45

Asn Pro Arg Ile Pro Pro His Val Gln Lys Ser Val Asn Asn Asp Met
    50                  55                  60

Ile Val Thr Asp Asn Asn Gly Ala Val Lys Phe Pro Gln Leu Cys Lys
65                  70                  75                  80

Phe Cys Asp Val Arg Phe Ser Thr Cys Asp Asn Gln Lys Ser Cys Met
                85                  90                  95

Ser Asn Cys Ser Ile Thr Ser Ile Cys Glu Lys Pro Gln Glu Val Cys
            100                 105                 110

Val Ala Val Trp Arg Lys Asn Asp Glu Asn Ile Thr Leu Glu Thr Val
        115                 120                 125

Cys His Asp Pro Lys Leu Pro Tyr His Asp Phe Ile Leu Glu Asp Ala
    130                 135                 140

Ala Ser Pro Lys Cys Ile Met Lys Glu Lys Lys Pro Gly Glu Thr
145                 150                 155                 160

Phe Phe Met Cys Ser Cys Ser Ser Asp Glu Cys Asn Asp Asn Ile Ile
                165                 170                 175

Phe Ser Glu Glu Tyr Asn Thr Ser Asn Pro Asp Ile Pro Pro His Val
            180                 185                 190

Gln Lys Ser Asp Val Glu Met Glu Ala Gln Lys Asp Glu Ile Ile Cys
        195                 200                 205

Pro Ser Cys Asn Arg Thr Ala His Pro Leu Arg His Ile Asn Asn Asp
    210                 215                 220

Met Ile Val Thr Asp Asn Asn Gly Ala Val Lys Phe Pro Gln Leu Cys
225                 230                 235                 240

Lys Phe Cys Asp Val Arg Phe Ser Thr Cys Asp Asn Gln Lys Ser Cys
                245                 250                 255

Met Ser Asn Cys Ser Ile Thr Ser Ile Cys Glu Lys Pro Gln Glu Val
            260                 265                 270

Cys Val Ala Val Trp Arg Lys Asn Asp Glu Asn Ile Thr Leu Glu Thr
        275                 280                 285

Val Cys His Asp Pro Lys Leu Pro Tyr His Asp Phe Ile Leu Glu Asp
    290                 295                 300

Ala Ala Ser Pro Lys Cys Ile Met Lys Glu Lys Lys Pro Gly Glu
305                 310                 315                 320

Thr Phe Phe Met Cys Ser Cys Ser Ser Asp Glu Cys Asn Asp Asn Ile
                325                 330                 335

Ile Phe Ser Glu Glu Tyr Asn Thr Ser Asn Pro Asp
            340                 345
```

<210> SEQ ID NO 17
<211> LENGTH: 99
<212> TYPE: DNA
<213> ORGANISM: Artificial Sequence
<220> FEATURE:
<223> OTHER INFORMATION: Synthetic Primer

<400> SEQUENCE: 17
cgcagatctg cggccgcatg acggcgccct gggtggccct cgccctcctc tggggatcgc    60
tgtgcgcagg atcaggatca gaacagaagc tgatcagcg                          99

<210> SEQ ID NO 18
<211> LENGTH: 99
<212> TYPE: DNA
<213> ORGANISM: Artificial Sequence
<220> FEATURE:
<223> OTHER INFORMATION: Synthetic Primer

<400> SEQUENCE: 18
ccgtgatcag cttctgttct gatcctgatc ctgcgcacag cgatcccag aggagggcga    60 gggccaccca gggcgccgtc atgcggccgc agatctggc                          99

<210> SEQ ID NO 19
<211> LENGTH: 59
<212> TYPE: DNA
<213> ORGANISM: Artificial Sequence
<220> FEATURE:
<223> OTHER INFORMATION: Synthetic Primer

<400> SEQUENCE: 19
ggcagatctc cgaggaagat ttactagggc gtggggaggc tgagacacgg gagtgcatc    59

<210> SEQ ID NO 20
<211> LENGTH: 30
<212> TYPE: DNA
<213> ORGANISM: Artificial Sequence
<220> FEATURE:
<223> OTHER INFORMATION: Synthetic Primer

<400> SEQUENCE: 20
ccgactagtg ggggctgtcg ggggtggctc                                    30

<210> SEQ ID NO 21
<211> LENGTH: 29
<212> TYPE: DNA
<213> ORGANISM: Artificial Sequence
<220> FEATURE:
<223> OTHER INFORMATION: Synthetic Primer

<400> SEQUENCE: 21
ccgactagtg ggcgtgggga ggctgagac                                     29

<210> SEQ ID NO 22
<211> LENGTH: 53
<212> TYPE: DNA
<213> ORGANISM: Artificial Sequence
<220> FEATURE:
<223> OTHER INFORMATION: Synthetic Primer

<400> SEQUENCE: 22
cgctggatcc ctaatggtga tgatggtgat gggtggggc tgtcgggggt ggc           53

<210> SEQ ID NO 23
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 23

```
Met Thr Ala Pro Trp Val Ala Leu Ala Leu Leu Trp Gly Ser Leu Cys
1               5                   10                  15

Ala Gly Ser Gly Ser Glu Gln Lys Leu Ile Ser Glu Glu Asp Leu Leu
            20                  25                  30

Gly Arg Gly Glu Ala Glu Thr Arg Glu Cys Ile Tyr Tyr Asn Ala Asn
        35                  40                  45

Trp Glu Leu Glu Arg Thr Asn Gln Ser Gly Leu Glu Arg Cys Glu Gly
    50                  55                  60

Glu Gln Asp Lys Arg Leu His Cys Tyr Ala Ser Trp Arg Asn Ser Ser
65                  70                  75                  80

Gly Thr Ile Glu Leu Val Lys Lys Gly Cys Trp Leu Asp Asp Phe Asn
                85                  90                  95

Cys Tyr Asp Arg Gln Glu Cys Val Ala Thr Glu Glu Asn Pro Gln Val
            100                 105                 110

Tyr Phe Cys Cys Cys Glu Gly Asn Phe Cys Asn Glu Arg Phe Thr His
        115                 120                 125

Leu Pro Glu Ala Gly Gly Pro Glu Val Thr Tyr Glu Pro Pro Pro Thr
    130                 135                 140

Ala Pro Thr Ser Gly Arg Gly Glu Ala Glu Thr Arg Glu Cys Ile Tyr
145                 150                 155                 160

Tyr Asn Ala Asn Trp Glu Leu Glu Arg Thr Asn Gln Ser Gly Leu Glu
                165                 170                 175

Arg Cys Glu Gly Glu Gln Asp Lys Arg Leu His Cys Tyr Ala Ser Trp
            180                 185                 190

Arg Asn Ser Ser Gly Thr Ile Glu Leu Val Lys Lys Gly Cys Trp Leu
        195                 200                 205

Asp Asp Phe Asn Cys Tyr Asp Arg Gln Glu Cys Val Ala Thr Glu Glu
    210                 215                 220

Asn Pro Gln Val Tyr Phe Cys Cys Cys Glu Gly Asn Phe Cys Asn Glu
225                 230                 235                 240

Arg Phe Thr His Leu Pro Glu Ala Gly Gly Pro Glu Val Thr Tyr Glu
                245                 250                 255

Pro Pro Pro Thr Ala Pro Thr His His His His His His
            260                 265
```

<210> SEQ ID NO 24
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 24

```
Met Thr Ala Pro Trp Val Ala Leu Ala Leu Leu Trp Gly Ser Leu Cys
1               5                   10                  15

Ala Gly Ser Gly Ser Glu Gln Lys Leu Ile Ser Glu Glu Asp Leu Leu
            20                  25                  30

Gly Arg Gly Glu Ala Glu Thr Arg Glu Cys Ile Tyr Tyr Asn Ala Asn
        35                  40                  45

Trp Glu Leu Glu Arg Thr Asn Gln Ser Gly Leu Glu Arg Cys Glu Gly
    50                  55                  60

Glu Gln Asp Lys Arg Leu His Cys Tyr Ala Ser Trp Arg Asn Ser Ser
65                  70                  75                  80
```

Gly Thr Ile Glu Leu Val Lys Lys Gly Cys Trp Leu Asp Asp Phe Asn
            85                  90                  95

Cys Tyr Asp Arg Gln Glu Cys Val Ala Thr Glu Glu Asn Pro Gln Val
        100                 105                 110

Tyr Phe Cys Cys Cys Glu Gly Asn Phe Cys Asn Glu Arg Phe Thr His
    115                 120                 125

Leu Pro Glu Ala Gly Gly Pro Glu Val Thr Tyr Glu Pro Pro Pro Thr
130                 135                 140

Ala Pro Thr His His His His His His
145                 150

<210> SEQ ID NO 25
<211> LENGTH: 33
<212> TYPE: DNA
<213> ORGANISM: Artificial Sequence
<220> FEATURE:
<223> OTHER INFORMATION: Synthetic Primer

<400> SEQUENCE: 25
gcgaagctta tgcctcagct atacatttac atc                             33

<210> SEQ ID NO 26
<211> LENGTH: 30
<212> TYPE: DNA
<213> ORGANISM: Artificial Sequence
<220> FEATURE:
<223> OTHER INFORMATION: Synthetic Primer

<400> SEQUENCE: 26
cggcctccgg atgctgccat caaaaaacgg                                 30

<210> SEQ ID NO 27
<211> LENGTH: 33
<212> TYPE: DNA
<213> ORGANISM: Artificial Sequence
<220> FEATURE:
<223> OTHER INFORMATION: Synthetic Primer

<400> SEQUENCE: 27
ccgcgcgccg gcagaatctg gatagtatgc ttc                             33

<210> SEQ ID NO 28
<211> LENGTH: 55
<212> TYPE: DNA
<213> ORGANISM: Artificial Sequence
<220> FEATURE:
<223> OTHER INFORMATION: Synthetic Primer

<400> SEQUENCE: 28
cgacaggatc ctagtgatga tggtggtgat gtcgaatgct gccatcaaaa aacgg     55

<210> SEQ ID NO 29
<211> LENGTH: 287
<212> TYPE: PRT
<213> ORGANISM: Artificial Sequence
<220> FEATURE:
<223> OTHER INFORMATION: Synthetic Polypeptide

<400> SEQUENCE: 29

Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

```
Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
 50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Ala Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Cys Arg Thr Asn
            115                 120                 125

Leu Cys Asn Gln Tyr Leu Gln Pro Thr Leu Pro Pro Val Val Ile Gly
            130                 135                 140

Pro Phe Phe Asp Gly Ser Ile Arg Gln Asn Leu Asp Ser Met Leu His
145                 150                 155                 160

Gly Thr Gly Met Lys Ser Asp Ser Asp Gln Lys Lys Ser Glu Asn Gly
                165                 170                 175

Val Thr Leu Ala Pro Glu Asp Thr Leu Pro Phe Leu Lys Cys Tyr Cys
                180                 185                 190

Ser Gly His Cys Pro Asp Asp Ala Ile Asn Asn Thr Cys Ile Thr Asn
            195                 200                 205

Gly His Cys Phe Ala Ile Ile Glu Glu Asp Asp Gln Gly Glu Thr Thr
            210                 215                 220

Leu Ala Ser Gly Cys Met Lys Tyr Glu Gly Ser Asp Phe Gln Cys Lys
225                 230                 235                 240

Asp Ser Pro Lys Ala Gln Leu Arg Arg Thr Ile Glu Cys Cys Arg Thr
                245                 250                 255

Asn Leu Cys Asn Gln Tyr Leu Gln Pro Thr Leu Pro Pro Val Val Ile
                260                 265                 270

Gly Pro Phe Phe Asp Gly Ser Ile Arg His His His His His
                275                 280                 285
```

<210> SEQ ID NO 30
<211> LENGTH: 158
<212> TYPE: PRT
<213> ORGANISM: Artificial Sequence
<220> FEATURE:
<223> OTHER INFORMATION: Synthetic Polypeptide

<400> SEQUENCE: 30

```
Met Pro Gln Leu Tyr Ile Tyr Ile Arg Leu Leu Gly Ala Tyr Leu Phe
 1               5                  10                  15

Ile Ile Ser Arg Val Gln Gly Gln Asn Leu Asp Ser Met Leu His Gly
                 20                  25                  30

Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
 50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Ala Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Cys Arg Thr Asn
```

```
                   115                 120                 125
Leu Cys Asn Gln Tyr Leu Gln Pro Thr Leu Pro Pro Val Val Ile Gly
        130                 135                 140

Pro Phe Phe Asp Gly Ser Ile Arg His His His His His His
145                 150                 155

<210> SEQ ID NO 31
<211> LENGTH: 25
<212> TYPE: PRT
<213> ORGANISM: Homo Sapiens

<400> SEQUENCE: 31

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 32
<211> LENGTH: 10
<212> TYPE: PRT
<213> ORGANISM: Homo Sapien

<400> SEQUENCE: 32

Ser Glu Glu Tyr Asn Thr Ser Asn Pro Asp
1               5                   10

<210> SEQ ID NO 33
<211> LENGTH: 50
<212> TYPE: PRT
<213> ORGANISM: Homo Sapiens

<400> SEQUENCE: 33

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro
    50

<210> SEQ ID NO 34
<211> LENGTH: 10
<212> TYPE: PRT
<213> ORGANISM: Homo Sapiens

<400> SEQUENCE: 34

Ser Glu Glu Tyr Asn Thr Ser Asn Pro Asp
1               5                   10

<210> SEQ ID NO 35
<211> LENGTH: 8
<212> TYPE: PRT
<213> ORGANISM: Homo Sapiens

<400> SEQUENCE: 35

Ala Ala Leu Leu Pro Gly Ala Thr
1               5

<210> SEQ ID NO 36
<211> LENGTH: 14
<212> TYPE: PRT
<213> ORGANISM: Homo Sapiens
```

```
<400> SEQUENCE: 36

Pro Thr Thr Val Lys Ser Ser Pro Gly Leu Gly Pro Val Glu
1               5                   10

<210> SEQ ID NO 37
<211> LENGTH: 7
<212> TYPE: PRT
<213> ORGANISM: Homo Sapiens

<400> SEQUENCE: 37

Ala Ile Leu Gly Arg Ser Glu
1               5

<210> SEQ ID NO 38
<211> LENGTH: 21
<212> TYPE: PRT
<213> ORGANISM: Homo Sapien

<400> SEQUENCE: 38

Glu Met Glu Val Thr Gln Pro Thr Ser Asn Pro Val Thr Pro Lys Pro
1               5                   10                  15

Pro Tyr Tyr Asn Ile
            20

<210> SEQ ID NO 39
<211> LENGTH: 8
<212> TYPE: PRT
<213> ORGANISM: Homo Sapiens

<400> SEQUENCE: 39

Ser Gly Arg Gly Glu Ala Glu Thr
1               5

<210> SEQ ID NO 40
<211> LENGTH: 17
<212> TYPE: PRT
<213> ORGANISM: Homo Sapiens

<400> SEQUENCE: 40

Glu Ala Gly Gly Pro Glu Val Thr Tyr Glu Pro Pro Pro Thr Ala Pro
1               5                   10                  15

Thr

<210> SEQ ID NO 41
<211> LENGTH: 31
<212> TYPE: PRT
<213> ORGANISM: Homo Sapiens

<400> SEQUENCE: 41

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp
            20                  25                  30

<210> SEQ ID NO 42
<211> LENGTH: 13
<212> TYPE: PRT
<213> ORGANISM: Homo Sapiens

<400> SEQUENCE: 42

Pro Val Val Ile Gly Pro Phe Phe Asp Gly Ser Ile Arg
1               5                   10
```

<210> SEQ ID NO 43
<211> LENGTH: 101
<212> TYPE: PRT
<213> ORGANISM: Homo Sapiens

<400> SEQUENCE: 43

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 44
<211> LENGTH: 101
<212> TYPE: PRT
<213> ORGANISM: Homo Sapiens

<400> SEQUENCE: 44

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 45
<211> LENGTH: 79
<212> TYPE: PRT
<213> ORGANISM: Homo Sapiens

<400> SEQUENCE: 45

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 46
<211> LENGTH: 92
<212> TYPE: PRT
<213> ORGANISM: Homo Sapiens

<400> SEQUENCE: 46

```
Thr Gln Glu Cys Leu Phe Phe Asn Ala Asn Trp Glu Lys Asp Arg Thr
1               5                   10                  15

Asn Gln Thr Gly Val Glu Pro Cys Tyr Gly Asp Lys Asp Lys Arg Arg
            20                  25                  30

His Cys Phe Ala Thr Trp Lys Asn Ile Ser Gly Ser Ile Glu Ile Val
        35                  40                  45

Lys Gln Gly Cys Trp Leu Asp Asp Ile Asn Cys Tyr Asp Arg Thr Asp
    50                  55                  60

Cys Val Glu Lys Lys Asp Ser Pro Glu Val Tyr Phe Cys Cys Cys Glu
65                  70                  75                  80

Gly Asn Met Cys Asn Glu Lys Phe Ser Tyr Phe Pro
                85                  90
```

<210> SEQ ID NO 47
<211> LENGTH: 108
<212> TYPE: PRT
<213> ORGANISM: Homo sapiens

<400> SEQUENCE: 47

```
Arg Glu Cys Ile Tyr Tyr Asn Ala Asn Trp Glu Leu Glu Arg Thr Asn
1               5                   10                  15

Gln Ser Gly Leu Glu Arg Cys Glu Gly Glu Gln Asp Lys Arg Leu His
            20                  25                  30

Cys Tyr Ala Ser Trp Arg Asn Ser Ser Gly Thr Ile Glu Leu Val Lys
        35                  40                  45

Lys Gly Cys Trp Leu Asp Asp Phe Asn Cys Tyr Asp Arg Gln Glu Cys
    50                  55                  60

Val Ala Thr Glu Glu Asn Pro Gln Val Tyr Phe Cys Cys Cys Glu Gly
65                  70                  75                  80

Asn Phe Cys Asn Glu Arg Phe Thr His Leu Pro Glu Ala Gly Gly Pro
                85                  90                  95

Glu Val Thr Tyr Glu Pro Pro Pro Thr Ala Pro Thr
            100                 105
```

<210> SEQ ID NO 48
<211> LENGTH: 98
<212> TYPE: PRT
<213> ORGANISM: Homo Sapiens

<400> SEQUENCE: 48

```
Thr Leu Pro Phe Leu Lys Cys Tyr Cys Ser Gly His Cys Pro Asp Asp
1               5                   10                  15

Ala Ile Asn Asn Thr Cys Ile Thr Asn Gly His Cys Phe Ala Ile Ile
            20                  25                  30

Glu Glu Asp Asp Gln Gly Glu Thr Thr Leu Ala Ser Gly Cys Met Lys
        35                  40                  45

Tyr Glu Gly Ser Asp Phe Gln Cys Lys Asp Ser Pro Lys Ala Gln Leu
    50                  55                  60

Arg Arg Thr Ile Glu Cys Cys Arg Thr Asn Leu Cys Asn Gln Tyr Leu
65                  70                  75                  80

Gln Pro Thr Leu Pro Pro Val Val Ile Gly Pro Phe Phe Asp Gly Ser
```

Ile Arg

<210> SEQ ID NO 49
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 49

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 50
<211> LENGTH: 60
<212> TYPE: PRT
<213> ORGANISM: Artificial sequence
<220> FEATURE:
<223> OTHER INFORMATION: synthetic polypeptide

<400> SEQUENCE: 50

Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 51
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 51

Glu Ala Gly Gly Pro Glu Val Thr Tyr Glu Pro Pro Pro Thr Ala Pro
1               5                   10                  15

Thr Ser Gly Arg Gly Glu Ala Glu Thr
            20                  25

<210> SEQ ID NO 52
<211> LENGTH: 44
<212> TYPE: PRT
<213> ORGANISM: Artificial Sequence
<220> FEATURE:
<223> OTHER INFORMATION: synthetic polypeptide

<400> SEQUENCE: 52

Pro Val Val Ile Gly Pro Phe Phe Asp Gly Ser Ile Arg Gln Asn Leu
1               5                   10                  15

Asp Ser Met Leu His Gly Thr Gly Met Lys Ser Asp Ser Asp Gln Lys
            20                  25                  30

Lys Ser Glu Asn Gly Val Thr Leu Ala Pro Glu Asp
        35                  40

-continued

<210> SEQ ID NO 53
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 53

Pro Val Val Ile Gly Pro Phe Phe Asp Gly Ser Ile Arg Gly Asn Leu
1               5                   10                  15

Asp Ser Met Leu His Gly Thr Gly Met Lys Ser Asp Ser Asp Gln Lys
            20                  25                  30

Lys Ser Glu Asn Gly Val Thr Leu Ala Pro Glu Asp
        35                  40

<210> SEQ ID NO 54
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 54

Ser Glu Glu Tyr Asn Thr Ser Asn Pro Asp Gly Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 55
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 55

Glu Ala Gly Gly Pro Glu Val Thr Gly Glu Pro Pro Thr Ala Pro
1               5                   10                  15

Thr Ser Gly Arg Gly Glu Ala Glu Thr
            20                  25

<210> SEQ ID NO 56
<211> LENGTH: 60
<212> TYPE: PRT
<213> ORGANISM: Artificial sequence
<220> FEATURE:
<223> OTHER INFORMATION: synthetic polypeptide

<400> SEQUENCE: 56

Ser Glu Glu Tyr Asn Thr Ser Asn Pro Asp Gly Gly Arg His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 57
<211> LENGTH: 35
<212> TYPE: PRT

```
<213> ORGANISM: Artificial Sequence
<220> FEATURE:
<223> OTHER INFORMATION: Synthetic Polypeptide

<400> SEQUENCE: 57

Ser Glu Glu Tyr Asn Thr Ser Asn Pro Asp Gly Gly Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 58
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 58

Ser Glu Glu Tyr Asn Thr Ser Asn Pro Asp Gly Gly Arg His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 59
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 59

Ser Glu Glu Tyr Asn Thr Ser Asn Pro Ser Gly Gly Gly Ser Gly Gly
1               5                   10                  15

Gly Ser Gly Gly Gly Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 60
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 60

Ser Glu Glu Tyr Asn Thr Ser Asn Pro Ser Gly Gly Gly Ser Gly Gly
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 61
<211> LENGTH: 35
<212> TYPE: PRT
<213> ORGANISM: Artificial Sequence
```

<220> FEATURE:
<223> OTHER INFORMATION: Synthetic Polypeptide

<400> SEQUENCE: 61

Ser Glu Glu Tyr Asn Thr Ser Asn Pro Ser Gly Gly Gly Ser Gly Gly
1               5                   10                  15

Gly Ser Gly Gly Gly Asp Met Ile Val Thr Asp Asn Asn Gly Ala Val
            20                  25                  30

Lys Phe Pro
        35

<210> SEQ ID NO 62
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 62

Ser Glu Glu Tyr Asn Thr Ser Asn Pro Asp Ile Pro Pro His Val Gln
1               5                   10                  15

Lys Ser Gly Gly Gly Ser Gly Gly Gly Ser Gly Gly Gly Ser Gly Gly
            20                  25                  30

Gly Ser Gly Gly Gly Ser Gly Gly Gly Ser Gly Gly Asn Asn Asp Met
            35                  40                  45

Ile Val Thr Asp Asn Asn Gly Ala Val Lys Phe Pro
        50                  55                  60

<210> SEQ ID NO 63
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 63

Ser Glu Glu Tyr Asn Thr Ser Asn Pro Asp Gly Gly Gly Ser Gly Gly
1               5                   10                  15

Gly Ser Gly Gly Gly Ser Gly Gly Gly Ser Gly Gly Gly Ser Gly Gly
            20                  25                  30

Gly Ser Gly Gly Gly Ser Gly Gly Gly Ser Gly Gly Asn Asn Asp Met
            35                  40                  45

Ile Val Thr Asp Asn Asn Gly Ala Val Lys Phe Pro
        50                  55                  60

<210> SEQ ID NO 64
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 64

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 65
<211> LENGTH: 48

```
<212> TYPE: PRT
<213> ORGANISM: Artificial Sequence
<220> FEATURE:
<223> OTHER INFORMATION: Synthetic Polypeptide

<400> SEQUENCE: 65

Ser Glu Glu Tyr Asn Thr Ser Asn Pro Asp Ile Pro Pro His Val Gln
1               5                   10                  15

Lys Ser Val Asn Asn Asp Met Ile Pro Pro His Val Gln Lys Ser Val
            20                  25                  30

Asn Asn Asp Met Ile Val Thr Asp Asn Asn Gly Ala Val Lys Phe Pro
        35                  40                  45

<210> SEQ ID NO 66
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 66

Ser Glu Glu Tyr Asn Thr Ser Asn Pro Pro His Val Gln Lys Ser Val
1               5                   10                  15

Asn Asn Asp Met Ile Val Thr Asp Asn Asn Gly Ala Val Lys Phe Pro
            20                  25                  30

<210> SEQ ID NO 67
<211> LENGTH: 43
<212> TYPE: PRT
<213> ORGANISM: Artificial Sequence
<220> FEATURE:
<223> OTHER INFORMATION: synthetic polypeptide

<400> SEQUENCE: 67

Ser Glu Glu Tyr Asn Thr Ser Asn Pro Asp Gly Gly Gly Gly Gly Gly
1               5                   10                  15

Gly Gly Ile Pro Pro His Val Gln Lys Ser Val Asn Asn Asp Met Ile
            20                  25                  30

Val Thr Asp Asn Asn Gly Ala Val Lys Phe Pro
        35                  40

<210> SEQ ID NO 68
<211> LENGTH: 47
<212> TYPE: PRT
<213> ORGANISM: Artificial sequence
<220> FEATURE:
<223> OTHER INFORMATION: synthetic polypeptide

<400> SEQUENCE: 68

Ser Glu Glu Tyr Asn Thr Ser Asn Pro Asp Gly Gly Gly Ser Gly Gly
1               5                   10                  15

Gly Ser Gly Gly Gly Ser Ile Pro Pro His Val Gln Lys Ser Val Asn
            20                  25                  30

Asn Asp Met Ile Val Thr Asp Asn Asn Gly Ala Val Lys Phe Pro
        35                  40                  45

<210> SEQ ID NO 69
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 69
```

```
Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
            35                  40                  45

Ile Val Thr Asp Asn Asn Gly Ala Val Lys Phe Pro
        50                  55                  60

<210> SEQ ID NO 70
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 70

Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Arg Thr Ala His
            20                  25                  30

Pro Leu Arg His Ile Asn Asn Asp Met Ile Val Thr Asp Asn Asn Gly
            35                  40                  45

Ala Val Lys Phe Pro
        50

<210> SEQ ID NO 71
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 71

Glu Ala Gly Gly Pro Glu Val Thr Tyr Glu Pro Pro Thr Ala Pro
1               5                   10                  15

Thr Ser Gly Arg Gly Glu Ala Glu Thr
            20                  25

<210> SEQ ID NO 72
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 72

Glu Ala Gly Gly Pro Glu Val Thr Tyr Glu Pro Pro Thr Ala Pro
1               5                   10                  15

Thr Gly Gly Gly Gly Gly Gly Gly Gly Ser Gly Arg Gly Glu
            20                  25                  30

Ala Glu Thr
        35

<210> SEQ ID NO 73
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 73

Pro Val Val Ile Gly Pro Phe Phe Asp Gly Ser Ile Arg Gln Asn Leu
```

```
                1               5                   10                  15
Asp Ser Met Leu His Gly Thr Gly Met Lys Ser Asp Ser Asp Gln Lys
                    20                  25                  30

Lys Ser Glu Asn Gly Val Thr Leu Ala Pro Glu Asp
        35                  40
```

<210> SEQ ID NO 74
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 74

```
Pro Val Val Ile Gly Pro Asp Gly Ser Ile Arg Gln Asn Leu Asp Ser
1               5                   10                  15

His Gly Thr Gly Met Lys Ser Asp Ser Asp Gln Lys Lys Ser Glu Asn
                20                  25                  30

Gly Val Thr Leu Ala Pro Glu Asp
        35                  40
```

<210> SEQ ID NO 75
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 75

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asp Asn Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
    130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp
    210
```

<210> SEQ ID NO 76
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 76

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Gly Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
    130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp
    210
```

<210> SEQ ID NO 77
<211> LENGTH: 360
<212> TYPE: PRT
<213> ORGANISM: Artificial Sequence
<220> FEATURE:
<223> OTHER INFORMATION: Synthetic Polypeptide

<400> SEQUENCE: 77

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asp Asn Asn Gly
                85                  90                  95

Ala Val Lys Phe Pro Gln Leu Cys Lys Phe Cys Asp Val Arg Phe Ser
```

```
                    100                 105                 110
Thr Cys Asp Asn Gln Lys Ser Cys Met Ser Asn Cys Ser Ile Thr Ser
            115                 120                 125
Ile Cys Glu Lys Pro Gln Glu Val Cys Val Ala Val Trp Arg Lys Asn
            130                 135                 140
Asp Glu Asn Ile Thr Leu Glu Thr Val Cys His Asp Pro Lys Leu Pro
145                 150                 155                 160
Tyr His Asp Phe Ile Leu Glu Asp Ala Ala Ser Pro Lys Cys Ile Met
                165                 170                 175
Lys Glu Lys Lys Lys Pro Gly Glu Thr Phe Phe Met Cys Ser Cys Ser
            180                 185                 190
Ser Asp Glu Cys Asn Asp Asn Ile Ile Phe Ser Glu Glu Tyr Asn Thr
            195                 200                 205
Ser Asn Pro Asp Gly Gly Ser Gly Gly Ser Gly Gly Gly Ser
            210                 215                 220
Ile Pro Pro His Val Gln Lys Ser Val Asn Asn Asp Met Ile Val Thr
225                 230                 235                 240
Asp Asn Asn Gly Ala Val Lys Phe Pro Gln Leu Cys Lys Phe Cys Asp
                245                 250                 255
Val Arg Phe Ser Thr Cys Asp Asn Gln Lys Ser Cys Met Ser Asn Cys
            260                 265                 270
Ser Ile Thr Ser Ile Cys Glu Lys Pro Gln Glu Val Cys Val Ala Val
            275                 280                 285
Trp Arg Lys Asn Asp Glu Asn Ile Thr Leu Glu Thr Val Cys His Asp
            290                 295                 300
Pro Lys Leu Pro Tyr His Asp Phe Ile Leu Glu Asp Ala Ala Ser Pro
305                 310                 315                 320
Lys Cys Ile Met Lys Glu Lys Lys Lys Pro Gly Glu Thr Phe Phe Met
                325                 330                 335
Cys Ser Cys Ser Ser Asp Glu Cys Asn Asp Asn Ile Ile Phe Ser Glu
            340                 345                 350
Glu Tyr Asn Thr Ser Asn Pro Asp
            355                 360

<210> SEQ ID NO 78
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 78

Ala Ala Leu Leu Pro Gly Ala Thr Ala Leu Gln Cys Phe Cys His Leu
1               5                   10                  15
Cys Thr Lys Asp Asn Phe Thr Cys Val Thr Asp Gly Leu Cys Phe Val
            20                  25                  30
Ser Val Thr Glu Thr Thr Asp Lys Val Ile His Asn Ser Met Cys Ile
            35                  40                  45
Ala Glu Ile Asp Leu Ile Pro Arg Asp Arg Pro Phe Val Cys Ala Pro
        50                  55                  60
Ser Ser Lys Thr Gly Ser Val Thr Thr Thr Tyr Cys Cys Asn Gln Asp
65              70                  75                  80
His Cys Asn Lys Ile Glu Leu Pro Thr Thr Val Thr Asp Asn Asn Gly
                85                  90                  95
Ala Val Lys Phe Pro Gln Leu Cys Lys Phe Cys Asp Val Arg Phe Ser
            100                 105                 110
```

```
Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp Ile Pro Pro His Val Gln Lys Ser Asp Val Glu Met
    210                 215                 220

Glu Ala Gln Lys Asp Glu Ile Ile Cys Pro Ser Cys Asn Arg Thr Ala
225                 230                 235                 240

His Pro Leu Arg His Ile Asn Asn Asp Met Ile Val Thr Asp Asn Asn
                245                 250                 255

Gly Ala Val Lys Phe Pro Gln Leu Cys Lys Phe Cys Asp Val Arg Phe
            260                 265                 270

Ser Thr Cys Asp Asn Gln Lys Ser Cys Met Ser Asn Cys Ser Ile Thr
        275                 280                 285

Ser Ile Cys Glu Lys Pro Gln Glu Val Cys Val Ala Val Trp Arg Lys
    290                 295                 300

Asn Asp Glu Asn Ile Thr Leu Glu Thr Val Cys His Asp Pro Lys Leu
305                 310                 315                 320

Pro Tyr His Asp Phe Ile Leu Glu Asp Ala Ala Ser Pro Lys Cys Ile
                325                 330                 335

Met Lys Glu Lys Lys Lys Pro Gly Glu Thr Phe Phe Met Cys Ser Cys
            340                 345                 350

Ser Ser Asp Glu Cys Asn Asp Asn Ile Ile Phe Ser Glu Glu Tyr Asn
        355                 360                 365

Thr Ser Asn Pro Asp
    370

<210> SEQ ID NO 79
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 79

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asp Asn Asn Gly
                85                  90                  95
```

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp Gly Gly Ser Gly Gly Ser Gly Gly Gly Ser
210                 215                 220

Gly Gly Gly Ser Gly Gly Ser Gly Gly Gly Ser Gly Gly Gly Ser
225                 230                 235                 240

Gly Gly Gly Ser Ala Leu Gln Cys Phe Cys His Leu Cys Thr Lys Asp
                245                 250                 255

Asn Phe Thr Cys Val Thr Asp Gly Leu Cys Phe Val Ser Val Thr Glu
            260                 265                 270

Thr Thr Asp Lys Val Ile His Asn Ser Met Cys Ile Ala Glu Ile Asp
        275                 280                 285

Leu Ile Pro Arg Asp Arg Pro Phe Val Cys Ala Pro Ser Ser Lys Thr
290                 295                 300

Gly Ser Val Thr Thr Thr Tyr Cys Cys Asn Gln Asp His Cys Asn Lys
305                 310                 315                 320

Ile Glu Leu Pro Thr Thr Val Thr Asp Asn Asn Gly Ala Val Lys Phe
                325                 330                 335

Pro Gln Leu Cys Lys Phe Cys Asp Val Arg Phe Ser Thr Cys Asp Asn
            340                 345                 350

Gln Lys Ser Cys Met Ser Asn Cys Ser Ile Thr Ser Ile Cys Glu Lys
        355                 360                 365

Pro Gln Glu Val Cys Val Ala Val Trp Arg Lys Asn Asp Glu Asn Ile
370                 375                 380

Thr Leu Glu Thr Val Cys His Asp Pro Lys Leu Pro Tyr His Asp Phe
385                 390                 395                 400

Ile Leu Glu Asp Ala Ala Ser Pro Lys Cys Ile Met Lys Glu Lys Lys
                405                 410                 415

Lys Pro Gly Glu Thr Phe Phe Met Cys Ser Cys Ser Ser Asp Glu Cys
            420                 425                 430

Asn Asp Asn Ile Ile Phe Ser Glu Glu Tyr Asn Thr Ser Asn Pro Asp
        435                 440                 445

<210> SEQ ID NO 80
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 80

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val

-continued

```
                 20                  25                  30
Ser Val Thr Glu Thr Thr Asp Lys Val Ile His Asn Ser Met Cys Ile
                 35                  40                  45
Ala Glu Ile Asp Leu Ile Pro Arg Asp Arg Pro Phe Val Cys Ala Pro
             50                  55                  60
Ser Ser Lys Thr Gly Ser Val Thr Thr Thr Tyr Cys Cys Asn Gln Asp
65                  70                  75                  80
His Cys Asn Lys Ile Glu Leu Gly Gly Gly Gly Gly Gly Gly Asn Gly
                     85                  90                  95
Ala Val Lys Phe Pro Gln Leu Cys Lys Phe Cys Asp Val Arg Phe Ser
                100                 105                 110
Thr Cys Asp Asn Gln Lys Ser Cys Met Ser Asn Cys Ser Ile Thr Ser
            115                 120                 125
Ile Cys Glu Lys Pro Gln Glu Val Cys Val Ala Val Trp Arg Lys Asn
        130                 135                 140
Asp Glu Asn Ile Thr Leu Glu Thr Val Cys His Asp Pro Lys Leu Pro
145                 150                 155                 160
Tyr His Asp Phe Ile Leu Glu Asp Ala Ala Ser Pro Lys Cys Ile Met
                165                 170                 175
Lys Glu Lys Lys Lys Pro Gly Glu Thr Phe Phe Met Cys Ser Cys Ser
                180                 185                 190
Ser Asp Glu Cys Asn Asp Asn Ile Ile Phe Ser Glu Glu Tyr Asn Thr
            195                 200                 205
Ser Asn Pro Asp Gly Gly Gly Ser Gly Gly Gly Ser Gly Gly Gly Ser
        210                 215                 220
Gly Gly Gly Ser Gly Gly Gly Ser Gly Gly Gly Ser Gly Gly Gly Ser
225                 230                 235                 240
Gly Gly Gly Ser Ala Leu Gln Cys Phe Cys His Leu Cys Thr Lys Asp
                245                 250                 255
Asn Phe Thr Cys Val Thr Asp Gly Leu Cys Phe Val Ser Val Thr Glu
                260                 265                 270
Thr Thr Asp Lys Val Ile His Asn Ser Met Cys Ile Ala Glu Ile Asp
            275                 280                 285
Leu Ile Pro Arg Asp Arg Pro Phe Val Cys Ala Pro Ser Ser Lys Thr
        290                 295                 300
Gly Ser Val Thr Thr Thr Tyr Cys Cys Asn Gln Asp His Cys Asn Lys
305                 310                 315                 320
Ile Glu Leu Gly Gly Gly Gly Gly Gly Asn Gly Ala Val Lys Phe
                325                 330                 335
Pro Gln Leu Cys Lys Phe Cys Asp Val Arg Phe Ser Thr Cys Asp Asn
                340                 345                 350
Gln Lys Ser Cys Met Ser Asn Cys Ser Ile Thr Ser Ile Cys Glu Lys
            355                 360                 365
Pro Gln Glu Val Cys Val Ala Val Trp Arg Lys Asn Asp Glu Asn Ile
        370                 375                 380
Thr Leu Glu Thr Val Cys His Asp Pro Lys Leu Pro Tyr His Asp Phe
385                 390                 395                 400
Ile Leu Glu Asp Ala Ala Ser Pro Lys Cys Ile Met Lys Glu Lys Lys
                405                 410                 415
Lys Pro Gly Glu Thr Phe Phe Met Cys Ser Cys Ser Ser Asp Glu Cys
                420                 425                 430
Asn Asp Asn Ile Ile Phe Ser Glu Glu Tyr Asn Thr Ser Asn Pro Asp
            435                 440                 445
```

-continued

```
<210> SEQ ID NO 81
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 81

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
        50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Gly Asn Gly
                85                  90                  95

Ala Val Lys Phe Pro Gln Leu Cys Lys Phe Cys Asp Val Arg Phe Ser
                100                 105                 110

Thr Cys Asp Asn Gln Lys Ser Cys Met Ser Asn Cys Ser Ile Thr Ser
            115                 120                 125

Ile Cys Glu Lys Pro Gln Glu Val Cys Val Ala Val Trp Arg Lys Asn
        130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
                180                 185                 190

Ser Asp Glu Cys Asn Asp Asn Ile Ile Phe Ser Glu Glu Tyr Asn Thr
            195                 200                 205

Ser Asn Pro Asp Gly Gly Gly Ser Gly Gly Gly Ser Gly Gly Gly Ser
        210                 215                 220

Ile Pro Pro His Val Gln Lys Ser Val Asn Asn Asp Met Ile Val Thr
225                 230                 235                 240

Asp Asn Asn Gly Ala Val Lys Phe Pro Gln Leu Cys Lys Phe Cys Asp
                245                 250                 255

Val Arg Phe Ser Thr Cys Asp Asn Gln Lys Ser Cys Met Ser Asn Cys
                260                 265                 270

Ser Ile Thr Ser Ile Cys Glu Lys Pro Gln Glu Val Cys Val Ala Val
            275                 280                 285

Trp Arg Lys Asn Asp Glu Asn Ile Thr Leu Glu Thr Val Cys His Asp
        290                 295                 300

Pro Lys Leu Pro Tyr His Asp Phe Ile Leu Glu Asp Ala Ala Ser Pro
305                 310                 315                 320

Lys Cys Ile Met Lys Glu Lys Lys Lys Pro Gly Glu Thr Phe Phe Met
                325                 330                 335

Cys Ser Cys Ser Ser Asp Glu Cys Asn Asp Asn Ile Ile Phe Ser Glu
            340                 345                 350

Glu Tyr Asn Thr Ser Asn Pro Asp Gly Gly Gly Ser Gly Gly Gly Ser
        355                 360                 365

Gly Gly Gly Ser Gly Gly Gly Ser Gly Gly Gly Ser Ala Leu Gln Cys
```

```
              370              375              380
Phe Cys His Leu Cys Thr Lys Asp Asn Phe Thr Cys Val Thr Asp Gly
385                  390                  395                  400

Leu Cys Phe Val Ser Val Thr Glu Thr Thr Asp Lys Val Ile His Asn
                405                  410                  415

Ser Met Cys Ile Ala Glu Ile Asp Leu Ile Pro Arg Asp Arg Pro Phe
            420                  425                  430

Val Cys Ala Pro Ser Ser Lys Thr Gly Ser Val Thr Thr Thr Tyr Cys
        435                  440                  445

Cys Asn Gln Asp His Cys Asn Lys Ile Glu Leu Pro Thr Thr Val Lys
    450                  455                  460

Ser Ser Pro Gly Leu Gly Pro Val Glu
465                  470

<210> SEQ ID NO 82
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 82

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
        50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Gly Gly Ser Gly Gly Ser Gly Gly Gly
            100                 105                 110

Ser Gly Gly Gly Ser Gly Gly Gly Ser Ala Leu Gln Cys Phe Cys His
        115                 120                 125

Leu Cys Thr Lys Asp Asn Phe Thr Cys Val Thr Asp Gly Leu Cys Phe
130                 135                 140

Val Ser Val Thr Glu Thr Thr Asp Lys Val Ile His Asn Ser Met Cys
145                 150                 155                 160

Ile Ala Glu Ile Asp Leu Ile Pro Arg Asp Arg Pro Phe Val Cys Ala
                165                 170                 175

Pro Ser Ser Lys Thr Gly Ser Val Thr Thr Thr Tyr Cys Cys Asn Gln
            180                 185                 190

Asp His Cys Asn Lys Ile Glu Leu Gly Gly Gly Gly Gly Gly Asn
        195                 200                 205

Gly Ala Val Lys Phe Pro Gln Leu Cys Lys Phe Cys Asp Val Arg Phe
210                 215                 220

Ser Thr Cys Asp Asn Gln Lys Ser Cys Met Ser Asn Cys Ser Ile Thr
225                 230                 235                 240

Ser Ile Cys Glu Lys Pro Gln Glu Val Cys Val Ala Val Trp Arg Lys
                245                 250                 255

Asn Asp Glu Asn Ile Thr Leu Glu Thr Val Cys His Asp Pro Lys Leu
            260                 265                 270
```

```
Pro Tyr His Asp Phe Ile Leu Glu Asp Ala Ala Ser Pro Lys Cys Ile
            275                 280                 285

Met Lys Glu Lys Lys Pro Gly Glu Thr Phe Phe Met Cys Ser Cys
    290                 295                 300

Ser Ser Asp Glu Cys Asn Asp Ile Ile Phe Ser Glu Glu Tyr Asn
305                 310                 315                 320

Thr Ser Asn Pro Asp Gly Gly Ser Gly Gly Ser Gly Gly Gly
                325                 330                 335

Ser Ile Pro Pro His Val Gln Lys Ser Val Asn Asp Met Ile Val
            340                 345                 350

Thr Asp Asn Asn Gly Ala Val Lys Phe Pro Gln Leu Cys Lys Phe Cys
            355                 360                 365

Asp Val Arg Phe Ser Thr Cys Asp Asn Gln Lys Ser Cys Met Ser Asn
370                 375                 380

Cys Ser Ile Thr Ser Ile Cys Glu Lys Pro Gln Glu Val Cys Val Ala
385                 390                 395                 400

Val Trp Arg Lys Asn Asp Glu Asn Ile Thr Leu Glu Thr Val Cys His
                405                 410                 415

Asp Pro Lys Leu Pro Tyr His Asp Phe Ile Leu Glu Asp Ala Ala Ser
            420                 425                 430

Pro Lys Cys Ile Met Lys Glu Lys Lys Pro Gly Glu Thr Phe Phe
                435                 440                 445

Met Cys Ser Cys Ser Ser Asp Glu Cys Asn Asp Ile Ile Phe Ser
    450                 455                 460

Glu Glu Tyr Asn Thr Ser Asn Pro Asp
465                 470

<210> SEQ ID NO 83
<211> LENGTH: 10
<212> TYPE: PRT
<213> ORGANISM: Artificial sequence
<220> FEATURE:
<223> OTHER INFORMATION: synthetic linker

<400> SEQUENCE: 83

Asp Pro Asn Ser Thr Asn Tyr Glu Glu Ser
1               5                   10

<210> SEQ ID NO 84
<211> LENGTH: 50
<212> TYPE: PRT
<213> ORGANISM: Artificial sequence
<220> FEATURE:
<223> OTHER INFORMATION: Synthetic linker

<400> SEQUENCE: 84

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile
    50

<210> SEQ ID NO 85
<211> LENGTH: 10
<212> TYPE: PRT
<213> ORGANISM: Artificial sequence
```

```
<220> FEATURE:
<223> OTHER INFORMATION: synthetic linker

<400> SEQUENCE: 85

Asp Pro Asn Ser Thr Asn Tyr Glu Glu Ser
1               5                   10

<210> SEQ ID NO 86
<211> LENGTH: 8
<212> TYPE: PRT
<213> ORGANISM: Artificial sequence
<220> FEATURE:
<223> OTHER INFORMATION: synthetic linker

<400> SEQUENCE: 86

Thr Ala Gly Pro Leu Leu Ala Ala
1               5

<210> SEQ ID NO 87
<211> LENGTH: 14
<212> TYPE: PRT
<213> ORGANISM: Artificial sequence
<220> FEATURE:
<223> OTHER INFORMATION: synthetic linker

<400> SEQUENCE: 87

Glu Val Pro Gly Leu Gly Pro Ser Ser Lys Val Thr Thr Pro
1               5                   10

<210> SEQ ID NO 88
<211> LENGTH: 7
<212> TYPE: PRT
<213> ORGANISM: Artificial sequence
<220> FEATURE:
<223> OTHER INFORMATION: synthetic linker

<400> SEQUENCE: 88

Glu Ser Arg Gly Leu Ile Ala
1               5

<210> SEQ ID NO 89
<211> LENGTH: 21
<212> TYPE: PRT
<213> ORGANISM: Artificial sequence
<220> FEATURE:
<223> OTHER INFORMATION: synthetic linker

<400> SEQUENCE: 89

Ile Asn Tyr Tyr Pro Pro Lys Pro Thr Val Pro Asn Ser Thr Pro Gln
1               5                   10                  15

Thr Val Glu Met Glu
            20

<210> SEQ ID NO 90
<211> LENGTH: 8
<212> TYPE: PRT
<213> ORGANISM: Artificial sequence
<220> FEATURE:
<223> OTHER INFORMATION: synthetic linker

<400> SEQUENCE: 90

Thr Glu Ala Glu Gly Arg Gly Ser
1               5

<210> SEQ ID NO 91
<211> LENGTH: 17
<212> TYPE: PRT
```

<213> ORGANISM: Artificial sequence
<220> FEATURE:
<223> OTHER INFORMATION: synthetic linker

<400> SEQUENCE: 91

Thr Pro Ala Thr Pro Pro Glu Tyr Thr Val Glu Pro Gly Gly Ala
1               5                   10                  15

Glu

<210> SEQ ID NO 92
<211> LENGTH: 31
<212> TYPE: PRT
<213> ORGANISM: Artificial sequence
<220> FEATURE:
<223> OTHER INFORMATION: synthetic linker

<400> SEQUENCE: 92

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln
            20                  25                  30

<210> SEQ ID NO 93
<211> LENGTH: 35
<212> TYPE: PRT
<213> ORGANISM: Artificial sequence
<220> FEATURE:
<223> OTHER INFORMATION: synthetic linker

<400> SEQUENCE: 93

Pro Phe Lys Val Ala Gly Asn Asn Asp Thr Val Ile Met Asp Asn Asn
1               5                   10                  15

Val Ser Lys Gln Val His Pro Pro Ile Asp Pro Asn Ser Thr Asn Tyr
            20                  25                  30

Glu Glu Ser
        35

<210> SEQ ID NO 94
<211> LENGTH: 60
<212> TYPE: PRT
<213> ORGANISM: Artificial sequence
<220> FEATURE:
<223> OTHER INFORMATION: synthetic linker

<400> SEQUENCE: 94

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile Asp Pro Asn Ser Thr Asn Tyr Glu Glu Ser
    50                  55                  60

<210> SEQ ID NO 95
<211> LENGTH: 25
<212> TYPE: PRT
<213> ORGANISM: Artificial sequence
<220> FEATURE:
<223> OTHER INFORMATION: synthetic linker

<400> SEQUENCE: 95

Thr Glu Ala Glu Gly Arg Gly Ser Thr Pro Ala Thr Pro Pro Pro Glu
1               5                   10                  15

Tyr Thr Val Glu Pro Gly Gly Ala Glu
            20                  25

<210> SEQ ID NO 96
<211> LENGTH: 44
<212> TYPE: PRT
<213> ORGANISM: Artificial sequence
<220> FEATURE:
<223> OTHER INFORMATION: synthetic linker

<400> SEQUENCE: 96

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln Arg
            20                  25                  30

Ile Ser Gly Asp Phe Phe Pro Gly Ile Val Val Pro
        35                  40

<210> SEQ ID NO 97
<211> LENGTH: 44
<212> TYPE: PRT
<213> ORGANISM: Artificial sequence
<220> FEATURE:
<223> OTHER INFORMATION: synthetic linker

<400> SEQUENCE: 97

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gly Arg
            20                  25                  30

Ile Ser Gly Asp Phe Phe Pro Gly Ile Val Val Pro
        35                  40

<210> SEQ ID NO 98
<211> LENGTH: 35
<212> TYPE: PRT
<213> ORGANISM: Artificial sequence
<220> FEATURE:
<223> OTHER INFORMATION: synthetic linker

<400> SEQUENCE: 98

Pro Phe Lys Val Ala Gly Asn Asn Asp Thr Val Ile Met Asp Asn Asn
1               5                   10                  15

Val Ser Lys Gln Val His Pro Pro Gly Asp Pro Asn Ser Thr Asn Tyr
            20                  25                  30

Glu Glu Ser
        35

<210> SEQ ID NO 99
<211> LENGTH: 25
<212> TYPE: PRT
<213> ORGANISM: Artificial sequence
<220> FEATURE:
<223> OTHER INFORMATION: synthetic linker

<400> SEQUENCE: 99

Thr Glu Ala Glu Gly Arg Gly Ser Thr Pro Ala Thr Pro Pro Glu
1               5                   10                  15

Gly Thr Val Glu Pro Gly Gly Ala Glu
            20                  25

<210> SEQ ID NO 100
<211> LENGTH: 60

```
<212> TYPE: PRT
<213> ORGANISM: Artificial sequence
<220> FEATURE:
<223> OTHER INFORMATION: synthetic linker

<400> SEQUENCE: 100

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
                20                  25                  30

Glu Asp Lys Gln Ala Glu Met Glu Val Asp Ser Lys Gln Val His Arg
            35                  40                  45

Gly Gly Asp Pro Asn Ser Thr Asn Tyr Glu Glu Ser
    50                  55                  60

<210> SEQ ID NO 101
<211> LENGTH: 35
<212> TYPE: PRT
<213> ORGANISM: Artificial sequence
<220> FEATURE:
<223> OTHER INFORMATION: synthetic linker

<400> SEQUENCE: 101

Pro Phe Lys Val Ala Gly Asn Asn Asp Thr Val Ile Met Asp Asn Asn
1               5                   10                  15

Val Ser Lys Gln Val His Pro Gly Gly Asp Pro Asn Ser Thr Asn Tyr
                20                  25                  30

Glu Glu Ser
        35

<210> SEQ ID NO 102
<211> LENGTH: 35
<212> TYPE: PRT
<213> ORGANISM: Artificial sequence
<220> FEATURE:
<223> OTHER INFORMATION: synthetic linker

<400> SEQUENCE: 102

Pro Phe Lys Val Ala Gly Asn Asn Asp Thr Val Ile Met Asp Asn Asn
1               5                   10                  15

Val Ser Lys Gln Val His Arg Gly Gly Asp Pro Asn Ser Thr Asn Tyr
                20                  25                  30

Glu Glu Ser
        35

<210> SEQ ID NO 103
<211> LENGTH: 60
<212> TYPE: PRT
<213> ORGANISM: Artificial sequence
<220> FEATURE:
<223> OTHER INFORMATION: synthetic linker

<400> SEQUENCE: 103

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
                20                  25                  30

Glu Asp Lys Gln Ala Glu Met Gly Gly Ser Gly Gly Gly Ser Gly
            35                  40                  45

Gly Gly Ser Pro Asn Ser Thr Asn Tyr Glu Glu Ser
    50                  55                  60
```

```
<210> SEQ ID NO 104
<211> LENGTH: 35
<212> TYPE: PRT
<213> ORGANISM: Artificial sequence
<220> FEATURE:
<223> OTHER INFORMATION: synthetic linker

<400> SEQUENCE: 104

Pro Phe Lys Val Ala Gly Asn Asn Asp Thr Val Ile Met Asp Asn Asn
1               5                   10                  15

Val Ser Lys Gly Gly Ser Gly Gly Gly Ser Pro Asn Ser Thr Asn Tyr
            20                  25                  30

Glu Glu Ser
        35

<210> SEQ ID NO 105
<211> LENGTH: 35
<212> TYPE: PRT
<213> ORGANISM: Artificial sequence
<220> FEATURE:
<223> OTHER INFORMATION: synthetic linker

<400> SEQUENCE: 105

Pro Phe Lys Val Ala Gly Asn Asn Asp Thr Val Ile Met Asp Gly Gly
1               5                   10                  15

Gly Ser Gly Gly Gly Ser Gly Gly Gly Ser Pro Asn Ser Thr Asn Tyr
            20                  25                  30

Glu Glu Ser
        35

<210> SEQ ID NO 106
<211> LENGTH: 60
<212> TYPE: PRT
<213> ORGANISM: Artificial sequence
<220> FEATURE:
<223> OTHER INFORMATION: synthetic linker

<400> SEQUENCE: 106

Pro Phe Lys Val Ala Gly Asn Asn Asp Thr Val Ile Met Asp Asn Asn
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Lys Gln Val His Pro
        35                  40                  45

Pro Ile Asp Pro Asn Ser Thr Asn Tyr Glu Glu Ser
    50                  55                  60

<210> SEQ ID NO 107
<211> LENGTH: 60
<212> TYPE: PRT
<213> ORGANISM: Artificial sequence
<220> FEATURE:
<223> OTHER INFORMATION: synthetic linker

<400> SEQUENCE: 107

Pro Phe Lys Val Ala Gly Asn Asn Asp Thr Val Ile Met Asp Asn Asn
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Asp Pro Asn Ser Thr Asn Tyr Glu Glu Ser
    50                  55                  60
```

<210> SEQ ID NO 108
<211> LENGTH: 35
<212> TYPE: PRT
<213> ORGANISM: Artificial sequence
<220> FEATURE:
<223> OTHER INFORMATION: synthetic linker

<400> SEQUENCE: 108

Pro Phe Lys Val Ala Gly Asn Asn Asp Thr Val Ile Met Asp Asn Asn
1               5                   10                  15

Val Ser Lys Gln Val His Pro Pro Ile Asp Pro Asn Ser Thr Asn Tyr
            20                  25                  30

Glu Glu Ser
        35

<210> SEQ ID NO 109
<211> LENGTH: 48
<212> TYPE: PRT
<213> ORGANISM: Artificial sequence
<220> FEATURE:
<223> OTHER INFORMATION: synthetic linker

<400> SEQUENCE: 109

Pro Phe Lys Val Ala Gly Asn Asn Asp Thr Val Ile Met Asp Asn Asn
1               5                   10                  15

Val Ser Lys Gln Val His Pro Pro Ile Met Asp Asn Asn Val Ser Lys
            20                  25                  30

Gln Val His Pro Pro Ile Asp Pro Asn Ser Thr Asn Tyr Glu Glu Ser
        35                  40                  45

<210> SEQ ID NO 110
<211> LENGTH: 32
<212> TYPE: PRT
<213> ORGANISM: Artificial sequence
<220> FEATURE:
<223> OTHER INFORMATION: synthetic linker

<400> SEQUENCE: 110

Pro Phe Lys Val Ala Gly Asn Asn Asp Thr Val Ile Met Asp Asn Asn
1               5                   10                  15

Val Ser Lys Gln Val His Pro Asn Ser Thr Asn Tyr Glu Glu Ser
            20                  25                  30

<210> SEQ ID NO 111
<211> LENGTH: 43
<212> TYPE: PRT
<213> ORGANISM: Artificial sequence
<220> FEATURE:
<223> OTHER INFORMATION: synthetic linker

<400> SEQUENCE: 111

Pro Phe Lys Val Ala Gly Asn Asn Asp Thr Val Ile Met Asp Asn Asn
1               5                   10                  15

Val Ser Lys Gln Val His Pro Pro Ile Gly Gly Gly Gly Gly Gly
            20                  25                  30

Gly Asp Pro Asn Ser Thr Asn Tyr Glu Glu Ser
        35                  40

<210> SEQ ID NO 112
<211> LENGTH: 47
<212> TYPE: PRT
<213> ORGANISM: Artificial sequence
<220> FEATURE:

<223> OTHER INFORMATION: synthetic linker

<400> SEQUENCE: 112

Pro Phe Lys Val Ala Gly Asn Asn Asp Thr Val Ile Met Asp Asn Asn
1               5                   10                  15

Val Ser Lys Gln Val His Pro Pro Ile Ser Gly Gly Ser Gly Gly
            20                  25                  30

Gly Ser Gly Gly Gly Asp Pro Asn Ser Thr Asn Tyr Glu Glu Ser
        35                  40                  45

<210> SEQ ID NO 113
<211> LENGTH: 60
<212> TYPE: PRT
<213> ORGANISM: Artificial sequence
<220> FEATURE:
<223> OTHER INFORMATION: synthetic linker

<400> SEQUENCE: 113

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile Asp Pro Asn Ser Thr Asn Tyr Glu Glu Ser
    50                  55                  60

<210> SEQ ID NO 114
<211> LENGTH: 53
<212> TYPE: PRT
<213> ORGANISM: Artificial sequence
<220> FEATURE:
<223> OTHER INFORMATION: synthetic linker

<400> SEQUENCE: 114

Pro Phe Lys Val Ala Gly Asn Asn Asp Thr Val Ile Met Asp Asn Asn
1               5                   10                  15

Ile His Arg Leu Pro His Ala Thr Arg Glu Asp Lys Gln Ala Glu Met
            20                  25                  30

Glu Val Asp Ser Lys Gln Val His Pro Pro Ile Asp Pro Asn Ser Thr
        35                  40                  45

Asn Tyr Glu Glu Ser
    50

<210> SEQ ID NO 115
<211> LENGTH: 25
<212> TYPE: PRT
<213> ORGANISM: Artificial sequence
<220> FEATURE:
<223> OTHER INFORMATION: synthetic linker

<400> SEQUENCE: 115

Thr Glu Ala Glu Gly Arg Gly Ser Thr Pro Ala Thr Pro Pro Glu
1               5                   10                  15

Tyr Thr Val Glu Pro Gly Gly Ala Glu
            20                  25

<210> SEQ ID NO 116
<211> LENGTH: 35
<212> TYPE: PRT
<213> ORGANISM: Artificial sequence
<220> FEATURE:
<223> OTHER INFORMATION: synthetic linker

```
<400> SEQUENCE: 116

Thr Glu Ala Glu Gly Arg Gly Ser Gly Gly Gly Gly Gly Gly Gly Gly
1               5                   10                  15

Gly Gly Thr Pro Ala Thr Pro Pro Glu Tyr Thr Val Glu Pro Gly
            20                  25                  30

Gly Ala Glu
        35

<210> SEQ ID NO 117
<211> LENGTH: 44
<212> TYPE: PRT
<213> ORGANISM: Artificial sequence
<220> FEATURE:
<223> OTHER INFORMATION: synthetic linker

<400> SEQUENCE: 117

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln Arg
            20                  25                  30

Ile Ser Gly Asp Phe Phe Pro Gly Ile Val Val Pro
        35                  40

<210> SEQ ID NO 118
<211> LENGTH: 40
<212> TYPE: PRT
<213> ORGANISM: Artificial sequence
<220> FEATURE:
<223> OTHER INFORMATION: synthetic linker

<400> SEQUENCE: 118

Asp Glu Pro Ala Leu Thr Val Gly Asn Glu Ser Lys Lys Gln Asp Ser
1               5                   10                  15

Asp Ser Lys Met Gly Thr Gly His Ser Asp Leu Asn Gln Arg Ile Ser
            20                  25                  30

Gly Asp Pro Gly Ile Val Val Pro
        35                  40

<210> SEQ ID NO 119
<211> LENGTH: 25
<212> TYPE: PRT
<213> ORGANISM: Artificial sequence
<220> FEATURE:
<223> OTHER INFORMATION: Synthetic linker
<220> FEATURE:
<221> NAME/KEY: 223
<222> LOCATION: (1)..(25)
<223> OTHER INFORMATION: synthetic linker 1; corresponds to SEQ ID NO 82
      as referred to in document WO 2008/113185 on page 46 line 8

<400> SEQUENCE: 119

Pro Phe Lys Val Ala Gly Asn Asn Asp Thr Val Ile Met Asp Asn Asn
1               5                   10                  15

Val Ser Lys Gln Val His Pro Pro Ile
            20                  25

<210> SEQ ID NO 120
<211> LENGTH: 13
<212> TYPE: PRT
<213> ORGANISM: Artificial sequence
<220> FEATURE:
<223> OTHER INFORMATION: synthetic linker
<220> FEATURE:
<221> NAME/KEY: 223
```

```
<222> LOCATION: (1)..(13)
<223> OTHER INFORMATION: synthetic linker 38; corresponds to SEQ ID NO
      92 as referred to in document WO 2008/113185 in Table II on page
      46 line 20

<400> SEQUENCE: 120

Arg Ile Ser Gly Asp Phe Phe Pro Gly Ile Val Val Pro
1               5                   10

<210> SEQ ID NO 121
<211> LENGTH: 17
<212> TYPE: PRT
<213> ORGANISM: Artificial Sequence
<220> FEATURE:
<223> OTHER INFORMATION: His/Thrombin Cleavage Site

<400> SEQUENCE: 121

His His His His His His His His His Gly Gly Ser Phe Asn Pro
1               5                   10                  15

Arg
```